United States Patent [19]
Huang

[11] Patent Number: 5,645,994
[45] Date of Patent: Jul. 8, 1997

[54] METHOD AND COMPOSITIONS FOR IDENTIFICATION OF SPECIES IN A SAMPLE USING TYPE II TOPOISOMERASE SEQUENCES

[75] Inventor: Wai Mun Huang, Salt Lake City, Utah

[73] Assignee: University of Utah Research Foundation, Salt Lake City, Utah

[21] Appl. No.: 470,179

[22] Filed: Jun. 6, 1995

Related U.S. Application Data

[63] Continuation-in-part of Ser. No. 106,482, Aug. 13, 1993, abandoned, which is a continuation-in-part of Ser. No. 548,138, Jul. 5, 1990, abandoned.

[51] Int. Cl.$^6$ .................. C12Q 1/68; C07H 21/04
[52] U.S. Cl. .................. 435/6; 435/5; 435/91.2; 435/810; 436/501; 536/23.1; 536/24.1; 536/24.3; 536/24.31; 536/24.32; 536/24.33; 935/77; 935/78
[58] Field of Search .................. 435/5, 6, 91.3, 435/810; 436/501; 536/22.1, 23.1, 24.1, 24.3–24.33; 935/77, 78

[56] References Cited

U.S. PATENT DOCUMENTS

| | | | |
|---|---|---|---|
| 3,963,700 | 6/1976 | Philip | 260/236.5 |
| 4,083,779 | 4/1978 | Combe et al. | 210/23 H |
| 4,309,207 | 1/1982 | Devlin | 71/79 |
| 4,358,535 | 11/1982 | Falkow et al. | 435/5 |
| 4,480,040 | 10/1984 | Owens et al. | 436/504 |
| 4,652,448 | 3/1987 | Sadowski | 424/87 |
| 4,683,195 | 7/1987 | Mullis et al. | 435/6 |
| 4,717,653 | 1/1988 | Webster | 435/5 |
| 4,731,325 | 3/1988 | Palva et al. | 435/6 |
| 4,775,477 | 10/1988 | Stahl et al. | 210/641 |
| 4,801,530 | 1/1989 | Nogueira et al. | 435/6 |
| 4,857,327 | 8/1989 | Virdalm | 424/195.1 |
| 4,861,709 | 8/1989 | Ulitzur et al. | 435/5 |
| 4,886,743 | 12/1989 | Hood et al. | 435/5 |
| 4,994,370 | 2/1991 | Silver et al. | 435/6 |
| 5,087,558 | 2/1992 | Webster | 435/5 |
| 5,128,100 | 7/1992 | Hollis et al. | 422/14 |
| 5,200,186 | 4/1993 | Gabetta et al. | 424/195.1 |

FOREIGN PATENT DOCUMENTS

| | | |
|---|---|---|
| 3027933 | 7/1980 | Germany . |
| 3427014 | 1/1986 | Germany . |
| 8810315 | 12/1988 | WIPO . |
| 8911547 | 11/1989 | WIPO . |

OTHER PUBLICATIONS

Mack et al. (1988) Proc. Natl Acad Sci (USA), vol. 85, pp. 6977–6981.
Shibata et al. (1988) J. Exp. Med., vol. 167, pp. 225–230.
Jeffreys et al. (1988) Nuc. Acids Res., vol. 16, No. 23, pp. 10953–10971.
Marx, Science, vol. 240, (1988) pp. 1616–1618.

(List continued on next page.)

*Primary Examiner*—Ardin H. Marschel
*Attorney, Agent, or Firm*—Trask, Britt & Rossa

[57] ABSTRACT

A method of identifying species in a sample is based on pairs of consensus amino acid segments which flank variable amino acid segments of type II DNA topoisomerases. In one embodiment, a DNA primer composition termed "universal primers", is used to amplify the DNA segments coding for the variable or "signature" amino acid sequences. The amplified segments are then cloned and sequenced, and the DNA sequence is matched against a database of signature sequences from multiple species. The signature DNA sequences may be convened to the amino acid "signature" sequences for which they code, and these signature sequences matched against a database of amino acid reference sequences, thereby determining which species were present in the original sample. The universal DNA primers are useful to detect and identify multiple unknown microbial species in a sample. In another embodiment, a specific primer pair specific for a particular organism is provided, which has sequences derived from the signature regions between the flanking conserved regions. A general method for selecting a suitable protein and producing universal primers based upon it is also provided.

43 Claims, 11 Drawing Sheets

OTHER PUBLICATIONS

Belland et al., "Neisseria gonorrhoeae acquires mutations in analogoes regions of gyrA and parc in fluoroquinolone–resistant isolates", Molecular Microbiology (1994) 14(2), pp. 371–380.

Fuleki et al., "Quantitative Methods for Anthocyanins. 1. Extraction and Determination of Total Anthocyanin in Cranberries", Journal Of Food Science, vol. 33 (1968), pp.72–76.

Fuleki et al., "Quantitative Methods for Anthocyanins. 3. Purification of Cranberry Anthocyanins", Journal Of Food Science, vol. 33 (1968), pp. 266–274.

Huang, Wai Mun, "Multiple DNA Gyrase–Like Genes In Eubacteria", Molecular Biology of DNA and Its Application to Chemotherapy, 1991, pp. 39–48.

Puski et al., "Flavonol Glycosides in Cranberries", Journal Of Food Science, vol. 32 (1967), pp. 527–530.

Takiff et al., "Cloning and Nucleotide Sequence of Mycobacterium tuberculosis gryA and gyrB Genes and Detection of Quinolone Resistance Mutations", Antimicr. Agents & Chemo., V. 38, No. 4, Apr. 1994, 773–780.

Wang et al., "Isolation and Characterization Of Polyphenolic Compounds In Cranberries", Journal Of Food Science, vol. 43, No. 5 (1978), pp. 1402–1404.

Wyckoff et al., "Structure of the Drosophila DNA Topoisomerase II Gene Nucleotide Sequence and Homology Among Toposiomerases II", J. Mol. Biol, (1989) 205, pp. 1–13.

| | | 2 **** | | | | | | 4 ****** |
|---|---|---|---|---|---|---|---|---|
| | | ******* | | | | | | ******** |
| | | KRPGMYIGDTDDGTGLHHMVFEVVDNAIDEALAGHCKEIIVTIHADNSVS-VQDDGRGIP | | | | | | |
| Escherichia coli | (EC) | | | | | | | |
| Shigella dysenteriae | (SD) | DTDDGT | MVF | VV | AI | ALA | HCKEIIVTIHADNS

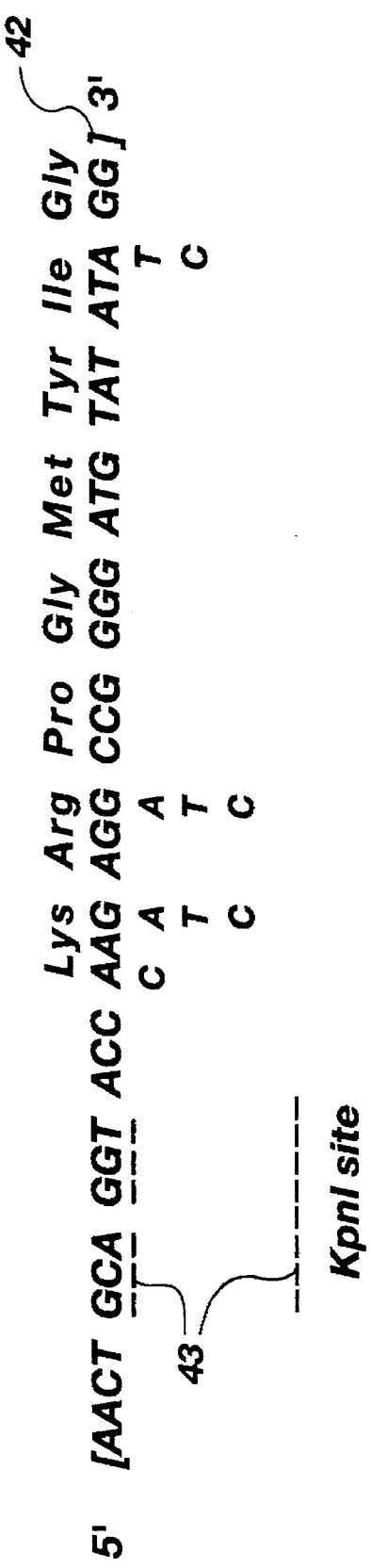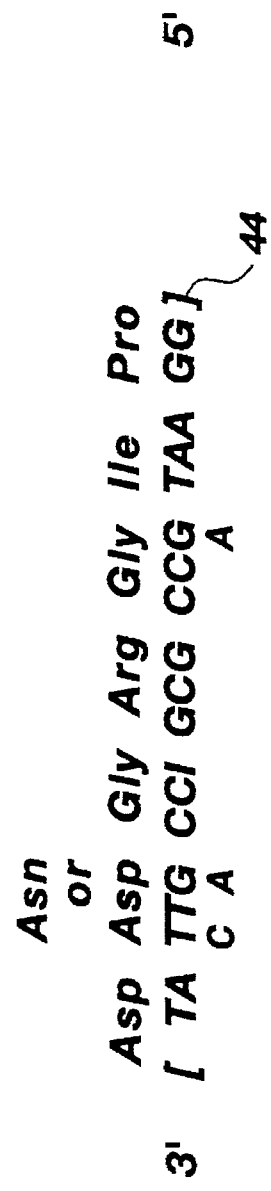
Fig. 3

```
                                           12
                                    ********
Escherichia coli            (EC)   DGLKPVHRR-VLYAMNVLGNDWNKAYKKSARVVGDVIGKYHPHGDSAVYDTIVRMAQPF
Shigella dysenteriae        (SD)   -VLYAMNVLGNDWNKAYK  SARVV  DVIGKY  SAVYDTIVRL  QPF
Salmonella typhiumurium     (ST)   -VLYAMNVLGNDWNKAYK  SARVV  DVIGKY  SAVYDTIVRM  QPF
Klebsiella pneumoniae       (KP)   -VLYAMNVLGNDWNKAYK  SARVV  DVIGKY  TAVYDTIVRM  QPF
Pseudomonas aeruginosa      (PA)   -VLYAMSELGNDWNKAYK  SARVV  DVIGKY  TAVYDTIVRL  QPF
Legionella pneumoniae       (LP)   -VLYAMSELGNDWNKPYK  SARTV  DVLGKF  SACYEAMVLMQPF
Neisseria gonorrhoeas       (NGa)  KIVYAMSELGLKATAKYK  SARTV  DVLGKF  SSAYEAMVRMQDF
                            (NGb)  -ILFAMRDMGLTAGANRV  SARVV  EILGKY  SAVYDTIVRM   QPF
Bacillus subtilis           (BS)   -VLYAMHELKNNWNAAYK  SARIV  DVIGKY  SAVYESMVRMQDF
Borrelia burgdorferi        (BBa)  -ILYAMNDLGMTSDKPYK  SARIV  EVIGKY  QSIYDALVRL   QDF
                            (BBb)  -ILYSMYEMGLRSDKAFK  AGRIV  DVLGKY  TSIYEALVNI   NKD
Chlamydia trachomatis       (CT)   -IIHSLFEM---HDGNFH  VRNVV  -NTMKY  APIVEALVVL   NKG
                                   -LLWTLFRM---DDGKMH  VANIA  -RTMAL
                                                                                      ⎤
                                                                                      │
                                                                                      ├ 16
                                                                                      │
T4                          (T4)   DGFKPVQRF-VIARALDLARGNKDKFHKLASIAGGVADLGYHHGETLHKSQCLMANTWN
Homo sapiens                (HS)   DGLKPGQRK-VLFTCFKRNDKREVKVAQLAGSVAEMSSYHHGEMSLMMTIINLAQNFVG
Saccharomyces cerevisiae    (SC)   DGFKPGQRK-VLYGCFKKNLKSELKVAQLAPYVSECTAYHHGEQSLAQTIIGLAQNFVG
Schizosaccharomyces pombe   (SP)   DGLKPGQRKVVYCFKRNLVHETKVSRLAGYVASETAYHHGEVSMEQTIVNLAQNFVGS
                                                                                      ⎦
```

*Fig. 5A*

```
                                                            ┌─ 14 ─┐
                           ┌──── 18 ────┐                   *  * **
                           *  *  * (7-9)  *  **
     SLYRYMLVDGQGNFGSIDGD-SAAAMRYTEIRLAKIAHELMADLEKETVDFVDNYDGTE KIPDVMPTKIPNLLVNGSSGIAVGMA
(SD) SL  MLVD Q  F  SIDGD-SA    M  T  IRLAKIAHELMADLEKE VDFVD  Y  GTE  KI  DVM  TKI  NL  VN  SS
(ST) SL  MLVD Q  F  SIDGD-SA    M  T  IRLAKIAHELMADLEKE VDFVD  Y  GTE  KI  DVM  TKI  NL  VN  SS
(KP) SL  MLVD Q  F  SVDGD-SA    M  T  IRMSKIAHELMADLEKE VDFVD  Y  GTE  KI  DVM  TKI  NL  VN  SF
(PA) SL  MLVD Q  F  SVDGD-NA    M  T  IRMAKLAHELLADLEKE VDWVP  Y  GTE  QI  AVM  TKI  NL  VN  SS
(LP) SY  PFVD Q  W  SPDDPKSF    M  T  VRMAKLAHELLADLEKE VDWVD  F  GTL  QE  ALL  ARL  NI  LN  AT
(NGa)TL  PLID I  F  SRDGD-GA    M  T  ARLSHYADVLLGELLQG VDFMP  Y  GAF  DE  LHL  ARL  MV  LN  AS
(NGb)AM  VLID Q  F  SVDGL-AA    M  T  AGLTPIAELLLSEINQG VNFGP  Y  GSE  HE  LVL  TRF  TL  VN  SS
(BS) NY  MLVD H  F  SVDGD-SA    M  T  IRMAKISHEMLADIEEE IDYQD  Y  GSE  RE  VVM  SRF  NL  VN  AA
(BBa)SL  PRNT Q  F  SIDGD-PP    M  T  ARMSKISMEILRDITKD VNFKS  Y  DSL  SE  EIM  SSF  FL  VN  SS
(BBb)LF----IEK- Q  F  NLFTGDPAS S    I  AKMEKITEYIVKDIDKE IYESS- Y  GRN  NE  LLY  AKI  VI  IQ  SE
(CT) FL----IET- Q  F  NPLTGDPHAA    I  CRLTPLAFDVLYSKEIT- TFHDS- Y  GRE  QE  DIL  AKI  LL  LH  VD
                                      ARLSPLAKEVLFNTDLM-
                                  └─────────── 16 ───────────┘

(T4) NNFPLL-DGQGNFGGSRTVQ-KAAASRYIFARVSKNFYNVYKDTEYAPVHQDKEHIPPA F----YLPIIPTVLLNGVS-GIATGYA
(HS) SNNLNLLQPIGGQFGTRLHGGKDSASPRYIFTMLSSLARLLFPPKDDHTLKFLYDDNQRV EPEW-YIPIIPMVLINGAE-GIGTGWS
(SC) SNNIYLLLPNGAFGTRATGGKDAAAARYIYTELNKLTRKIFHPADDPLYKYIQEDEKTV EPEW-YLPILPMILVNGAE-GIGTGRS
(SP) NNINLLMPNGQFGTRSE-GGKNASASRYLNTALSPLARVLFNSNDDQLLNYQNDEGQWI EPEY-YVPILPMVLVNGAE-GIGTGWS
     └──────────────────── 16 ────────────────────┘
```

*Fig. 5B*

| | | 800 | 806 | | | 808 | 802 |
|---|---|---|---|---|---|---|---|
| | | ******** | | | | | ******* |
| | | KRPGMYI | GDTDDDGTGLHHMVFEVVDNAIDEALAGH | | | CKEIIVTIHADNSVS-VQ | DDGRGIP |
| Escherichia coli | (EC) | | DTDDGT | MVF | VV | AI | ALA | HCKEIIVTIHADNSVS-VQ |
| Shigella dysenteriae | (SD) | | DTDDGT | MVF | VV | AI | ALA | HCKDIVTIHADNSVS-VT |
| Salmonella typhiumurium | (ST) | | DTDDGT | MVF | VV | SI | ALA | YCSEISITHTDESIT-VR |
| Pseudomonas aeruginosa | (PA) | | DTDDGT | MVF | VV | SI | SLA | YCKEIFVTIHSDESIT-VK |
| Legionella pneumoniae | (LP) | | DTDDGS | MVY | VV | AI | ALA | HADLVTVTLNADGSVT-VT |
| Agrobacterium tumefaciens | (AT) | | DVGDGS | MIY | VV | AI | SLA | YCDLVRVTLNKNGSVT-VS |
| Rickettsia rickettsii | (RR) | | DTDDGS | MVY | VV | GI | ALA | HANYVAVKIHADSSVS-VR |
| Rhodobacter capsulatus | (RC) | | DTDDGS | MVY | VV | GI | ALA | HATEVAVIIHADDSVS-VR |
| Rhodopseudomonas sphaeroides | (RS) | | DTQDGS | MVF | VL | AI | ALA | HCDKIRVIIHADNSVS-VF |
| Neisseria denitrificans | (ND) | | DTN/G- | MIY | VV | SI | AMA | HCDTIDVEITTEGSCI-VS |
| Campylobacter jejuni | (CJ) | | STGPK- | LVY | VV | AV | ALA | YCNTIDVRLLEDGSCQ-VT |
| Anacystis nidulans | (AN) | | DTGVT- | LVY | VV | SI | AMA | FCTEVVRILEDGGIS-IS |
| Chlamydia trachomatis | (CT) | | STNSK- | LVW | IV | SI | ALA | YCTDINIQIEKDNSIT-VV |
| Bacillus subtilis | (BS) | | SVSIN- | LVY | VV | SI | ALA | FCDRIDVIINLDNTIT-VI |
| Borrelia burgdorferi | (BB) | | STGEE- | MIW | II | SI | AMG | FASTVKLTL-KDNFVTIVE |
| Mycoplasma pneumoniae | (MP) | | | | | | | |

```
                               *********
                               DGLKPVHRR-VLYAMNVLGNDWNKAYKKSARVVGDVIGKYHPHGDSAVVYDTIVRMAQPF
Escherichia coli         (EC)  -VLYAMNVLGNDWNKAYK    SARVV     DVIGKY     SAVVYDTIVRL  QPF
Shigella dysenteriae     (SD)  -VLYAMNVLGNDWNKAYK    SARVV     DVIGKY     SAVVYDTIVRM  QPF
Salmonella typhiumurium  (ST)  -VLYAMNVLGNDWNKAYK    SARVV     DVIGKY     TAVVYDTIVRM  QPF
Klebsiella pneumoniae    (KP)  -VLYAMNVLGNDWNKAYK    SARVV     DVIGKY     TAVVYDTIVRL  QPF
Pseudomonas aeruginosa   (PA)  -VLYAMSELGNDWNKPYK    SARTV     DVLGKF     SACYEAMVLMQPF
Legionella pneumoniae    (LP)  KIVYAMSELGLKATAKYK    SARTV     EILGKY     SSAYEAMVRMQDF
Neisseria gonorrhoeas    (NGa) -ILFAMRDMGLTAGANRV    SARIV     DVIGKY     SAVVYDTIVRM  QNF
                         (NGb) -VLYAMHELKNNWNAAYK    SARIV     EVIGKY     SAVVESMVRMQDF
Bacillus subtilis        (BS)  -ILYAMNDLGMTSDKPYK    AGRIV     DVLFKY     QSIYDALVRL   QDF
Borrelia burgdorferi     (BBa) -ILYSMYEMGLRSDKAFK    VRNVV     -NTMKY     TSIYEALVNI   NKD
                         (BBb) -IIHSLFEM---HDGNFH    VANIA     -RTMAL     APIVEALVVL   NKG
Chlamydia trachomatis    (CT)  -LLWTLFRM---DDGKMH
                                                                   } 904

T4                       (T4)  DGFKPVQRF-VIARALDLARGNKDKFHKLASIAGGVADLGYHHGETLHKSQCLMANTWN
Homo sapiens             (HS)  DGLKPGQRK-VLFTCFKRNDKREVKVAQLAGSVAEMSSYHHGEMSLMMTIINLAQNFVG
Saccharomyces cerevisiae (SC)  DGFKPGQRK-VLYGCFKKNLKSELKVAQLAPYVSECTAYHHGEQSLAQTIIGLAQNFVG
Schizosaccharomyces pombe(SP)  DGLKPGQRKVVYYCFKRNLVHETKVSRLAGYVASETAYHHGEVSMEQTIVNLAQNFVGS
```

METHOD AND COMPOSITIONS FOR IDENTIFICATION OF SPECIES IN A SAMPLE USING TYPE II TOPOISOMERASE SEQUENCES

BACKGROUND OF THE INVENTION

Related Applications

This application is a continuation-in-part of application Ser. No. 08/106,482 filed Aug. 13, 1993, now abandoned, which is in turn a continuation-in-part of application Ser. No. 07/548,138 filed Jul. 5, 1990, now abandoned.

This invention was made with the support of the U.S. Government under Grant Number GM21960 awarded by the National Institutes of Health. The government has certain rights in the invention subject to the provisions of 37 C.F.R. §401 and 45 C.F.R. §8.

FIELD

This application relates generally to the identification of microbes, and more specifically to detection of multiple species by means of DNA and amino acid sequences.

STATE OF THE ART

Traditional methods for identification of microbes causing diseases in humans, animals or plants involve culturing samples of tissue or fluid from the subject, followed by staining and microscopy to ascertain which species were present. Culturing is necessary to produce sufficient numbers of the microbes for the morphological and staining analysis, but may require one to several days to accomplish. Furthermore, different microbes have different culture requirements. Most samples contain a wide range of microbes, so to maximize the possibility of detection, replicate cultures must be established on different media. This is labor-intensive and may not be practical in cases where only small volumes of sample are available. Moreover, for some organisms there are no known means of culture. In fact, it is believed that there may be many bacterial species which have escaped detection due to the lack of the ability to culture them (L. G. Wayne et al., Int. J. System. Bacter. 37:463–464, 1987). Thus, some species in the original sample may go undetected, simply because the requirements for their culture are not met.

In many cases, the staining and morphological analysis are insufficient for a definitive identification. Various tests for specific enzyme activities which correspond to different groups or species of microbes have been developed to supplement the morphological tests. However, these too are time-consuming and generally require culture in order to provide sufficient material for the tests. A battery of tests may be required, thus multiplying the labor and the amount of sample needed for the analysis.

More recently, methods have been developed which employ various organism-specific probes. These methods utilize amino acid or DNA sequences unique to the organism whose detection is sought. Generally, the probes are either antibodies to a protein or peptide, or DNA or RNA segments which are complementary to (and thus can be hybridized to) a nucleic acid sequence unique to the organism. The probe must be tagged so that its binding to the target sequence is observable. Examples of the use of nucleic acid probes for detection of microorganisms can be found in U.S. Pat. Nos. 4,785,086 to Fills et al., 4,801,530 to Nogueira et al., 4,731,325 to Palva et al., and 4,652,517 to Jollick et al. The technique is also applicable to the identification of subpopulations of cells within an organism, provided those subpopulations have unique marker sequences. Such an application is described in U.S. Pat. No. 4,886,743 to Hood et al.

However, these methods are limited in usefulness when applied to a sample containing a mixture of organisms. They can only confirm the presence of a suspected organism in the sample. No information is obtained as to the presence of other organisms in the sample. A different probe is required for each organism sought to be identified. Thus, the diagnostician must guess which probe or probes to utilize for a given sample, and multiple tests with different probes may be required. Furthermore, probes do not yet exist for many microbes. Also, the probe binding assays all have some degree of background binding or noise. If a pathogen causing or contributing to the condition is present in small proportions, it may not be detectable over the background. Thus, the sensitivity of these methods is limited by the amount of the organism in the sample. The sensitivity of detection also depends in part on the amount of the "target" sequence (the sequence to which the probe binds) present in the organism, which may be very small. Generally, accurate detection requires either large sample volume or culturing with its attendant problems.

An improvement to the use of specific nucleic acid probes involves selective amplification of the target sequence in the cell or organism. Such amplification greatly increases the sensitivity of detection by the tagged probe, by increasing the number of target sequences relative to other DNA in the sample. One means of such amplification is the polymerase chain reaction, hereinafter referred to as PCR. Methods for PCR are disclosed in U.S. Pat. Nos. 4,683,195 and 4,683,202, as well as in Saiki et al., Science 230:1350 (1985); the contents of which are hereby incorporated by reference. Application of PCR to the detection of a virus in human tissues is disclosed in PCT publication no. AU 88/00047 by Morris, and to the detection of human cells having specific chromosomal rearrangements is disclosed in PCT publication no. US 89/00843.

PCR requires a pair of DNA primers corresponding to the left and right flanks of the DNA sequence whose amplification is sought (in this case, the target sequence). When hybridized to a complementary single strand, primers provide a starting point for the action of DNA polymerase, which then extends the primer by adding DNA subunits (termed "nucleotides") starting from the 3' end of the primer. For PCR, the left and right flank primers must be of polarity such that the 3' end is adjacent to the target sequence, so that extension of the primer occurs into the target sequence. Accordingly, the left and right flank primers must hybridize to opposite strands of the original duplex.

A PCR reaction mix containing the desired primers, a DNA polymerase and the required nucleotides is subjected alternately to thermal denaturation rendering the DNA single-stranded and cooling to a temperature permitting hybridization of the primers and extension by the Taq DNA polymerase. Repeated alternation of these cycles leads to amplification of the target sequence of up to a millionfold. The PCR-reacted sample can then be hybridized to the probe sequence. If the target sequence was present in the initial sample, the probe binding signal will be greatly above background due to amplification of the target sequence.

Amplification of a target sequence is also possible with a transcription-based system using a DNA-dependent RNA polymerase, as disclosed in PCT publication no. US 88/02108 by Gingeras et al.

Use of PCR or transcription-based amplification eliminates the troublesome requirement for culturing to produce sufficient material for the probe hybridization analysis. However, a unique set of DNA primers and probe(s) is required for each organism. Consequently, to identify a plurality of microbes in a single sample requires performing replicate PCR and hybridization reactions with different sets of primers and probes. Furthermore, as with the unique sequence probe methods described in the preceding paragraphs, organisms not specifically tested or probed for will go undetected.

Therefore, a need remains for means to identify a plurality of organisms in a single sample, without use of multiple probes, and without the need for successful culture of the organisms. A need also remains for a method for detecting substantially all of the different organisms present in a sample, without any prior knowledge or guesswork as to which organisms may be present. A need further remains for means to detect the presence of one or a few related species in a sample, and to accurately distinguish among similar and/or related species.

DEFINITIONS AND EXPLANATION OF TERMS

For purposes of this application, the following definitions as generally used in the art will be employed.

By "ubiquitous", it is meant that a protein having substantially similar structure and function is found in many or all species. Such a protein from one species may be said to be "homologous to", or a "homologue of", the equivalent protein found in another species. The term homologue may also be applied to genes and other DNA sequences which are found in similar forms in different species.

"Conserved" is defined as meaning that a protein (or gene) which has homologues in many species has at least one segment whose amino acid (or DNA) sequence is substantially shared by the homologues endogenous to different species. The degree to which a given protein or gene is conserved, e.g. highly or poorly, refers in a general sense to the proportion of segments whose sequence is substantially shared among different species. The term conserved may also be applied to segments of a protein or gene. A highly conserved segment whose amino acid sequence is substantially or entirely shared by most species is termed a "consensus sequence". A segment whose amino acid or DNA sequence differs substantially among species is termed a "variable" segment or sequence. The term "signature" sequence will be used as a modifier to denote an amino acid sequence (or the DNA sequences from which it derives), which is found in only one or a very few species.

Additional terms used in this application are "primer" and "hybridize". As generally known in the art, hybridization is the process by which two DNA strands having complementary base sequences selectively bind to each other in an alignment dependent on their mutual nucleotide sequences. The hybridized strands together are termed a "duplex". A DNA primer is a short segment (it may be as few as 10 nucleotides in length) of single-stranded DNA which, when hybridized with an opposing complementary longer DNA strand, can be extended from its 3' end by addition of nucleotide subunits by a DNA polymerase in a manner which depends on the sequence of the opposed strand. The resulting extended portion has a sequence complementary to the opposed strand and forms a duplex with it.

SUMMARY OF THE INVENTION

The invention comprises means to identify one or more species in a sample by selectively amplifying a nucleic acid segment encoding a signature region of a macromolecule which is present in all the organisms of interest. The macromolecule is selected as having a signature region unique to one or a few species flanked by consensus regions which are substantially conserved among the organisms of interest. In a highly preferred embodiment, the macromolecule is a type II topoisomerase (also referred to as "gyrase" in bacterial species). The means for identification comprise a primer composition, together with a method of using the primer composition, optionally in conjunction with a database of residue sequences of the molecule. The primer composition for the selective amplification may desirably be derived by analysis of a database of residue sequences of the macromolecule.

In one embodiment, the invention includes a universal primer composition comprising primers whose DNA sequences are derived from the amino acid sequence of a type II topoisomerase. Type II topoisomerase has been found to contain at least one pair of highly conserved consensus amino acid sequences flanking a variable amino acid "signature" segment. The consensus sequences are selected as being common to the protein from many or all different species, while each signature segment is specific to one or a few species. The primer pair(s) of the universal primer composition are constructed to hybridize to DNA coding for the consensus sequences. In a highly preferred embodiment, the universal primer composition comprises a mixture of most or all of the alternate DNA sequences coding for the same amino acid sequence.

A method of using the universal primer composition comprises selectively amplifying from a sample, the nucleic acid segments coding for the signature segment of organisms in the sample, and sequencing a representative sample of the individual amplified segments. The sequences of individual amplified segments are then each compared to a database containing a plurality of reference signature sequences each corresponding to a particular species. A match with a sequence in the database is diagnostic of the presence of the corresponding organism in the sample. Optionally but desirably, the DNA sequence of each sequenced molecule is first convened to the signature amino acid sequence for which it codes and the reference sequences in the database are amino acid signature sequences. In the preferred embodiment, the matching of the amplified signature sequences against the database, and the conversions of amino acid sequences to DNA sequences and vice-versa, are performed by computing means such as a personal computer.

In another embodiment, the invention includes a specific primer composition comprising "nested" primers having sequences drawn from within the signature sequence region between the consensus regions of topoisomerase II. That is, the specific primer sequences are "nested" within the flanking universal primer sequences. The nested primer composition is useful for rapid and accurately distinguishing among similar and closely-related species, and/or for rapid identification of a single species.

A method of identifying species with the specific primer composition comprises the steps of providing a specific primer composition as described above; making an extract of nucleic acid molecules from a sample; selectively amplifying the nucleic acid segment with the specific primer composition to produce amplified segments; and determining from the amplified segments whether a particular specie(s) corresponding to the primer sequences of the first and second primers is present in the sample. A presently preferred embodiment of the method further includes steps of subjecting the nucleic acid extract to amplification with the universal primers to selectively amplify segments containing signature regions, prior to the step of amplifying with the nested specific primer composition to further selectively amplify sequences from a particular species or subset of species of interest.

Additionally encompassed in the invention are methods for producing universal primer compositions, for producing nested primer compositions, and for construction of a database of reference signature sequences.

Both plant and animal species can be identified using the primer compositions and methods of the invention. The types of samples for which the invention is useful include the following: contaminated food products; tissue or fluid samples from diseased humans, animals, or plants; soil samples; water samples from any source. The invention is described hereinafter primarily with reference to the analysis of samples containing bacterial organisms. However, it is recognized that many other applications are possible, depending only on the compilation of the necessary database of consensus and signature sequences. These include identification of any microbial organisms such as fungi or protozoans, and closely related plant and insect species, which in some cases are virtually indistinguishable by morphological criteria.

In the embodiment employing a universal primer composition, the invention permits identification of a plurality of species from one sample using a universal primer set, rather than requiring multiple sets of probes corresponding to different microorganisms. The present invented method thus differs entirely from the prior art DNA probes described previously herein, each of which binds and detects primarily the DNA of a single species. A universal primer composition according to the invention binds to the DNA of most or all species having the given protein, but will then facilitate detection via amplification of internal species-specific sequences.

A further advantage of the universal primer composition is that, by analysis of a sufficient number of the individual amplified molecules, substantially all of the species present in the original sample will be detected and identified. Even organisms not present in the database will be detected, as a subpopulation whose signature sequence does not match any of those within the database. The person supervising the test need not make any guesses or assumptions as to which pathogens or organisms may be present in order to perform the analysis. Applicant is not aware of any other method which can provide such a comprehensive detection and identification. Furthermore, the identification of all the microorganisms is the product of essentially one step, which is the amplification of the signature sequences present in the original sample extract. Moreover, these results are obtained without any requirement for culturing of the sample.

BRIEF DESCRIPTION OF THE DRAWINGS

FIG. 2 shows the amino acid sequences of the conserved and variable segments 2, 4, 6 of type II DNA topoisomerase from FIG. 1 in various bacterial species (SEQ. ID Nos. 1–16 and 101, 102); two-letter abbreviations of names of individual species are shown in parentheses to the left of the sequences;

FIG. 3 shows the DNA sequences of an example of universal primers according to this invention (SEQ. ID Nos. 105, 106);

FIGS. 5A and 5B together show the amino acid sequences of a second set of conserved and variable regions (12, 14, 16, 18 in FIG. 1; (SEQ. ID Nos. 17–32 and 103–104) of type II DNA topoisomerases. The sequences extend from left in FIG. 5A to the right of FIG. 5B. Thus, to read through the entire sequences the right end of the sequences in 5A should be aligned at the left end of the sequences in 5B. Two-letter abbreviations of the individual species names are shown in parentheses on the left of both FIGS. 5A and 5B;

FIG. 8 is a diagram of the topoisomerase II segment shown in FIG. 2, showing specific or "nested" primer sequences regions; and FIGS. 9A and 9B together show the amino acid sequences of the conserved and variable regions of topoisomerase II of FIGS. 5A and 5B, indicating specific primer sequence regions.

DETAILED DESCRIPTION OF THE INVENTION

Figure 1:
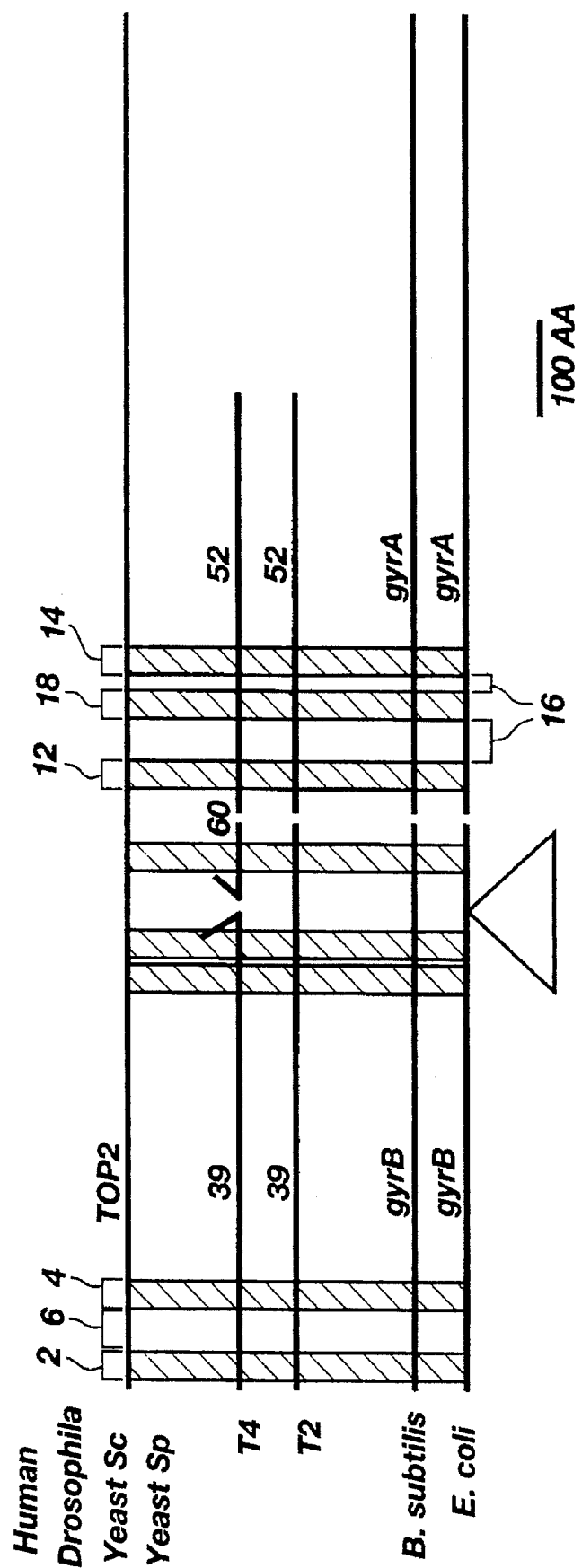
FIG. 1 is a schematic diagram representing the conserved and variable amino acid sequence regions of type II DNA topoisomerases.

A central aspect of the invention is the design of primers useful to amplify variable or signature sequences which distinguish among individual species. According to applicant's invention, a set of universal or of specific primers can be synthesized based upon any desired protein having both highly conserved and variable segments. However, applicant has found that in a preferred embodiment, the protein should meet certain criteria. First, for the broadest usefulness, the protein on which the primers are based should be ubiquitous or nearly so. Nevertheless, as mentioned previously herein for some applications a protein found primarily in selected groups of organisms may be used.

Secondly, it is desirable that the function of the protein in cellular metabolism be required for cell survival and/or reproduction, so that at least some segments of the protein (usually those actively engaged in performing that function) are likely to be very highly conserved.

Thirdly, the extent to which the protein is conserved across the phylum or species group whose identification is desired should be generally around 40% to 50%. In proteins which are too highly conserved, such as histories which are 70–75% conserved, it is difficult to find signature sequences which can distinguish among closely-related species. In less conserved proteins, such as RNA polymerase which is conserved by less than 30%, it may be difficult to find consensus sequences which are sufficiently similar over a wide range of species.

There are also certain criteria on which the selection of consensus sequences for a preferred embodiment is based. The consensus sequences should be very highly conserved, while the signature segments should be sufficiently variable among closely-related species to allow them to be differentiated. Applicant has furthermore found that in order to unequivocally identify the consensus sequences of the selected protein, it may be advantageous to compare the amino acid sequences from species spanning a broad evolutionary range (for example, from human to yeast to bacteria). This is because the protein sequences of species which are within a single genus, family or a phylum, will in addition to the consensus sequences common to all phyla, share a good deal of sequence homology elsewhere in the protein.

A protein meeting the criteria described in the preceding paragraphs is the type II DNA topoisomerase. Type II topoisomerases are enzymes which can change DNA topology via a concerted breakage and reunion activity involving both strands of the DNA duplex. Such an activity is absolutely required for DNA activities including replication and transcription. Consequently, type II topoisomerase is ubiquitous among free-living organisms, and is also found in some viruses. Across species, the amino acid sequence of the enzyme is conserved by about 30% to 50%. Certain consensus sequences are nearly identical in all species, while other variable segments differ substantially. Within a phylum, the amino acid sequence of type II topoisomerase is conserved by about 50%. Among microbes, the type II topoisomerase is about 50% conserved in amino acids.

The universal DNA primer composition exemplified herein is derived from DNA sequences coding for amino acid consensus sequences of type II topoisomerase which are immediately adjacent to variable signature regions of the same protein. These primers are oligonucleotides of about 15 to about 36 nucleotides in length. DNA extracted from the sample of organisms to be analyzed is subjected to a polymerase chain reaction (PCR) with a set of such universal primers. This results in amplification of DNA coding for signature sequences of substantially all DNA molecules represented in the mixture and having the flanking consensus sequences.

The DNA solution resulting after the PCR is then subjected to means for isolating a mixture of molecules having amplified signature coding sequences. Such molecules will be of approximately the length of the signature coding region plus the primer. Amplified sequences other than those of the signature coding region will not be of the correct size. The isolation can be performed by a variety of means as known in the art. Individual molecules comprising a representative sample of the mixture are then analyzed to determine their DNA sequences. Finally, in a preferred embodiment the DNA sequence of each such molecule is converted to its corresponding amino acid sequence, and compared to a database of amino acid signature sequences each corresponding to a particular species. When an amino acid sequence derived from a given molecule is found to match the sequence of a particular species in the database, this is diagnostic of the presence of that species in the original sample.

FIG. 1 is a schematic showing consensus sequences and adjacent variable segments of type II topoisomerase in species ranging from human to bacteria to viruses. Type II topoisomerase is also found in some vital species, notably the T4 and T2 bacterial phages. The shaded regions indicate consensus segments in which a constant sequence of at least five amino acids is found in all the species shown. The non-shaded areas indicate variable regions of the protein whose amino acid sequences differ considerably among species.

In theory, a single pair of primers, one from each flanking consensus sequence, can be used to amplify the signature sequence. However, a highly preferred embodiment includes a multiplicity of primers having sequences corresponding to potential alternate DNA sequences. As is well-known, the genetic code is degenerate, meaning that an individual amino acid may be coded for by as many as 6 different DNA codons (each codon consisting of three adjacent nucleotides). Thus, even though the amino acid sequence of a region of type II topoisomerase from different organisms may be identical, the DNA in those organisms which codes for the region may differ. The PCR technique requires a good match between the DNA primer sequences especially at the 3' end and the DNA to which it binds (Saiki et al.). Thus, to avoid failing to amplify species having such alternate DNA sequences, the set of primers should include variant primers having at least some of the alternate sequences.

Moreover, it is desirable that the amino acids in the consensus sequence be coded for by 3 or fewer different codons, especially in the portion immediately adjacent to the signature segment. Obviously, the presence of one or more amino acids having six possible codons drastically increases the number of possible DNA sequences. By choosing the consensus sequences to have amino acids with at most three possible codons (or in an even more preferred embodiment, two possible codons), the number of different oligonucleotide sequences required in the universal primers is kept manageable.

FIG. 1 also depicts the relationship of two subunits found in type II topoisomerases, termed gyrA and gyrB. Also, in some organisms the parC and parE gene products form a gyrase-like enzyme. In some organisms the parC and parE amino acid sequences are sufficiently homologous to the gyrA and gyrB subunits, respectively, to be useful in the invention.

Referring again to FIG. 1, reference numerals 2 and 4 identify consensus amino acid sequence segments of type II DNA topoisomerase, on which one set of universal primers according to the invention is based. According to the convention that the "left" end of a protein is the N-terminal end, and the "fight" end is the C-terminal end, segments 2 and 4 are on the left and fight flanks, respectively, of signature segment 6. Segments 2, 4, and 6 together comprise about 60 amino acids, corresponding to a DNA segment of about 180 nucleotides. The convention of the left N-terminal to fight C-terminal of a protein extends to the DNA, where only one strand of the duplex actually codes for the protein. The coding strand is by convention shown as the 5'→3' strand.

In FIG. 1, reference numerals 12 and 14 identify consensus sequence segments from which a second set of universal primers is derived. Segment 16 is the signature segment flanked by consensus segments 12 and 14. Segment 18 is a consensus segment embedded in the signature segment 16.

FIG. 2 is a comparative listing of the amino acid sequences of the region spanning consensus segments 2 and 4 and the intervening signature segment 6, for a range of bacterial species (SEQ. ID Nos. 1–16). Consensus sequence 2 (SEQ. ID No. 101) and consensus sequence 4 (SEQ. ID No. 102) are respectively the first 8 and last 7 residues of each of SEQ. ID Nos. 1–16. In FIG. 2, regions in which the amino acid sequence of a given species exactly matches that of the first species (*E. coli*) are deleted for clarity. It can be seen that in the signature segment 6 (SEQ. ID Nos. 1–16), there are a few amino acids at individual positions or in short segments which are conserved entirely across the species shown. However, there is substantial variation in the remainder of the amino acids in segment 6.

FIG. 3 shows the nucleotide sequences of a pair of DNA oligonucleotide primers 42 and 44 (SEQ. ID Nos. 105, 106) corresponding to amino acid SEQ. ID Nos. 101, 103 of the left and fight flank consensus segments 2 and 4, respectively, and useful for identification of bacteria. The basic nucleotide sequences 42 and 44 (SEQ. ID Nos. 105, 106) are shown in relation to the amino acid sequences (SEQ. ID Nos. 101, 102) for which they code. Possible substitute nucleotides are shown below certain nucleotide positions in sequences 42 and 44; the significance of these will be addressed in a subsequent paragraph. Primers 42 and 44 may be synthesized either individually or as a mixture by an oligonucleotide synthesizer. Such devices, which are commercially available from a number of sources, are capable of synthesizing either individual oligonucleotides or mixtures thereof having any desired base sequences.

In FIG. 3, it should be further noted that the 5' end of primer 42 (SEQ. ID No. 105) includes the sequence 43 of a cut site for the restriction enzyme KpnI. Sequence 43 does not derive directly from the amino acid sequence of consensus segment 2 (SEQ. ID No. 101), but has been added by the applicant because it enhances the cloning of the extended primers into the plasmid vector which is discussed hereinafter (see step 86 in FIG. 7).

Figure 4:
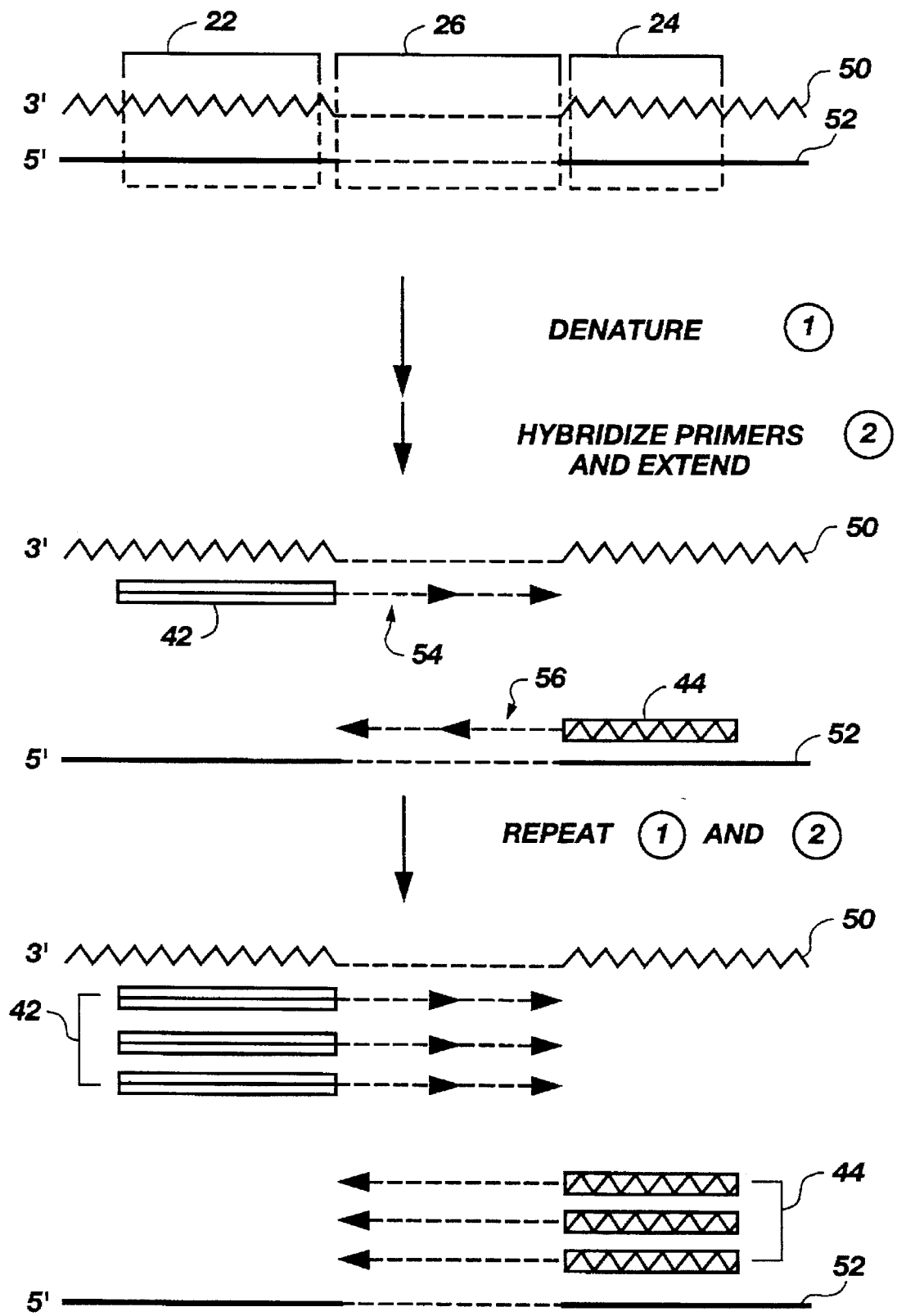
FIG. 4 illustrates a simple PCR as it might be performed with primers according to FIG. 3.

FIG. 4 illustrates in schematic form a PCR using the basic primers 42, 44 (SEQ. ID Nos. 105, 106) of FIG. 3. PCR requires at least two primers flanking the target sequence whose amplification is desired and of polarity such that extension of each primer by a DNA polymerase occurs only in the direction of the target sequence (Saiki et al. 1985). In FIG. 4, the two DNA strands of the parent helix are designated 50 and 52 as starting from 3' and 5' ends to the left, respectively, as shown. The DNA duplex regions corresponding to the left 2 and right 4 flanks and to signature region 6 (see FIG. 2) are designated 22, 24 and 26, respectively. Enzymatic extension of primers during PCR occurs from the 3' end in the 5'→3' direction. Therefore, the universal primer 42 (shown in FIG. 3) for the left flank matches the sequence of strand 52 and can thus selectively hybridize to the opposing strand 50. The 3' end will then be extended enzymatically to make a copy 54 of the signature region of strand 52, as shown in FIG. 4. Conversely, the primer 44 (shown in FIG. 3) for the fight flank matches the sequence of strand 50, can hybridize with strand 52, and can then be extended to make a copy 56 of the signature region of strand 50. Multiple cycles of denaturing, hybridizing, and extension produce a plurality of copies substantially equivalent to 54 and 56.

In FIG. 3, for some positions within the DNA sequences 42, 44 (SEQ. ID Nos. 105, 106) alternate nucleotides which will not change the amino acid sequence (due to degeneracy of the genetic code) are indicated below that position. In a highly preferred embodiment, the set of universal primers should include most or all of the possible DNA sequences coding for the consensus sequences. Thus, a complete set of universal primers for segments 2 and 4 would include sequences 42, 44 (SEQ. ID Nos. 105, 106) plus all the possible permutations thereof obtainable by varying the nucleotides at those positions according to the possible substitutions indicated in FIG. 3. For sequences 42 and 44, there are 192 and 8 such possible sequences, respectively. As is known, an oligonucleotide synthesizer can readily be programmed to produce all of the permuted primer variants along with the base sequences 42, 44 in the same synthesis. The relative amounts of the different permuted primers can also be partially controlled during the synthesis.

PCR requires an especially good match between the 3' end of the primer and the complementary sequence to which it binds. However, PCR will tolerate some mismatching at the 5' end of the primer. Thus, in some instances the set of universal primers may instead contain all possible permutations of nucleotides in the region within about 10 nucleotides of the 3' end, but only some of the possible permutations of the region near the 5' end. Ignoring some of the degeneracy at the 5' end of the primer will reduce the number of primer variants in the set, and in some cases this appears to enhance the amplification signal. Never-theless, in practice it has been found that satisfactory results are obtained with primer sets of over 1000 different primer variants.

Furthermore, it is recognized that in some applications it may be desirable to use a selected subset of the complete set of primers, rather than the complete set. For example, in a case where a predominant species present is already known, to improve the detection of other species it might be desirable to omit from the set of universal primers those sequences corresponding to the consensus sequences of the predominant species. Or, in a case such as analysis of soil microorganisms, the subset of primers might comprise mostly sequences derived from such soil microorganisms, and omit sequences found primarily in other classes of organisms.

FIGS. 5A and 5B together show the amino acid sequences spanning segments 12, 14, 16, and 18 for a range of organisms (SEQ. ID. Nos. 17–32). An alternate set of universal primers according to the invention may be derived from segments 12, 14 (SEQ. ID Nos. 103, 104). Segments 16 constitute the signature region. The presence of a third consensus sequence 18 embedded among segments 16 in the region between flanking segments 12 and 14 provides a control to verify that the copies produced by PCR amplification with the primers derived from 12 and 14 correspond to the desired intervening region. Verification can be accomplished either by sequencing the PCR products to establish that the sequence 18 is present in the amplified DNA, or by probing the products with a probe that selectively hybridizes to segment 18. Or, if sequence 18 includes suitable restriction enzyme cut sites, the amplified products can be cut with such enzymes and analyzed electrophoretically to determine whether fragment(s) of the expected size(s) are present, as known in the art.

Figure 6:
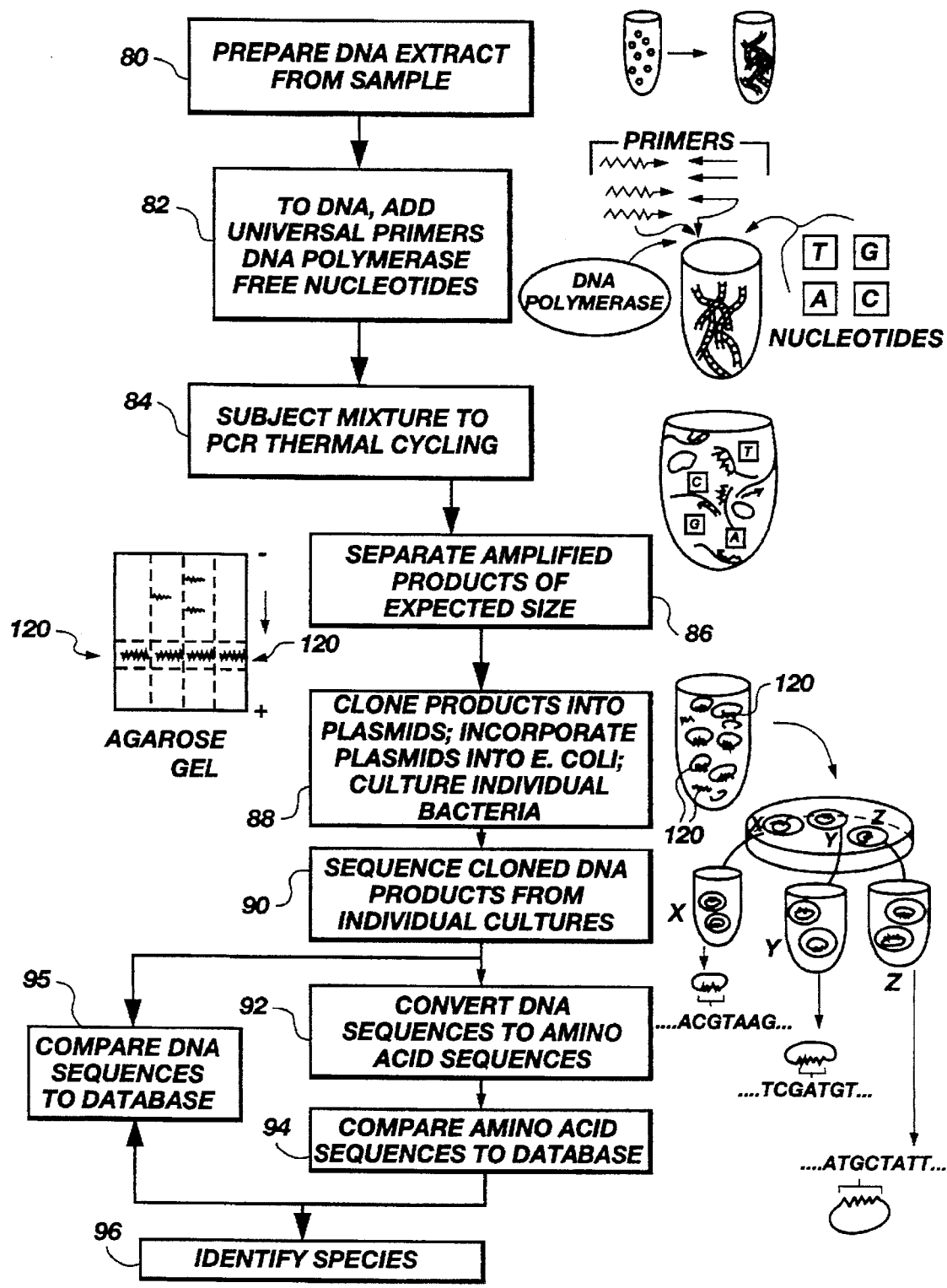
FIG. 6 is a schematic of the method of using the universal primers to identify species in a sample.

A diagrammatic outline of the current protocol for the use of the universal primers to identify microbes in a sample is shown in FIG. 6. In the first step 80, DNA may be extracted from the original sample according to conventional methods (see for example Current Protocols in Molecular Biology, eds. F. Ausubel et al., 1989, the contents of which are hereby incorporated by reference). The DNA need not be extensively purified, but simply made accessible for hybridization and enzymatic extension of the universal primers. At present, a relatively crude extract of the DNA is made by lysing the cells with lysozyme and detergent such as SDS (sodium dodecyl sulfate) or its equivalents, followed by removal of carbohydrates. The latter step may be accomplished using precipitation with CTAB, another detergent. It will be recognized by those in the art that many alternative extraction procedures may also yield adequate DNA samples.

In the second step 82, the universal primers are mixed with the nucleic acid extract of 80, along with a DNA polymerase and free nucleotides which the polymerase can use to extend the primers. Generally, it is preferred to use a Taq I DNA polymerase because of its stability to the temperatures required to denature the DNA duplex to single strands. In step 84, the mixture is subjected to thermal cycling as known for PCR (Saiki et al., Science. 1985). Briefly, the mixture is heated to temperatures sufficient to denature the duplex, then cooled to promote hybridization of the primers to the single strands. Incubation of the mixture is continued under conditions which promote enzymatic extension of the primers by the DNA polymerase. After an incubation time approximately sufficient for the primers to be extended through the intervening signature region, the mixture is again heat denatured to single strands, re-hybridized, and undergoes enzymatic extension to make copies of the intervening signature region. By repeating these cycles, selective amplification of up to 1,000,000-fold of the region between the primers can be achieved. At present, PCR is now generally performed with automated thermal cycling machines commercially available for the purpose.

Figure 7:
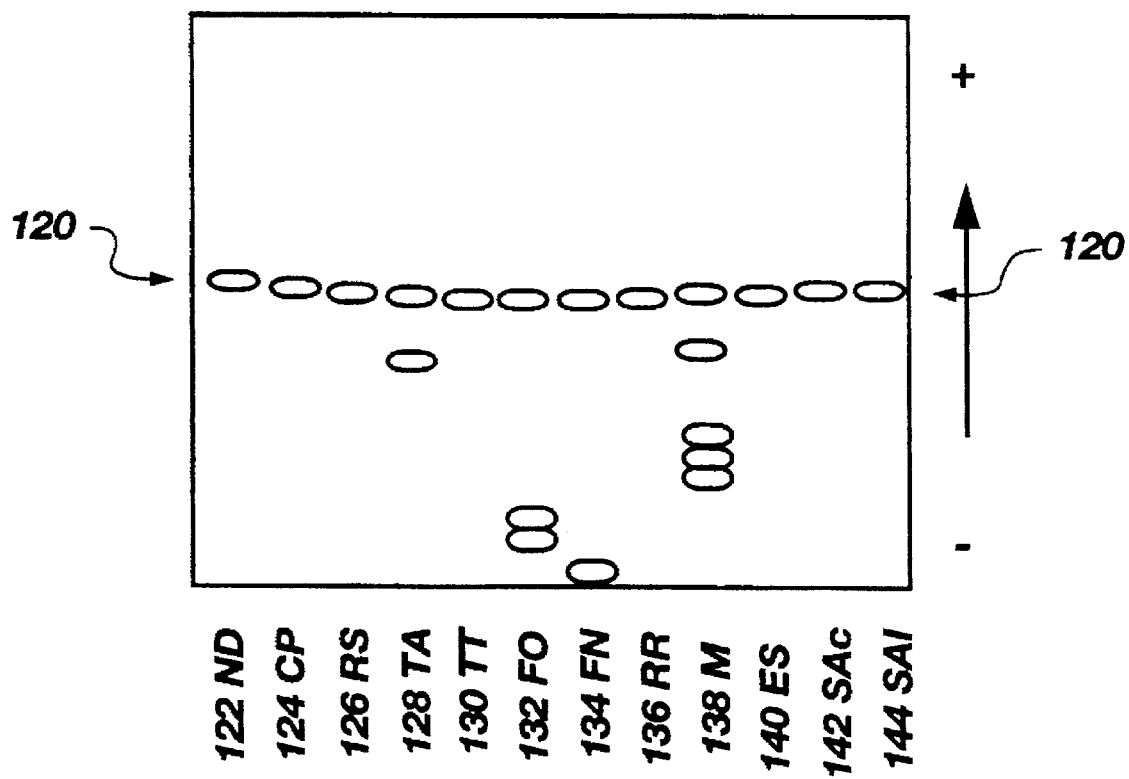
FIG. 7 displays a gel electrophoretic separation of amplified products obtained in step 86 of FIG. 7, using the set of primers shown in FIG. 3.

After the PCR reaction is terminated, amplified DNA products of the size expected from the signature region are separated from the reaction mixture (Step 86). A wellknown and convenient means for accomplishing this is to electrophorese the mixture on an agarose gel and cut the bands corresponding to the desired DNA size from the gel. FIG. 7 is an example of such a gel, showing bands 120 which contain amplified sequences produced from the primers of FIG. 3. Lanes 122, 124, 126, 128, 130, 132, 134, 136, 138, 140, 142 and 144 represent samples each containing a different individual bacterial species. The DNA in the band is then separated from the agarose. A preferred method involves the use of a low-melt agarose in the gel, from which the DNA is readily purified as known in the art. However, it will be recognized by those in the art that any other means for separating DNA molecules according to size, not only electrophoresis, can be used in step 86.

The amplified DNA obtained from the bands 120 is then incorporated (step 88) into a plurality of copies of a plasmid vector that can be grown in E. coli. The plasmid vectors are transferred into a sample of E. coli by wellknown methods. Individual bacteria carrying different incorporated sequences are separately cultured to produce quantities of plasmid sufficient for DNA sequencing. As presently known in the art, approximately 3–5 µg of plasmid DNA is generally adequate for sequencing. Once a sufficient amount of the cloned plasmid DNA is available, the inserted PCR product is sequenced using standard methods (step 90). The sequencing is done with the help of an automatic sequencer of the type currently available from Applied Biosystems or duPont.

Preferably, as many steps as possible will be performed by automated means, including synthesis of universal primers, PCR, and sequencing of the amplified DNA. The vector used by the applicant is herein referred to as pT7-5B, which is a derivative of pT7-5. pT7-5 is in turn derived from pBR322 by inclusion of the T7 bacteriophage promoter Ø10. pT7-5B was slightly modified by the applicant to incorporate DNA linker sequences providing the following restriction cut sites: BglII, SphI, or KpnI. These linkers are added solely to facilitate cloning, as will be known to those in the art (see for example Current Protocols in Molecular Biology, ed. Ausubel, ibid, and A Manual of DNA Cloning by T. Maniatis, the contents of which are incorporated by reference).

It will be recognized by those in the art that many other vectors could be used for the cloning. Also, the choice of restriction enzyme cut sequences added to pT7-5B is based largely on convenience, and many other restriction enzyme linkers could be used.

The sequence of the DNA coding for the signature region may then be convened (step 92) to its corresponding amino acid sequence, which is then compared to reference signature sequences from different organisms compiled in a database (step 94). The conversion of the signature DNA sequences to amino acid sequences, and matching of the amino acid sequences to the database, can be performed by many small personal computer-type devices. When the sequence of a cloned amplified product matches one of the reference sequences, that is indicative of the presence of the species having that reference sequence in the original sample (step 96).

Alternatively, the DNA sequence may be directly compared to a DNA sequence database (step 95). Circumstances in which this procedure is especially desirable are discussed herein elsewhere.

A database of either DNA or amino acid reference signature sequences for any desired group of species may be compiled by performing steps 80 through 90 (or 92) on reference samples known to contain only one species. Thus, it is not necessary to sequence the protein homologues, but only to use DNA-based procedures. However, it is also possible to obtain amino acid sequences for the database by sequencing the proteins or from literature reports where available, or by any other means known in the art.

The probability of identifying any particular species in the sample will obviously depend largely on two factors: first, how prevalent the species is relative to other species in the sample, and second, how many individual molecules from the amplified mixture are sequenced. If only one species is present in the sample, then in theory from one to three cloned sequences could provide unequivocal identification of the organism in the sample. However, in practice a representative number of individual molecules will be sequenced. This representative number can be chosen to fit the circumstances, the expected complexity of the sample, and/or the desired level of certainty of detection, according to well-established statistical principles.

In practice it has been found that when replicate independent PCR reactions are performed on DNA from a single reference sample, and as many as 10 individual amplified products from those PCRs are sequenced, the signature sequences obtained from all of the sequenced products are identical. Such results illustrate the repeatability and accuracy of the method.

The following examples are applications of the invented method leading to the discovery of "unknown" or "unexpected" microorganisms in test samples.

EXAMPLE 1

In the course of examining the type II topoisomerase signature sequence for Rhodobacter capsulata, a supposedly homogeneous culture was used. One ng of extracted DNA from culture was mixed with 1.2 ng and 0.54 ng of the primers shown in FIG. 3. The PCR reaction was performed in a volume of 100 µl for 32 cycles. Each cycle consisted of alternating temperatures of 94° C., 54° C. and 72° C. for one minute, two minutes and 3 minutes respectively, and the reaction was done in a thermal cycler (Cetus Corp.). The PCR products were analyzed on a 3% low melt agarose gel, and the band corresponding to approximately 180 base pairs in length was cut from the gel and purified. The purified DNA fragment was cloned into the E. coli plasmid vector pT7-5B via KpnI and SmaI sites. Four clones having the PCR product as inserts were selected randomly for DNA sequencing. The DNA sequence and the derived amino acid sequence revealed two types of signature sequences matching those of Rhodobacter capsulata. A third type of sequence, found to match that of Pseudomonas aeruginosa, was also detected. This result suggested that the original culture was a mixed culture of R. capsulata contaminated with P. aeruginosa. Such a finding is consistent with the fact

13 that these two species are known to grow under similar conditions and are often found growing together.

EXAMPLE 2

The microbial-like type II topoisomerase signature sequence of corn was examined. Plant DNAs are expected to encode multiple topoisomerases. Topoisomerases from plant mitochondria and chloroplasts are thought to be microbial in evolutionary origin. Therefore, they are detectable using the universal primers selected for microorganisms. The signature sequence 16 was examined using universal primers based on segments 12 and 14 (FIG. 1). One μg of total DNA from a corn plant was used in a PCR reaction under conditions and experimental protocols identical to those described in Example 1. An amplified DNA fragment of approximately 450 base pairs in length was generated, which is the size expected from the amino acid signature sequence of this region of the type II topoisomerase. The fragment was excised from the gel, purified and cloned into the E. coli plasmid vector pT7-5B via the KpnI and HindIII sites. Five randomly selected clones carrying the expected PCR products as inserts in their plasmids were processed and the plasmid DNA was sequenced. Comparison of the DNA and the derived amino acid sequences of the plant sample with the existing database revealed that two Pseudomonas and one E. coli-like sequences were present. These results suggested that the corn plant was contaminated with these two microbes, possibly on the outside of the plant leaves. As the database of type II topoisomerase signature sequences of microbes is enlarged, more unexpected microbial contamination may be revealed.

At present, DNA sample analysis according to this invented method requires approximately four to five days in the hands of an experienced technical staff. However, it is envisioned that with the advent of improved automation in instrumentation in PCR and DNA sequencing methodology, and the possible integration of these machines into a work station, the entire procedure may be performed by nonspecialists and in much less time resulting in unequivocal DNA-based identifications of microbial species.

FIGS. 2 and 5 show 32 amino acid sequences for signature segment regions 6 and 16 in 21 different species including bacteria, fungi and human. The signature sequences are specific enough to distinguish among microbial species. A species may also be represented by more than one amino acid sequence in the same signature region. Two such cases have been already found: Borrelia burgdorferi and Neisseria gonorrhea are each represented by at least two alternate sequences in a signature region of type II topoisomerase. In FIGS. 5A and 5B, the two known alternate amino acid sequences are designated NGa and NGb (SEQ. ID Nos. 22, 23) for N. gonorrhea, and BBa and BBb (SEQ. IF Nos. 25, 26) for B. burgdorferi, respectively.

The simpler form of analysis, to which the preceding portion has largely referred, is to compare the amino acid sequences derived from the amplified DNA sequences to a database of amino acid signature sequences. This is because the degeneracy of the DNA genetic codon system may result in several to hundreds of DNA sequences coding for one amino acid sequence. However, an alternate procedure is to match the DNA sequences of the signature coding region against a suitable DNA sequence database. In some applications it may be particularly desirable to use the DNA sequences themselves as an identification tool. For example, populations of microbes from different geographic regions may have the same amino acid sequence, but different DNA coding sequences. Such variations in the DNA sequence may be called "silent mutations", because the protein is unchanged. As is known in the art, geographical subpopulations may have different individual silent mutations. With an appropriate DNA sequence database, such subpopulations could be distinguished by their DNA signature sequences.

SEQ. ID Nos. 33–100 are nucleotide sequences spanning the consensus and signature segments 2, 4, 6 (gyrB or parE subunits) and 12, 14, 16, 18 (gyrA or parC subunits) for 39 species of microbes of clinical relevance. For some organisms, the sequences of several different subunits are presented. The sequence listing specifies the subunit from which it is derived for each sequence. The parC and parE sequences share the consensus regions of gyrA and gyrB, respectively. Thus, universal primer compositions useful to amplify gyrA and gyrB unique sequences, are also useful to amplify parC and parE sequences.

The method may also be applied to identification of subspecies or subpopulations of the same species from different geographic locations which show some genetic divergence (see for example Suzuki and Griffiths, An introduction to genetic analysis, Chapter 14, W. H. Freeman and Co., 1976). Such geographical subpopulations may be identifiable by different amino acid sequences in the signature region. In the current database, two organisms, Neisseria gonorrhea (the pathogen of gonorrhea) and Borrelia burgdorferi (the pathogen of Lyme disease), have so far been found to be represented by more than one amino acid signature sequence in the same region (FIGS. 5A and 5B).

It will be recognized that universal primers such as the compositions described herein can be constructed for any ubiquitous protein having substantially conserved segments adjacent to variable segments. Depending upon the desired application, gene products other than type II topoisomerase might be preferable. Examples of proteins of potential use according to this invention include RNA polymerase and other DNA binding proteins. Where it is desired only to distinguish among very closely related species, a protein common only to such species may be used. An example of such a protein to which the invention might be applied is a rickettsial antigen, whose DNA sequence analysis in four related species is discussed in Anderson and Tzianabos (J. Bacteriol. 171:5199–5201, 1989).

It is further recognized that universal primers constructed on the principles of the invention can also be applied to identification of species from DNA sequences which are non-coding, such as "satellite" sequences, or which code for conserved RNAs, such as ribosomal RNA or transfer RNA. All that is required is that the DNA sequence be found in a wide range of species and that it have a variable region closely flanked by highly conserved regions.

An example of such a DNA sequence is the 16S ribosomal DNA. As shown by Giovannoni et al. and Ward et al. (Nature, May 1990, v. 345 pp. 60–63 and 63–65, respectively), 16S rDNA in at least some microbial species contains variable sequence regions which can be amplified by PCR with piers based upon highly conserved consensus regions, and that these variable regions are useful to detect previously unknown species and in phylogenetic analysis. Notably, neither of these two references mentions using variable sequences recovered by amplification as a tool to identify simultaneously all species in a mixed sample.

It will further be recognized that instead of amplifying the deoxyribonucleic acid segment, the invention could equivalently be performed by amplifying an RNA or ribonucleic acid transcript of the DNA segment. Normally RNA amplification entails copying of cDNAs, then applying PCR in the usual manner to amplify the cDNA copies. The primer compositions disclosed herein would be equally useful for amplification from cDNA, since the sequences are all drawn from coding regions.

At present the database disclosed herein includes SEQ ID Nos. 1–32, which are amino acid sequences of the conserved plus signature regions for 32 type II topoisomerases of 24 species; and SEQ ID Nos. 33–100 and 107–195, which are the nucleotide sequences for 97 species. All of these sequences were obtained using the universal primers of the invention, and the signature region of each individual species is sufficiently unique to permit precise species identification by comparison of the sequence to the database.

An amino acid sequence (polypeptide sequence) database according to the invention and based on Type II topoisomerase, could include all of SEQ ID Nos. 1–32 plus more amino acid sequences derived from the corresponding regions of GyrA, GyrB, ParC and/or ParE subunits found in other organisms. A DNA sequence database according to the invention, and based on Type II topoisomerase, could include all of SEQ ID Nos. 33–100 and 107–195, plus more DNA sequences derived from the corresponding regions of GyrA, GyrB, ParC and/or ParE subunits found in other organisms.

Figure 9B:
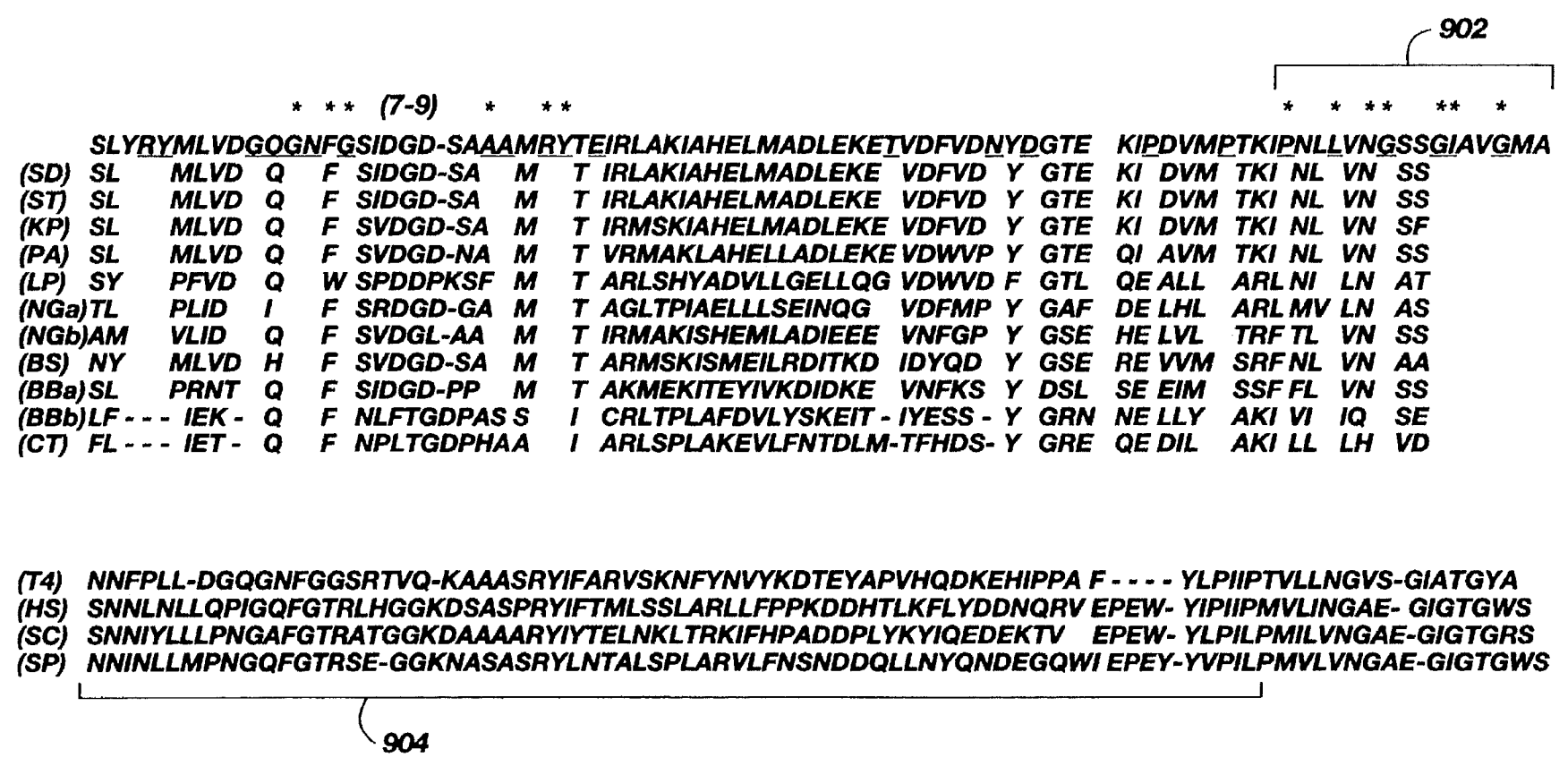

In another embodiment which is useful for specifically distinguishing among closely related species or identifying a particular species of interest, the invention provides a specific primer composition based on "nested" primers having sequences derived from the signature sequence region internal to, that is between, the consensus regions (FIGS. 8, 9A, 9B). As seen in FIG. 8, regions 800, 802 are consensus regions of the type II topoisomerase identified as gyrA. Region 804 is the signature region intervening between the fling consensus regions 800, 802. Regions 806, 808 are hypothetical examples of specific primer regions, within the signature region 804 and nested within the consensus regions, illustrating the general manner in which sequences for specific primer pairs are derived. The "nested" or specific primer composition is thus constructed to selectively amplify an internal portion of the signature region of one or a few species. It should be noted that sequences for the specific primer pair need not abut directly against the consensus sequences, but may be drawn from anywhere within the signature region to amplify a portion thereof. The specific primer sequence is obtained from the nucleotide sequence to provide specificity, as closely related species may have the same amino acid sequence while differing in nucleotide sequence. In FIGS. 9A and 9B, region 904 is that from which specific primers for gyrB can be derived. It will be apparent that the conditions for hybridization used with the specific primers should be of appropriate stringency to prevent significant hybridization to sequences differing in one or small number of nucleotides.

A specific primer composition will usually contain only one or a few primer pair(s), sufficient to provide for degeneracy in signature nucleic acid sequence which do not alter the amino acid residue sequence. However, optionally two or more specific primer compositions may be used. As an example, two specific primer compositions from different topoisomerase II isozymes (e.g. one each from parC and parE, or from gyrA and gyrB) in a single species, could be combined. Or, a specific primer pair A derived from one topo II region, for example gyrA, and designed to be specific for organism A, could be combined with a second specific primer pair B which is specific for gyrB of organism B. A differential test could include a primer set A which is so designed as to amplify the signature segment of both organisms A and B, while the second primer set B is specific for only organism B.

The presence of the particular specie(s) may be diagnosed in the amplified extract as the presence of a sufficient quantity of amplified nucleic acid segments of length corresponding to the signature region amplified by the specific primer composition. Alternatively or additionally, the amplified segment can be sequenced and matched against a database as described for the method of using the universal primer composition.

In a presently highly preferred embodiment of the method using the specific primers, the sample extract is first subjected to amplification with an appropriate universal primer set (selected to amplify the signature region from which the specific primer composition is drawn). A second step of amplification is then performed using a specific primer composition. The specifically-amplified segments can be distinguished from the universally-amplified segments on the basis of size, since the former will lack the consensus portions and will thus be shorter by at least about 30 to 80 nucleotides.

SEQ ID Nos. 196–197 comprise a primer pair useful to specifically identify the presence of *Salmonella typhimurium*. SEQ ID Nos. 198–199 comprise a primer pair useful to specifically identify *Listeria monocytogenese*. SEQ ID Nos. 200–201 comprise a primer pair useful to specifically identify *Chlamydia trachomatis*. SEQ ID Nos. 202–203 comprise a primer pair useful to specifically identify *Actinomyces israelii*. SEQ ID Nos. 204–205 comprise a primer pair useful to specifically identify *Borrelia burgdorferii*. SEQ ID Nos. 206–207 comprise a primer pair useful to specifically identify *Thermotoga maritima*. From examination of these primer pairs together with other sequences in the database, it will be apparent how a specific primer pair for any species can be designed by the methods disclosed herein and using a database constructed as disclosed herein.

What is claimed is:

1. A method of selectively amplifying DNA segments of one or more species of organisms in a sample, comprising the steps of:

providing a database containing a plurality of reference sequences each comprising a subunit sequence of a selected signature region of a macromolecule selected from the group consisting of: type II topoisomerase enzymes and homologues of type II topoisomerase enzymes; each of the reference sequences being specific to a different individual species of a chosen group, and the selected macromolecule further having first and second conserved regions adjacently flanking the selected signature region;

providing a universal primer composition comprising a primer pair constructed to bind to a DNA encoding the macromolecule;

making an extract of DNA molecules from a sample; and using the primer composition to selectively amplify DNA segments of the signature region in the extract to produce amplified DNA segments.

2. The method of claim 1, wherein said universal primer composition is constructed to bind to third and fourth DNA regions which respectively encode third and fourth portions of the signature region, the third and fourth portions being located between the first and second conserved regions.

3. The method of claim 2, further including the steps of:
providing a consensus primer composition comprising primers constructed to bind to first and second DNA flanking regions which respectively encode the first and second conserved regions; and
amplifying the extract with the consensus primer composition prior to said step of amplifying with the primer pair.

4. The method of claim 2, wherein the primer pair has sequences selected to amplify a region selected from the group consisting of: region 810 in FIG. 8; and region 910 in FIGS. 9A–9B.

5. The method of claim 4, wherein the specific primer composition is selected from the group consisting of the following primer pairs: SEQ ID Nos. 196–197, SEQ ID Nos. 198–199, SEQ ID Nos. 200–201, SEQ ID Nos. 202–203, SEQ ID Nos. 204–205, and SEQ ID Nos. 206–207; and wherein the specific primer composition may further include additional primer pairs changed from the selected primer pair by a nucleotide substitution which does not change the coded residue sequence.

6. The method of claim 2, wherein the primer pair is constructed to amplify a segment encompassed within a sequence selected from the group consisting of: SEQ IDs Nos. 33–100 and 107–195.

7. The method of claim 2, wherein the universal primer composition includes a combination of two or more specific primer pairs derived from the signature regions of different species.

8. The method of claim 2, wherein said step of providing the database includes providing the respective variable portions denoted by numerals 6 and 16 of the sequences depicted in FIGS. 2, 5A and 5B (SEQ ID Nos. 1–32).

9. The method of claim 2, wherein the group may include any of the following species: bacterial species, plant species, fungal species, and protozoan species.

10. The method of claim 2, wherein the database includes SEQ ID Nos. 1–100 and 107–195.

11. The method of claim 3, wherein said step of providing a consensus primer composition comprises providing a plurality of DNA primers having different sequences which are selected to operably bind to alternate DNA segments coding for the conserved regions flanking the subunit sequence.

12. The method of claim 3, further including the steps of:
determining a residue sequence of at least one individual segment selected from the DNA segments amplified with the first and second primers; and
comparing the residue sequence with a reference signature sequence of the macromolecule derived from a known species to thereby diagnose the presence in the sample of the known species.

13. The method of claim 12, wherein said steps of determining a residue sequence and comparing the residue sequence are performed for each of a plurality of individual DNA segments, thereby identifying a plurality of organisms present in the sample.

14. The method of claim 12, wherein the residue sequence and the reference sequences are nucleotide sequences.

15. The method of claim 12, further including a step of converting the determined residue sequence to an amino acid sequence and wherein the database further includes reference amino acid sequences.

16. A method of identifying an organism in a sample, comprising the steps of:
providing a specific nested primer composition for amplifying a segment of a nucleic acid encoding a protein selected from the group consisting of: type II topoisomerase enzymes and homologues of type II topoisomerase enzymes; the protein having a signature region having an amino acid sequence which differs among different species, the signature region further being flanked by consensus regions whose amino acid sequence does not substantially vary among different species; and the primer composition comprising a primer pair constructed to amplify a signature segment encompassed within the signature region;
making an extract of DNA molecules from a sample;
using the specific primer composition to selectively amplify the signature DNA region, to produce amplified DNA segments; and
determining from the amplified DNA segments whether a particular specie(s) corresponding to the primer pair signature segment is present in the sample.

17. The method of claim 16, which further includes the steps of:
providing a consensus primer composition comprising at least first and second primers constructed to bind to a DNA encoding the macromolecule in respective first and second DNA flanking regions which respectively encode the first and second conserved regions; and
subjecting said extract to amplification using the consensus primer composition to produce a plurality of amplified signature segments each spanning the signature region, said step of subjecting to consensus amplification being performed prior to said step of amplification with the specific primer composition.

18. The method of claim 16, wherein the specific primer composition has a sequence coding for regions selected from the group consisting of: regions 806 and shown in FIG. 8; and regions 906 and 908 in FIGS. 9A–9B.

19. The method of claim 16, wherein the specific primer composition is selected from the group consisting of the following primer pairs: SEQ ID Nos. 196–197, SEQ ID Nos. 198–199, SEQ ID Nos. 200–201, SEQ ID Nos. 202–203, SEQ ID Nos. 204–205, and SEQ ID Nos. 206–207; and wherein the specific primer composition may include additional primer pairs changed from the selected primer pair by a nucleotide substitution which does not change the coded residue sequence.

20. The method of claim 16, further including a step of providing additional specific primer compositions, wherein the amplification step is performed using a combination of two or more specific primer compositions specific for different organisms.

21. The method of claim 16, wherein the organism is selected from the group consisting of: bacterial species, plant species, fungal species, and protozoan species.

22. The method of claim 16, wherein the organism is a bacterial species.

23. The method of claim 16, wherein the specific primer composition is constructed to amplify a segment encompassed within a sequence selected from the group consisting of: SEQ IDs Nos. 1–100 and 107–195.

24. The method of claim 17, wherein the consensus primer composition comprises a plurality of primer pairs selected from SEQ ID Nos. 105 and 106 and sequences substantially similar to these according to FIG. 3.

25. The method of claim 17, which further includes a step of providing a database of reference sequences, wherein the reference sequences include sequences selected from the group consisting of SEQ ID Nos. 1–100 and 107–195.

26. A method of using a database to identify at least one species of organism in a sample, comprising the steps of:

providing a database including reference amino acid sequences and further containing one or more reference nucleotide sequences each comprising a residue nucleotide sequence of a signature region found in a type II DNA topoisomerase, the signature zone having a defined length which is similar in all species of a chosen group and varies significantly in residue nucleotide sequence among species in the chosen group, the signature region further being flanked by left and right consensus regions having respective residue nucleotide sequences which do not vary significantly among the species, said database further providing the respective variable portions denoted by numerals 6 and 16 of the sequences depicted in FIGS. 2, 5A and 5B (SEQ. ID Nos. 1–32);

obtaining one or more nucleic acid segments from the sample, each said segment(s) derived from the signature region;

determining a residue nucleotide sequence of at least one of the segment(s);

converting the determined residue nucleotide sequence to an amino acid sequence; and comparing the converted amino acid sequence with said one or more reference amino acid sequences in the database to find a matching reference amino acid sequence, and thereby identify the sample organism.

27. The method of claim 26, wherein the sample organism is selected from the group consisting of plant species, fungal species and protozoan species.

28. A method of using a database to identify at least one species of organism in a sample, comprising the steps of:

providing a database including SEQ. ID Nos. 33–100, said database further containing one or more reference nucleotide sequences each comprising a residue nucleotide sequence of a signature region found in a type II DNA topoisomerase, the signature zone having a defined length which is similar in all species of a chosen group and varies significantly in residue nucleotide sequence among species in the chosen group, the signature region further being flanked by left and right consensus regions having respective residue nucleotide sequences which do not vary significantly among the species;

obtaining one or more nucleic acid segments from the sample, each said segment derived from the signature region;

determining a residue nucleotide sequence of at least one of the segments; and comparing the determined residue nucleotide sequence with said one or more reference nucleotide sequences in the database to find a matching reference nucleotide sequence, and thereby identify the sample organism.

29. A method of identifying one or more species of organisms in a sample, comprising the steps of:

providing a database including SEQ. ID Nos. 33–100, the database further containing a plurality of reference sequences each comprising a subunit sequence of a selected signature region of a macromolecule selected from the group consisting of type II topoisomerase enzymes and homologues of type II topoisomerase enzymes; each of the reference sequences being specific to a different individual species of a chosen group, and the selected macromolecule further having first and second conserved regions adjacently flanking the selected signature region;

providing a primer composition comprising at least first and second primers constructed to bind to a DNA encoding the macromolecule in respective first and second DNA flanking regions which respectively encode the first and second conserved regions; making an extract of DNA molecules from a sample;

selectively amplifying desired DNA segments in the extract using the primer composition to produce amplified DNA segments;

determining one or more nucleotide sequences of individual segments selected from the amplified DNA segments; and comparing the nucleotide sequences to the database to match the nucleotide sequences with reference sequences of the macromolecule derived from known species to thereby diagnose the presence in the sample of the known species.

30. The method of claim 29, wherein said steps of determining nucleotide sequences and comparing the nucleotide sequences are performed for a plurality of the amplified DNA segments.

31. The method of claim 29, wherein the subunit sequence is an amino acid sequence, and said step of comparing the nucleotide sequences further includes decoding the nucleotide sequences to signature amino acid sequences and comparing the signature amino acid sequences to the reference sequences.

32. The method of claim 29, wherein said steps of determining a nucleotide sequence and comparing the nucleotide sequence are performed for each of a plurality of individual the DNA segments, thereby identifying a plurality of organisms present in the sample.

33. The method of claim 29, wherein the macromolecule is further selected to have an internal conserved segment embedded within the signature sequence.

34. A method of identifying one or more species of organisms in a single sample, comprising the steps of:

extracting DNA from a sample to produce an extract containing a plurality of DNA molecules encoding a type II topoisomerase;

providing a primer composition comprising at least a pair of DNA primers constructed such that one member of the pair binds respectively to each of two DNA sequences coding respectively for two flanking consensus zones which flank a unique segment of the type II topoisomerase, the unique segment being different among different species and the consensus zones being substantially conserved among different species;

selectively amplifying a region containing the unique segment of the DNA molecules in the extract using the primer composition to produce a plurality of amplified nucleic acid segments;

determining one or more DNA sequences corresponding to the amplified unique segments; and comparing the determined DNA sequences to a database of reference sequences reflective of the variable zone of the topoisomerase II, each of the reference sequences indicative of a different species in a group of organisms, to identify one or more organisms present in the sample, said database including SEQ. ID Nos. 33–100.

35. The method of claim 34, wherein said steps of determining DNA sequences and comparing said determined sequences are performed for a plurality of the amplified nucleic acid segments.

36. The method of claim 35, wherein said step of selectively amplifying comprises the steps of:

providing at least one pair of primers useful to amplify the selected DNA segment by the technique of polymerase chain reaction; and incubating the primers with the DNA extract and other necessary reagents for synthesis of DNA molecules under PCR amplification conditions to produce the selectively amplified segments.

37. A method of identifying one or more species of organisms in a single sample, comprising the steps of:

extracting DNA from a sample to produce an extract containing a plurality of DNA molecules encoding a type II topoisomerase;

providing a primer composition comprising at least a pair of DNA primers constructed such that one member of the pair binds respectively to each of two DNA sequences coding respectively for two flanking consensus zones which flank a unique segment of the type II topoisomerase, the unique segment being different among different species and the consensus zones being substantially conserved among different species, wherein the primer composition includes a plurality of primer pairs selected from the group consisting of SEQ. ID Nos. 105 and 106 and sequences differing from SEQ. IDs No. 105 or No. 106 by one or more of the potential substitutions shown in FIG. 3;

selectively amplifying a region containing the unique segment of the DNA molecules in the extract using the primer composition to produce a plurality of amplified nucleic acid segments;

determining one or more DNA sequences corresponding to the amplified unique segments; and comparing the determined DNA sequences to a database of reference sequences reflective of the variable zone of the topoisomerase II, each of the reference sequences indicative of a different species in a group of organisms, to identify one or more organisms present in the sample.

38. A method of constructing a database of signature sequences of a single protein useful to identify organisms in a sample, comprising:

a first step of making an extract of DNA from a sample containing DNA from a single known species, and including a DNA molecule coding for a type II DNA topoisomerase;

a second step of amplifying DNA segments each encoding a selected region of the type II DNA topoisomerase, the selected region comprising a signature region having an amino acid sequence which varies among species in a group, an upstream conserved region and a downstream conserved region, said upstream and downstream conserved regions having amino acid sequences which are substantially conserved among species in a group;

a third step of determining the individual DNA sequence of at least one of the amplified DNA segments;

a fourth step of storing data reflective of the determined individual DNA sequence in a database, said database including sequences of region 6 shown in FIG. 2 and sequences of regions 16 and 18 shown in FIGS. 5A and 5B;

a fifth step of converting the individual DNA sequence to an encoded amino acid sequence; and a sixth step of repeating said first through fifth steps for a plurality of samples each containing a different single individual species and of storing the encoded amino acid sequence in the database.

39. The method of claim 38, wherein the species are bacterial species.

40. The method of claim 38, wherein the species are selected from the group consisting of fungal species, plant species and protozoan species.

41. A method of constructing a database of signature sequences of a single protein useful to identify organisms in a sample, comprising:

a first step of making an extract of DNA from a sample containing DNA from a single known species, and including a DNA molecule coding for a type II DNA topoisomerase;

a second step of amplifying DNA segments each encoding a selected region of the type II DNA topoisomerase, the selected region comprising a signature region having an amino acid sequence which varies among species in a group, an upstream conserved region and a downstream conserved region, said upstream and downstream conserved regions having amino acid sequences which are substantially conserved among species in a group, said step of amplifying DNA segments including the step of providing a DNA primer composition which contains at least one pair of primers having one member of the pair encoding the upstream conserved region and the other member encoding an antisense translation of the downstream conserved region, wherein the primer composition includes primers at least one of the DNA sequences selected from the group consisting of: SEQ. ID No. 105, SEQ. ID No. 106, sequences coding for SEQ. ID No. 103, sequences complementary to a sequence coding for SEQ. ID No. 104;

a third step of determining the individual DNA sequence of at least one of the amplified DNA segments;

a fourth step of storing data reflective of the determined individual DNA sequence in a database; and a fifth step of repeating said first through fourth steps for a plurality of samples each containing a different single individual species.

42. A composition of matter comprising at least two single-stranded DNA primers capable of selective hybridization to amplify an intervening signature segment of a type II topoisomerase, said signature segment being selected from the group consisting of segment 6 of FIG. 2, and segments 16 and 18 of FIGS. 5A and 5B.

43. The composition of claim 42, which includes primers having at least one of the DNA sequences selected from the group consisting of SEQ. ID No. 105, SEQ. ID No. 106, sequences coding for SEQ. ID No. 103, and sequences complementary to a sequence coding for SEQ. ID No. 104.

* * * * *

SEQUENCE LISTING ( 1 ) GENERAL INFORMATION:

( i i i ) NUMBER OF SEQUENCES: 207

( 2 ) INFORMATION FOR SEQ ID NO:1:

( i ) SEQUENCE CHARACTERISTICS:
        ( A ) LENGTH: 59 amino acids (B) TYPE: amino acid
(C) STRANDEDNESS:
(D) TOPOLOGY: Not Relevant (ii) MOLECULE TYPE: protein (iii) HYPOTHETICAL: NO (iv) ANTI-SENSE: NO (v) FRAGMENT TYPE: internal (vi) ORIGINAL SOURCE:
(A) ORGANISM: Escherichia coli (xi) SEQUENCE DESCRIPTION: SEQ ID NO:1:

| Lys | Arg | Pro | Gly | Met | Tyr | Ile | Gly | Asp | Thr | Asp | Asp | Gly | Thr | Gly | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| His | His | Met | Val | Phe | Glu | Val | Val | Asp | Asn | Ala | Ile | Asp | Glu | Ala | Leu |
|     |     |     | 20  |     |     |     |     | 25  |     |     |     |     | 30  |     |     |
| Ala | Gly | His | Cys | Lys | Glu | Ile | Ile | Val | Thr | Ile | His | Ala | Asp | Asn | Ser |
|     |     | 35  |     |     |     |     | 40  |     |     |     |     | 45  |     |     |     |
| Val | Ser | Val | Gln | Asp | Asp | Gly | Arg | Gly | Ile | Pro |     |     |     |     |     |
|     | 50  |     |     |     |     | 55  |     |     |     |     |     |     |     |     |     |

(2) INFORMATION FOR SEQ ID NO:2:

(i) SEQUENCE CHARACTERISTICS:
(A) LENGTH: 59 amino acids
(B) TYPE: amino acid
(C) STRANDEDNESS:
(D) TOPOLOGY: unknown (ii) MOLECULE TYPE: protein (vi) ORIGINAL SOURCE:
(A) ORGANISM: Shigella dysenteriae (xi) SEQUENCE DESCRIPTION: SEQ ID NO:2:

| Lys | Arg | Pro | Gly | Met | Tyr | Ile | Gly | Asp | Thr | Asp | Asp | Gly | Thr | Gly | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| His | His | Met | Val | Phe | Glu | Val | Val | Asp | Asn | Ala | Ile | Asp | Glu | Ala | Leu |
|     |     |     | 20  |     |     |     |     | 25  |     |     |     |     | 30  |     |     |
| Ala | Gly | His | Cys | Lys | Glu | Ile | Ile | Val | Thr | Ile | His | Ala | Asp | Asn | Ser |
|     |     | 35  |     |     |     |     | 40  |     |     |     |     | 45  |     |     |     |
| Val | Ser | Val | Gln | Asp | Asp | Gly | Arg | Gly | Ile | Pro |     |     |     |     |     |
|     | 50  |     |     |     |     | 55  |     |     |     |     |     |     |     |     |     |

(2) INFORMATION FOR SEQ ID NO:3:

(i) SEQUENCE CHARACTERISTICS:
(A) LENGTH: 59 amino acids
(B) TYPE: amino acid
(C) STRANDEDNESS:
(D) TOPOLOGY: unknown (ii) MOLECULE TYPE: protein (vi) ORIGINAL SOURCE:
(A) ORGANISM: Salmonella typhimurium (xi) SEQUENCE DESCRIPTION: SEQ ID NO:3:

| Lys | Arg | Pro | Gly | Met | Tyr | Ile | Gly | Asp | Thr | Asp | Asp | Gly | Thr | Gly | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| His | His | Met | Val | Phe | Glu | Val | Val | Asp | Asn | Ala | Ile | Asp | Glu | Ala | Leu |
|     |     |     | 20  |     |     |     |     | 25  |     |     |     |     | 30  |     |     |
| Ala | Gly | His | Cys | Lys | Asp | Ile | Val | Val | Thr | Ile | His | Ala | Asp | Asn | Ser |

Val Ser Val Thr Asp Asp Gly Arg Gly Ile Pro
    50                  55

(2) INFORMATION FOR SEQ ID NO:4:

(i) SEQUENCE CHARACTERISTICS:
      (A) LENGTH: 59 amino acids
      (B) TYPE: amino acid
      (C) STRANDEDNESS:
      (D) TOPOLOGY: unknown (ii) MOLECULE TYPE: protein (vi) ORIGINAL SOURCE:
      (A) ORGANISM: Pseudomonas aeruginosa (xi) SEQUENCE DESCRIPTION: SEQ ID NO:4:

Lys Arg Pro Gly Met Tyr Ile Gly Asp Thr Asp Asp Gly Thr Gly Leu
1               5                   10                  15

His His Met Val Phe Glu Val Val Asp Asn Ser Ile Asp Glu Ala Leu
            20                  25                  30

Ala Gly Tyr Cys Ser Glu Ile Ser Ile Thr Ile His Thr Asp Glu Ser
            35                  40                  45

Ile Thr Val Arg Asp Asp Gly Arg Gly Ile Pro
            50                  55

(2) INFORMATION FOR SEQ ID NO:5:

(i) SEQUENCE CHARACTERISTICS:
      (A) LENGTH: 59 amino acids
      (B) TYPE: amino acid
      (C) STRANDEDNESS:
      (D) TOPOLOGY: unknown (ii) MOLECULE TYPE: protein (vi) ORIGINAL SOURCE:
      (A) ORGANISM: Legionella pneumoniae (xi) SEQUENCE DESCRIPTION: SEQ ID NO:5:

Lys Arg Pro Gly Met Tyr Ile Gly Asp Thr Asp Asp Gly Thr Gly Leu
1               5                   10                  15

His His Met Val Phe Glu Val Val Asp Asn Ser Ile Asp Glu Ser Leu
            20                  25                  30

Ala Gly Tyr Cys Lys Glu Ile Phe Val Thr Ile His Ser Asp Glu Ser
            35                  40                  45

Ile Thr Val Lys Asp Asp Gly Arg Gly Ile Pro
            50                  55

(2) INFORMATION FOR SEQ ID NO:6:

(i) SEQUENCE CHARACTERISTICS:
      (A) LENGTH: 59 amino acids
      (B) TYPE: amino acid
      (C) STRANDEDNESS:
      (D) TOPOLOGY: unknown (ii) MOLECULE TYPE: protein (vi) ORIGINAL SOURCE:
      (A) ORGANISM: Agrobacterium tumefasciens (xi) SEQUENCE DESCRIPTION: SEQ ID NO:6:

Lys Arg Pro Gly Met Tyr Ile Gly Asp Thr Asp Asp Gly Ser Gly Leu
1               5                   10                  15

```
His His Met Val Tyr Glu Val Val Asp Asn Ala Ile Asp Glu Ala Leu
            20                  25                  30

Ala Gly His Ala Asp Leu Val Thr Val Thr Leu Asn Ala Asp Gly Ser
            35                  40                  45

Val Thr Val Thr Asp Asp Gly Arg Gly Ile Pro
            50                  55
```

( 2 ) INFORMATION FOR SEQ ID NO:7:

( i ) SEQUENCE CHARACTERISTICS:
        ( A ) LENGTH: 59 amino acids
        ( B ) TYPE: amino acid
        ( C ) STRANDEDNESS:
        ( D ) TOPOLOGY: unknown ( i i ) MOLECULE TYPE: protein ( v i ) ORIGINAL SOURCE:
        ( A ) ORGANISM: Rickettsiae rickettsii ( x i ) SEQUENCE DESCRIPTION: SEQ ID NO:7:

```
Lys Arg Pro Gly Met Tyr Ile Gly Asp Val Gly Asp Gly Ser Gly Leu
1               5                   10                  15

His His Met Ile Tyr Glu Val Val Asp Asn Ala Ile Asp Glu Ser Leu
            20                  25                  30

Ala Gly Tyr Cys Asp Leu Val Arg Val Thr Leu Asn Lys Asn Gly Ser
            35                  40                  45

Val Thr Val Ser Asp Asp Gly Arg Gly Ile Pro
            50                  55
```

( 2 ) INFORMATION FOR SEQ ID NO:8:

( i ) SEQUENCE CHARACTERISTICS:
        ( A ) LENGTH: 59 amino acids
        ( B ) TYPE: amino acid
        ( C ) STRANDEDNESS:
        ( D ) TOPOLOGY: unknown ( i i ) MOLECULE TYPE: protein ( v i ) ORIGINAL SOURCE:
        ( A ) ORGANISM: Rhodobacter capsulatus ( x i ) SEQUENCE DESCRIPTION: SEQ ID NO:8:

```
Lys Arg Pro Gly Met Tyr Ile Gly Asp Thr Asp Asp Gly Ser Gly Leu
1               5                   10                  15

His His Met Val Tyr Glu Val Val Asp Asn Gly Ile Asp Glu Ala Leu
            20                  25                  30

Ala Gly His Ala Asn Tyr Val Ala Val Lys Ile His Ala Asp Ser Ser
            35                  40                  45

Val Ser Val Arg Asp Asp Gly Arg Gly Ile Pro
            50                  55
```

( 2 ) INFORMATION FOR SEQ ID NO:9:

( i ) SEQUENCE CHARACTERISTICS:
        ( A ) LENGTH: 59 amino acids
        ( B ) TYPE: amino acid
        ( C ) STRANDEDNESS:
        ( D ) TOPOLOGY: unknown ( i i ) MOLECULE TYPE: protein ( v i ) ORIGINAL SOURCE:
        ( A ) ORGANISM: Rhodopseudomonas sphaeroides ( x i ) SEQUENCE DESCRIPTION: SEQ ID NO:9:

-continued

```
Lys Arg Pro Gly Met Tyr Ile Gly Asp Thr Asp Asp Gly Ser Gly Leu
1               5                   10                  15

His His Met Val Tyr Glu Val Val Asp Asn Gly Ile Asp Glu Ala Leu
            20                  25                  30

Ala Gly His Ala Thr Glu Val Ala Val Ile Ile His Ala Asp Asp Ser
        35                  40                  45

Val Ser Val Arg Asp Asp Gly Arg Gly Ile Pro
50                  55
```

(2) INFORMATION FOR SEQ ID NO:10:

(i) SEQUENCE CHARACTERISTICS:
  (A) LENGTH: 58 amino acids
  (B) TYPE: amino acid
  (C) STRANDEDNESS:
  (D) TOPOLOGY: unknown (ii) MOLECULE TYPE: protein (vi) ORIGINAL SOURCE:
  (A) ORGANISM: Campylobacter jejuni (xi) SEQUENCE DESCRIPTION: SEQ ID NO:10:

```
Lys Arg Pro Gly Met Tyr Ile Gly Asp Thr Asn Ile Gly Gly Leu His
1               5                   10                  15

His Met Ile Tyr Glu Val Val Asp Asn Ser Ile Asp Glu Ala Met Ala
            20                  25                  30

Gly His Cys Asp Thr Ile Asp Val Glu Ile Thr Thr Glu Gly Ser Cys
        35                  40                  45

Ile Val Ser Asp Asp Gly Arg Gly Ile Pro
50                  55
```

(2) INFORMATION FOR SEQ ID NO:11:

(i) SEQUENCE CHARACTERISTICS:
  (A) LENGTH: 59 amino acids
  (B) TYPE: amino acid
  (C) STRANDEDNESS:
  (D) TOPOLOGY: unknown (ii) MOLECULE TYPE: protein (vi) ORIGINAL SOURCE:
  (A) ORGANISM: Neisseria denitrificans (xi) SEQUENCE DESCRIPTION: SEQ ID NO:11:

```
Lys Arg Pro Gly Met Tyr Ile Gly Asp Thr Gln Asp Gly Ser Gly Leu
1               5                   10                  15

His His Met Val Phe Glu Val Leu Asp Asn Ala Ile Asp Glu Ala Leu
            20                  25                  30

Ala Gly His Cys Asp Lys Ile Arg Val Ile Ile His Ala Asp Asn Ser
        35                  40                  45

Val Ser Val Phe Asp Asp Gly Arg Gly Ile Pro
50                  55
```

(2) INFORMATION FOR SEQ ID NO:12:

(i) SEQUENCE CHARACTERISTICS:
  (A) LENGTH: 58 amino acids
  (B) TYPE: amino acid
  (C) STRANDEDNESS:
  (D) TOPOLOGY: unknown (ii) MOLECULE TYPE: protein (vi) ORIGINAL SOURCE:
  (A) ORGANISM: Anacystis nidulans (xi) SEQUENCE DESCRIPTION: SEQ ID NO:12:

Lys Arg Pro Gly Met Tyr Ile Gly Ser Thr Gly Pro Lys Gly Leu His
1               5                   10                  15

His Leu Val Tyr Glu Val Val Asp Asn Ala Val Asp Glu Ala Leu Ala
            20                  25                  30

Gly Tyr Cys Asn Thr Ile Asp Val Arg Leu Leu Glu Asp Gly Ser Cys
        35                  40                  45

Gln Val Thr Asp Asp Gly Arg Gly Ile Pro
        50                  55

(2) INFORMATION FOR SEQ ID NO:13:

(i) SEQUENCE CHARACTERISTICS:
    (A) LENGTH: 58 amino acids
    (B) TYPE: amino acid
    (C) STRANDEDNESS:
    (D) TOPOLOGY: unknown (ii) MOLECULE TYPE: protein (vi) ORIGINAL SOURCE:
    (A) ORGANISM: Chlamydia trachomatis (xi) SEQUENCE DESCRIPTION: SEQ ID NO:13:

Lys Arg Pro Gly Met Tyr Ile Gly Asp Thr Gly Val Thr Gly Leu His
1               5                   10                  15

His Leu Val Tyr Glu Val Val Asp Asn Ser Ile Asp Glu Ala Met Ala
            20                  25                  30

Gly Phe Cys Thr Glu Val Val Val Arg Ile Leu Glu Asp Gly Gly Ile
        35                  40                  45

Ser Ile Ser Asp Asp Gly Arg Gly Ile Pro
        50                  55

(2) INFORMATION FOR SEQ ID NO:14:

(i) SEQUENCE CHARACTERISTICS:
    (A) LENGTH: 58 amino acids
    (B) TYPE: amino acid
    (C) STRANDEDNESS:
    (D) TOPOLOGY: unknown (ii) MOLECULE TYPE: protein (vi) ORIGINAL SOURCE:
    (A) ORGANISM: Bacillus subtilis (xi) SEQUENCE DESCRIPTION: SEQ ID NO:14:

Lys Arg Pro Gly Met Tyr Ile Gly Ser Thr Asn Ser Lys Gly Leu His
1               5                   10                  15

His Leu Val Trp Glu Ile Val Asp Asn Ser Ile Asp Glu Ala Leu Ala
            20                  25                  30

Gly Tyr Cys Thr Asp Ile Asn Ile Gln Ile Glu Lys Asp Asn Ser Ile
        35                  40                  45

Thr Val Val Asp Asp Gly Arg Gly Ile Pro
        50                  55

(2) INFORMATION FOR SEQ ID NO:15:

(i) SEQUENCE CHARACTERISTICS:
    (A) LENGTH: 58 amino acids
    (B) TYPE: amino acid
    (C) STRANDEDNESS:

5,645,994

27

28

-continued ( D ) TOPOLOGY: unknown ( i i ) MOLECULE TYPE: protein ( v i ) ORIGINAL SOURCE:
  ( A ) ORGANISM: Borrelia burgdorferi ( x i ) SEQUENCE DESCRIPTION: SEQ ID NO:15:

| Lys | Arg | Pro | Gly | Met | Tyr | Ile | Gly | Ser | Val | Ser | Ile | Asn | Gly | Leu | His |
|---|---|---|---|---|---|---|---|---|---|---|---|---|---|---|---|
| 1 | | | | 5 | | | | | 10 | | | | | | 15 |
| His | Leu | Val | Tyr | Glu | Val | Val | Asp | Asn | Ser | Ile | Asp | Glu | Ala | Leu | Ala |
| | | | 20 | | | | | 25 | | | | | 30 | | |
| Gly | Phe | Cys | Asp | Arg | Ile | Asp | Val | Ile | Ile | Asn | Leu | Asp | Asn | Thr | Ile |
| | | 35 | | | | | 40 | | | | | 45 | | | |
| Thr | Val | Ile | Asp | Asp | Gly | Arg | Gly | Ile | Pro | | | | | | |
| | 50 | | | | | 55 | | | | | | | | | |

( 2 ) INFORMATION FOR SEQ ID NO:16:

( i ) SEQUENCE CHARACTERISTICS:
  ( A ) LENGTH: 58 amino acids
  ( B ) TYPE: amino acid
  ( C ) STRANDEDNESS:
  ( D ) TOPOLOGY: unknown ( i i ) MOLECULE TYPE: protein ( v i ) ORIGINAL SOURCE:
  ( A ) ORGANISM: Mycoplasma pneumoniae ( x i ) SEQUENCE DESCRIPTION: SEQ ID NO:16:

| Lys | Arg | Pro | Gly | Met | Tyr | Ile | Gly | Ser | Thr | Gly | Glu | Glu | Gly | Leu | His |
|---|---|---|---|---|---|---|---|---|---|---|---|---|---|---|---|
| 1 | | | | 5 | | | | | 10 | | | | | | 15 |
| His | Met | Ile | Trp | Glu | Ile | Ile | Asp | Asn | Ser | Ile | Asp | Glu | Ala | Met | Gly |
| | | | 20 | | | | | 25 | | | | | 30 | | |
| Gly | Phe | Ala | Ser | Thr | Val | Lys | Leu | Thr | Leu | Lys | Asp | Asn | Phe | Val | Thr |
| | | 35 | | | | | 40 | | | | | 45 | | | |
| Ile | Val | Glu | Asp | Asp | Gly | Arg | Gly | Ile | Pro | | | | | | |
| | 50 | | | | | 55 | | | | | | | | | |

( 2 ) INFORMATION FOR SEQ ID NO:17:

( i ) SEQUENCE CHARACTERISTICS:
  ( A ) LENGTH: 141 amino acids
  ( B ) TYPE: amino acid
  ( C ) STRANDEDNESS: Not Relevant
  ( D ) TOPOLOGY: Not Relevant ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
  ( A ) ORGANISM: Escherichia coli ( x i ) SEQUENCE DESCRIPTION: SEQ ID NO:17:

| Asp | Gly | Leu | Lys | Pro | Val | His | Arg | Arg | Val | Leu | Tyr | Ala | Met | Asn | Val |
|---|---|---|---|---|---|---|---|---|---|---|---|---|---|---|---|
| 1 | | | | 5 | | | | | 10 | | | | | | 15 |
| Leu | Gly | Asn | Asp | Trp | Asn | Lys | Ala | Tyr | Lys | Lys | Ser | Ala | Arg | Val | Val |
| | | | 20 | | | | | 25 | | | | | 30 | | |
| Gly | Asp | Val | Ile | Gly | Lys | Tyr | His | Pro | His | Gly | Asp | Ser | Ala | Val | Tyr |
| | | 35 | | | | | 40 | | | | | 45 | | | |

```
Asp  Thr  Ile  Val  Arg  Met  Ala  Gln  Pro  Phe  Ser  Leu  Arg  Tyr  Met  Leu
     50                      55                      60

Val  Asp  Gly  Gln  Gly  Asn  Phe  Gly  Ser  Ile  Asp  Gly  Asp  Ser  Ala  Ala
65                      70                      75                           80

Ala  Met  Arg  Tyr  Thr  Glu  Ile  Arg  Leu  Ala  Lys  Ile  Ala  His  Glu  Leu
                    85                      90                      95

Met  Ala  Asp  Leu  Glu  Lys  Glu  Thr  Val  Asp  Phe  Val  Asp  Asn  Tyr  Asp
               100                     105                     110

Gly  Thr  Glu  Lys  Ile  Pro  Asp  Val  Met  Pro  Thr  Lys  Ile  Pro  Asn  Leu
               115                     120                     125

Leu  Val  Asn  Gly  Ser  Ser  Gly  Ile  Ala  Val  Gly  Met  Ala
     130                     135                     140
```

(2) INFORMATION FOR SEQ ID NO:18:

(i) SEQUENCE CHARACTERISTICS:
    (A) LENGTH: 141 amino acids
    (B) TYPE: amino acid
    (C) STRANDEDNESS:
    (D) TOPOLOGY: Not Relevant (ii) MOLECULE TYPE: protein (iii) HYPOTHETICAL: NO (iv) ANTI-SENSE: NO (v) FRAGMENT TYPE: internal (vi) ORIGINAL SOURCE:
    (A) ORGANISM: Shigella dysenteriae (xi) SEQUENCE DESCRIPTION: SEQ ID NO:18:

```
Asp  Gly  Leu  Lys  Pro  Val  His  Arg  Arg  Val  Leu  Tyr  Ala  Met  Asn  Val
1                   5                      10                      15

Leu  Gly  Asn  Asp  Trp  Asn  Lys  Ala  Tyr  Lys  Lys  Ser  Ala  Arg  Val  Val
               20                      25                      30

Gly  Asp  Val  Ile  Gly  Lys  Tyr  His  Pro  His  Gly  Asp  Ser  Ala  Val  Tyr
               35                      40                      45

Asp  Thr  Ile  Val  Arg  Leu  Ala  Gln  Pro  Phe  Ser  Leu  Arg  Tyr  Met  Leu
     50                      55                      60

Val  Asp  Gly  Gln  Gly  Asn  Phe  Gly  Ser  Ile  Asp  Gly  Asp  Ser  Ala  Ala
65                      70                      75                           80

Ala  Met  Arg  Tyr  Thr  Glu  Ile  Arg  Leu  Ala  Lys  Ile  Ala  His  Glu  Leu
                    85                      90                      95

Met  Ala  Asp  Leu  Glu  Lys  Glu  Thr  Val  Asp  Phe  Val  Asp  Asn  Tyr  Asp
               100                     105                     110

Gly  Thr  Glu  Lys  Ile  Pro  Asp  Val  Met  Pro  Thr  Lys  Ile  Pro  Asn  Leu
               115                     120                     125

Leu  Val  Asn  Gly  Ser  Ser  Gly  Ile  Ala  Val  Gly  Met  Ala
     130                     135                     140
```

(2) INFORMATION FOR SEQ ID NO:19:

(i) SEQUENCE CHARACTERISTICS:
    (A) LENGTH: 141 amino acids
    (B) TYPE: amino acid
    (C) STRANDEDNESS:
    (D) TOPOLOGY: Not Relevant (ii) MOLECULE TYPE: protein (iii) HYPOTHETICAL: NO ( i v ) ANTI-SENSE: NO ( v ) FRAGMENT TYPE: internal ( v i ) ORIGINAL SOURCE:
    ( A ) ORGANISM: Salmonella typhimurium ( x i ) SEQUENCE DESCRIPTION: SEQ ID NO:19:

| Asp | Gly | Leu | Lys | Pro | Val | His | Arg | Arg | Val | Leu | Tyr | Ala | Met | Asn | Val |
|---|---|---|---|---|---|---|---|---|---|---|---|---|---|---|---|
| 1 | | | | 5 | | | | | 10 | | | | | 15 | |
| Leu | Gly | Asn | Asp | Trp | Asn | Lys | Ala | Tyr | Lys | Lys | Ser | Ala | Arg | Val | Val |
| | | | 20 | | | | | 25 | | | | | 30 | | |
| Gly | Asp | Val | Ile | Gly | Lys | Tyr | His | Pro | His | Gly | Asp | Ser | Ala | Val | Tyr |
| | | | 35 | | | | 40 | | | | | 45 | | | |
| Asp | Thr | Ile | Val | Arg | Met | Ala | Gln | Pro | Phe | Ser | Leu | Arg | Tyr | Met | Leu |
| | | 50 | | | | 55 | | | | | 60 | | | | |
| Val | Asp | Gly | Gln | Gly | Asn | Phe | Gly | Ser | Ile | Asp | Gly | Asp | Ser | Ala | Ala |
| 65 | | | | | 70 | | | | | 75 | | | | | 80 |
| Ala | Met | Arg | Tyr | Thr | Glu | Ile | Arg | Leu | Ala | Lys | Ile | Ala | His | Glu | Leu |
| | | | | 85 | | | | | 90 | | | | | 95 | |
| Met | Ala | Asp | Leu | Glu | Lys | Glu | Thr | Val | Asp | Phe | Val | Asp | Asn | Tyr | Asp |
| | | | 100 | | | | | 105 | | | | | 110 | | |
| Gly | Thr | Glu | Lys | Ile | Pro | Asp | Val | Met | Pro | Thr | Lys | Ile | Pro | Asn | Leu |
| | | | 115 | | | | | 120 | | | | | 125 | | |
| Leu | Val | Asn | Gly | Ser | Ser | Gly | Ile | Ala | Val | Gly | Met | Ala | | | |
| | | | 130 | | | | 135 | | | | | 140 | | | |

( 2 ) INFORMATION FOR SEQ ID NO:20:

( i ) SEQUENCE CHARACTERISTICS:
        ( A ) LENGTH: 141 amino acids
        ( B ) TYPE: amino acid
        ( C ) STRANDEDNESS:
        ( D ) TOPOLOGY: Not Relevant ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Klebsiella pneumoniae ( x i ) SEQUENCE DESCRIPTION: SEQ ID NO:20:

| Asp | Gly | Leu | Lys | Pro | Val | His | Arg | Arg | Val | Leu | Tyr | Ala | Met | Asn | Val |
|---|---|---|---|---|---|---|---|---|---|---|---|---|---|---|---|
| 1 | | | | 5 | | | | | 10 | | | | | 15 | |
| Leu | Gly | Asn | Asp | Trp | Asn | Lys | Ala | Tyr | Lys | Lys | Ser | Ala | Arg | Val | Val |
| | | | 20 | | | | | 25 | | | | | 30 | | |
| Gly | Asp | Val | Ile | Gly | Lys | Tyr | His | Pro | His | Gly | Asp | Thr | Ala | Val | Tyr |
| | | | 35 | | | | 40 | | | | | 45 | | | |
| Asp | Thr | Ile | Val | Arg | Met | Ala | Gln | Pro | Phe | Ser | Leu | Arg | Tyr | Met | Leu |
| | | 50 | | | | 55 | | | | | 60 | | | | |
| Val | Asp | Gly | Gln | Gly | Asn | Phe | Gly | Ser | Val | Asp | Gly | Asp | Ser | Ala | Ala |
| 65 | | | | | 70 | | | | | 75 | | | | | 80 |
| Ala | Met | Arg | Tyr | Thr | Glu | Ile | Arg | Met | Ser | Lys | Ile | Ala | His | Glu | Leu |
| | | | | 85 | | | | | 90 | | | | | 95 | |
| Met | Ala | Asp | Leu | Glu | Lys | Glu | Thr | Val | Asp | Phe | Val | Asp | Asn | Tyr | Asp |
| | | | 100 | | | | | 105 | | | | | 110 | | |
| Gly | Thr | Glu | Lys | Ile | Pro | Asp | Val | Met | Pro | Thr | Lys | Ile | Pro | Asn | Leu |

|     |     |     |     | 115 |     |     |     | 120 |     |     |     | 125 |     |     |
|---|---|---|---|---|---|---|---|---|---|---|---|---|---|---|
| Leu | Val | Asn | Gly | Ser | Phe | Gly | Ile | Ala | Val | Gly | Met | Ala |     |     |
|     |     |     | 130 |     |     | 135 |     |     |     | 140 |     |     |     |     |

(2) INFORMATION FOR SEQ ID NO:21:

(i) SEQUENCE CHARACTERISTICS:
        (A) LENGTH: 140 amino acids
        (B) TYPE: amino acid
        (C) STRANDEDNESS:
        (D) TOPOLOGY: Not Relevant (ii) MOLECULE TYPE: protein (iii) HYPOTHETICAL: NO (iv) ANTI-SENSE: NO (v) FRAGMENT TYPE: internal (vi) ORIGINAL SOURCE:
        (A) ORGANISM: Pseudomonas aeruginosa (xi) SEQUENCE DESCRIPTION: SEQ ID NO:21:

| Asp | Gly | Leu | Lys | Pro | Val | His | Arg | Arg | Val | Leu | Ala | Met | Ser | Glu | Leu |
|---|---|---|---|---|---|---|---|---|---|---|---|---|---|---|---|
| 1 |     |     |     | 5 |     |     |     |     | 10 |     |     |     |     | 15 |     |
| Gly | Asn | Asp | Trp | Asn | Lys | Pro | Tyr | Lys | Lys | Ser | Ala | Arg | Val | Val | Gly |
|     |     |     | 20 |     |     |     |     | 25 |     |     |     |     | 30 |     |     |
| Asp | Val | Ile | Gly | Lys | Tyr | His | Pro | His | Gly | Asp | Thr | Ala | Val | Tyr | Asp |
|     |     |     | 35 |     |     |     |     | 40 |     |     |     | 45 |     |     |     |
| Thr | Ile | Val | Arg | Leu | Ala | Gln | Pro | Phe | Ser | Leu | Arg | Tyr | Met | Leu | Val |
|     |     | 50 |     |     |     |     | 55 |     |     |     |     | 60 |     |     |     |
| Asp | Gly | Gln | Gly | Asn | Phe | Gly | Ser | Val | Asp | Gly | Asp | Asn | Ala | Ala | Ala |
| 65 |     |     |     |     | 70 |     |     |     |     | 75 |     |     |     |     | 80 |
| Met | Arg | Tyr | Thr | Glu | Val | Arg | Met | Ala | Lys | Leu | Ala | His | Glu | Leu | Leu |
|     |     |     |     | 85 |     |     |     |     | 90 |     |     |     |     | 95 |     |
| Ala | Asp | Leu | Glu | Lys | Glu | Thr | Val | Asp | Trp | Val | Pro | Asn | Tyr | Asp | Gly |
|     |     |     |     | 100 |     |     |     |     | 105 |     |     |     |     | 110 |     |
| Thr | Glu | Gln | Ile | Pro | Ala | Val | Met | Pro | Thr | Lys | Ile | Pro | Asn | Leu | Leu |
|     |     |     | 115 |     |     |     |     | 120 |     |     |     |     | 125 |     |     |
| Val | Asn | Gly | Ser | Ser | Gly | Ile | Ala | Val | Gly | Met | Ala |     |     |     |     |
|     |     |     | 130 |     |     | 135 |     |     |     |     | 140 |     |     |     |     |

(2) INFORMATION FOR SEQ ID NO:22:

(i) SEQUENCE CHARACTERISTICS:
        (A) LENGTH: 141 amino acids
        (B) TYPE: amino acid
        (C) STRANDEDNESS:
        (D) TOPOLOGY: Not Relevant (ii) MOLECULE TYPE: protein (iii) HYPOTHETICAL: NO (iv) ANTI-SENSE: NO (v) FRAGMENT TYPE: internal (vi) ORIGINAL SOURCE:
        (A) ORGANISM: Neisseria gonorrhea A (xi) SEQUENCE DESCRIPTION: SEQ ID NO:22:

| Asp | Gly | Leu | Lys | Pro | Val | His | Arg | Arg | Ile | Leu | Phe | Ala | Met | Arg | Asp |
|---|---|---|---|---|---|---|---|---|---|---|---|---|---|---|---|
| 1 |     |     |     | 5 |     |     |     |     | 10 |     |     |     |     | 15 |     |
| Met | Gly | Leu | Thr | Ala | Gly | Ala | Asn | Arg | Val | Lys | Ser | Ala | Arg | Val | Val |

```
              20                    25                         30

Gly  Glu  Ile  Leu  Gly  Lys  Tyr  His  Pro  His  Gly  Asp  Ser  Ser  Ala  Tyr
              35                        40                   45

Glu  Ala  Met  Val  Arg  Met  Ala  Gln  Asp  Phe  Thr  Leu  Arg  Tyr  Pro  Leu
         50                       55                        60

Ile  Asp  Gly  Ile  Gly  Asn  Phe  Gly  Ser  Arg  Asp  Gly  Asp  Gly  Ala  Ala
    65                       70                        75                        80

Ala  Met  Arg  Tyr  Thr  Glu  Ala  Gly  Leu  Thr  Pro  Ile  Ala  Glu  Leu  Leu
                        85                        90                             95

Leu  Ser  Glu  Ile  Asn  Gln  Gly  Thr  Val  Asp  Phe  Met  Pro  Asn  Tyr  Asp
                   100                      105                       110

Gly  Ala  Phe  Asp  Glu  Pro  Leu  His  Leu  Pro  Ala  Arg  Leu  Pro  Met  Val
                   115                      120                       125

Leu  Leu  Asn  Gly  Ala  Ser  Gly  Ile  Ala  Val  Gly  Met  Ala
                   130                      135                       140
```

( 2 ) INFORMATION FOR SEQ ID NO:23:

( i ) SEQUENCE CHARACTERISTICS:
        ( A ) LENGTH: 141 amino acids
        ( B ) TYPE: amino acid
        ( C ) STRANDEDNESS:
        ( D ) TOPOLOGY: Not Relevant ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Neisseria gonorrheas B ( x i ) SEQUENCE DESCRIPTION: SEQ ID NO:23:

```
    Asp  Gly  Leu  Lys  Pro  Val  His  Arg  Arg  Val  Leu  Tyr  Ala  Met  His  Glu
    1                   5                        10                       15

Leu  Lys  Asn  Asn  Trp  Asn  Ala  Ala  Tyr  Lys  Lys  Ser  Ala  Arg  Ile  Val
                   20                       25                        30

Gly  Asp  Val  Ile  Gly  Lys  Tyr  His  Pro  His  Gly  Asp  Ser  Ala  Val  Tyr
                   35                       40                        45

Asp  Thr  Ile  Val  Arg  Met  Ala  Gln  Asn  Phe  Ala  Met  Arg  Tyr  Val  Leu
         50                       55                        60

Ile  Asp  Gly  Gln  Gly  Asn  Phe  Gly  Ser  Val  Asp  Gly  Leu  Ala  Ala  Ala
    65                       70                        75                        80

Ala  Met  Arg  Tyr  Thr  Glu  Ile  Arg  Met  Ala  Lys  Ile  Ser  His  Glu  Met
                        85                        90                             95

Leu  Ala  Asp  Ile  Glu  Glu  Glu  Thr  Val  Asn  Phe  Gly  Pro  Asn  Tyr  Asp
                   100                      105                       110

Gly  Ser  Glu  His  Glu  Pro  Leu  Val  Leu  Pro  Thr  Arg  Phe  Pro  Thr  Leu
                   115                      120                       125

Leu  Val  Asn  Gly  Ser  Ser  Gly  Ile  Ala  Val  Gly  Met  Ala
                   130                      135                       140
```

( 2 ) INFORMATION FOR SEQ ID NO:24:

( i ) SEQUENCE CHARACTERISTICS:
        ( A ) LENGTH: 141 amino acids
        ( B ) TYPE: amino acid
        ( C ) STRANDEDNESS:
        ( D ) TOPOLOGY: Not Relevant (i i) MOLECULE TYPE: protein (i i i) HYPOTHETICAL: NO (i v) ANTI-SENSE: NO (v) FRAGMENT TYPE: internal (v i) ORIGINAL SOURCE:
    (A) ORGANISM: Bacillus subtilis (x i) SEQUENCE DESCRIPTION: SEQ ID NO:24:

```
Asp Gly Leu Lys Pro Val His Arg Arg Ile Leu Tyr Ala Met Asn Asp
 1               5                  10                  15

Leu Gly Met Thr Ser Asp Lys Pro Tyr Lys Lys Ser Ala Arg Ile Val
                20                  25                  30

Gly Glu Val Ile Gly Lys Tyr His Pro His Gly Asp Ser Ala Val Tyr
            35                  40                  45

Glu Ser Met Val Arg Met Ala Gln Asp Phe Asn Tyr Arg Tyr Met Leu
        50                  55                  60

Val Asp Gly His Gly Asn Phe Gly Ser Val Asp Gly Asp Ser Ala Ala
65                  70                  75                  80

Ala Met Arg Tyr Thr Glu Ala Arg Met Ser Lys Ile Ser Met Glu Ile
                85                  90                  95

Leu Arg Asp Ile Thr Lys Asp Thr Ile Asp Tyr Gln Asp Asn Tyr Asp
               100                 105                 110

Gly Ser Glu Arg Glu Pro Val Val Met Pro Ser Arg Phe Pro Asn Leu
           115                 120                 125

Leu Val Asn Gly Ala Ala Gly Ile Ala Val Gly Met Ala
           130                 135                 140
```

(2) INFORMATION FOR SEQ ID NO:25:

(i) SEQUENCE CHARACTERISTICS:
        (A) LENGTH: 141 amino acids
        (B) TYPE: amino acid
        (C) STRANDEDNESS:
        (D) TOPOLOGY: Not Relevant (i i) MOLECULE TYPE: protein (i i i) HYPOTHETICAL: NO (i v) ANTI-SENSE: NO (v) FRAGMENT TYPE: internal (v i) ORIGINAL SOURCE:
    (A) ORGANISM: Borrelia burgdorferi A (x i) SEQUENCE DESCRIPTION: SEQ ID NO:25:

```
Asp Gly Leu Lys Pro Val His Arg Arg Ile Leu Tyr Ser Met Tyr Glu
 1               5                  10                  15

Met Gly Leu Arg Ser Asp Lys Ala Phe Lys Lys Ala Gly Arg Ile Val
                20                  25                  30

Gly Asp Val Leu Gly Lys Tyr His Pro His Gly Asp Gln Ser Ile Tyr
            35                  40                  45

Asp Ala Leu Val Arg Leu Ala Gln Asp Phe Ser Leu Arg Tyr Pro Arg
        50                  55                  60

Asn Thr Gly Gln Gly Asn Phe Gly Ser Ile Asp Gly Asp Pro Pro Ala
65                  70                  75                  80

Ala Met Arg Tyr Thr Glu Ala Lys Met Glu Lys Ile Thr Glu Tyr Ile
                85                  90                  95
```

5,645,994

| Val | Lys | Asp | Ile | Asp | Lys | Glu | Thr | Val | Asn | Phe | Lys | Ser | Asn | Tyr | Asp |
|  |  |  | 100 |  |  |  | 105 |  |  |  | 110 |  |  |  |  |

| Asp | Ser | Leu | Ser | Glu | Pro | Glu | Ile | Met | Pro | Ser | Ser | Phe | Pro | Phe | Leu |
|  |  | 115 |  |  |  | 120 |  |  |  |  | 125 |  |  |  |  |

| Leu | Val | Asn | Gly | Ser | Ser | Gly | Ile | Ala | Val | Gly | Met | Ala |
|  | 130 |  |  |  |  | 135 |  |  |  |  | 140 |  |

( 2 ) INFORMATION FOR SEQ ID NO:26:

( i ) SEQUENCE CHARACTERISTICS:
      ( A ) LENGTH: 132 amino acids
      ( B ) TYPE: amino acid
      ( C ) STRANDEDNESS:
      ( D ) TOPOLOGY: Not Relevant ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
      ( A ) ORGANISM: Borrelia burgdorferi B ( x i ) SEQUENCE DESCRIPTION: SEQ ID NO:26:

| Asp | Gly | Leu | Lys | Pro | Val | His | Arg | Arg | Ile | Ile | His | Ser | Leu | Phe | Glu |
| 1 |  |  |  | 5 |  |  |  |  | 10 |  |  |  |  | 15 |  |

| Met | His | Asp | Gly | Asn | Phe | His | Lys | Val | Arg | Asn | Val | Val | Gly | Asn | Thr |
|  |  |  | 20 |  |  |  |  | 25 |  |  |  |  | 30 |  |  |

| Met | Lys | Tyr | His | Pro | His | Gly | Asp | Thr | Ser | Ile | Tyr | Glu | Ala | Leu | Val |
|  |  | 35 |  |  |  |  | 40 |  |  |  |  | 45 |  |  |  |

| Asn | Ile | Ala | Asn | Lys | Asp | Leu | Phe | Ile | Glu | Lys | Gln | Gly | Asn | Phe | Gly |
|  | 50 |  |  |  |  | 55 |  |  |  |  | 60 |  |  |  |  |

| Asn | Leu | Phe | Thr | Gly | Asp | Pro | Ala | Ser | Ala | Ser | Arg | Tyr | Ile | Glu | Cys |
| 65 |  |  |  |  | 70 |  |  |  |  | 75 |  |  |  |  | 80 |

| Arg | Leu | Thr | Pro | Leu | Ala | Phe | Asp | Val | Leu | Tyr | Ser | Lys | Glu | Ile | Thr |
|  |  |  |  | 85 |  |  |  |  | 90 |  |  |  |  | 95 |  |

| Ile | Tyr | Glu | Ser | Ser | Tyr | Asp | Gly | Arg | Asn | Asn | Glu | Pro | Leu | Leu | Tyr |
|  |  |  | 100 |  |  |  |  | 105 |  |  |  |  | 110 |  |  |

| Pro | Ala | Lys | Ile | Pro | Val | Ile | Leu | Ile | Gln | Gly | Ser | Glu | Gly | Ile | Ala |
|  |  | 115 |  |  |  |  | 120 |  |  |  |  | 125 |  |  |  |

| Val | Gly | Met | Ala |
|  | 130 |  |  |

( 2 ) INFORMATION FOR SEQ ID NO:27:

( i ) SEQUENCE CHARACTERISTICS:
      ( A ) LENGTH: 132 amino acids
      ( B ) TYPE: amino acid
      ( C ) STRANDEDNESS:
      ( D ) TOPOLOGY: Not Relevant ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
      ( A ) ORGANISM: Chlamydia trachomatis ( x i ) SEQUENCE DESCRIPTION: SEQ ID NO:27:

-continued

Asp Gly Leu Lys Pro Val His Arg Arg Leu Leu Trp Thr Leu Phe Arg
1 5 10 15

Met Asp Asp Gly Lys Met His Lys Val Ala Asn Ile Ala Gly Arg Thr
20 25 30

Met Ala Leu His Pro His Gly Asp Ala Pro Ile Val Glu Ala Leu Val
35 40 45

Val Leu Ala Asn Lys Gly Phe Leu Ile Glu Thr Gln Gly Asn Phe Gly
50 55 60

Asn Pro Leu Thr Gly Asp Pro His Ala Ala Ala Arg Tyr Ile Glu Ala
65 70 75 80

Arg Leu Ser Pro Leu Ala Lys Glu Val Leu Phe Asn Thr Asp Leu Met
85 90 95

Thr Phe His Asp Ser Tyr Asp Gly Arg Glu Gln Glu Pro Asp Ile Leu
100 105 110

Pro Ala Lys Ile Pro Leu Leu Leu Leu His Gly Val Asp Gly Ile Ala
115 120 125

Val Gly Met Ala
130

( 2 ) INFORMATION FOR SEQ ID NO:28:

( i ) SEQUENCE CHARACTERISTICS:
( A ) LENGTH: 143 amino acids
( B ) TYPE: amino acid
( C ) STRANDEDNESS:
( D ) TOPOLOGY: Not Relevant ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
( A ) ORGANISM: Legionella pneumoniae ( x i ) SEQUENCE DESCRIPTION: SEQ ID NO:28:

Asp Gly Leu Lys Pro Val His Arg Arg Lys Ile Val Tyr Ala Met Ser
1 5 10 15

Glu Leu Gly Leu Lys Ala Thr Ala Lys Tyr Lys Lys Ser Ala Arg Thr
20 25 30

Val Gly Asp Val Leu Gly Lys Phe His Pro His Gly Asp Ser Ala Cys
35 40 45

Tyr Glu Ala Met Val Leu Met Ala Gln Pro Phe Ser Tyr Arg Tyr Pro
50 55 60

Phe Val Asp Gly Gln Gly Asn Trp Gly Ser Pro Asp Asp Pro Lys Ser
65 70 75 80

Phe Ala Ala Met Arg Tyr Thr Glu Ala Arg Leu Ser His Tyr Ala Asp
85 90 95

Val Leu Leu Gly Glu Leu Leu Gln Gly Thr Val Asp Trp Val Asp Asn
100 105 110

Phe Asp Gly Thr Leu Gln Glu Pro Ala Leu Leu Pro Ala Arg Leu Pro
115 120 125

Asn Ile Leu Leu Asn Gly Ala Thr Gly Ile Ala Val Gly Met Ala
130 135 140

( 2 ) INFORMATION FOR SEQ ID NO:29:

(i) SEQUENCE CHARACTERISTICS:
    (A) LENGTH: 138 amino acids
    (B) TYPE: amino acid
    (C) STRANDEDNESS:
    (D) TOPOLOGY: Not Relevant (ii) MOLECULE TYPE: protein (iii) HYPOTHETICAL: NO (iv) ANTI-SENSE: NO (v) FRAGMENT TYPE: internal (vi) ORIGINAL SOURCE:
    (A) ORGANISM: Bacteriophage T4

(xi) SEQUENCE DESCRIPTION: SEQ ID NO:29:

| Asp | Gly | Phe | Lys | Pro | Val | Gln | Arg | Phe | Val | Ile | Ala | Arg | Ala | Leu | Asp |
|---|---|---|---|---|---|---|---|---|---|---|---|---|---|---|---|
| 1 | | | | 5 | | | | | 10 | | | | | 15 | |
| Leu | Ala | Arg | Gly | Asn | Lys | Asp | Lys | Phe | His | Lys | Leu | Ala | Ser | Ile | Ala |
| | | | 20 | | | | 25 | | | | | 30 | | | |
| Gly | Gly | Val | Ala | Asp | Leu | Gly | Tyr | Ala | His | His | Gly | Glu | Thr | Leu | His |
| | | | 35 | | | | 40 | | | | | 45 | | | |
| Lys | Ser | Gln | Cys | Leu | Met | Ala | Asn | Thr | Trp | Asn | Asn | Phe | Pro | Leu |
| | 50 | | | | | 55 | | | | | 60 | | | | |
| Leu | Asp | Gly | Gln | Gly | Asn | Phe | Gly | Gly | Ser | Arg | Thr | Val | Gln | Lys | Ala |
| 65 | | | | | 70 | | | | | 75 | | | | | 80 |
| Ala | Ala | Ser | Arg | Tyr | Ile | Phe | Ala | Arg | Val | Ser | Lys | Asn | Phe | Tyr | Asn |
| | | | | 85 | | | | | 90 | | | | | 95 | |
| Val | Tyr | Lys | Asp | Thr | Glu | Tyr | Ala | Pro | Val | His | Gln | Asp | Lys | Glu | His |
| | | | 100 | | | | | 105 | | | | | 110 | | |
| Ile | Pro | Pro | Ala | Phe | Tyr | Leu | Pro | Ile | Ile | Pro | Thr | Val | Leu | Leu | Asn |
| | | 115 | | | | | 120 | | | | | 125 | | | |
| Gly | Val | Ser | Gly | Ile | Ala | Thr | Gly | Tyr | Ala |
| | 130 | | | | | 135 | | | |

(2) INFORMATION FOR SEQ ID NO:30:

(i) SEQUENCE CHARACTERISTICS:
    (A) LENGTH: 142 amino acids
    (B) TYPE: amino acid
    (C) STRANDEDNESS:
    (D) TOPOLOGY: Not Relevant (ii) MOLECULE TYPE: protein (iii) HYPOTHETICAL: NO (iv) ANTI-SENSE: NO (v) FRAGMENT TYPE: internal (vi) ORIGINAL SOURCE:
    (A) ORGANISM: Homo sapiens sapiens (xi) SEQUENCE DESCRIPTION: SEQ ID NO:30:

| Asp | Gly | Leu | Lys | Pro | Gly | Gln | Arg | Lys | Val | Leu | Phe | Thr | Cys | Phe | Lys |
|---|---|---|---|---|---|---|---|---|---|---|---|---|---|---|---|
| 1 | | | | 5 | | | | | 10 | | | | | 15 | |
| Arg | Asn | Asp | Lys | Arg | Glu | Val | Lys | Val | Ala | Gln | Leu | Ala | Gly | Ser | Val |
| | | | 20 | | | | 25 | | | | | 30 | | | |
| Ala | Glu | Met | Ser | Ser | Tyr | His | His | Gly | Glu | Asn | Ser | Leu | Met | Met | Thr |
| | | | 35 | | | | 40 | | | | | 45 | | | |
| Thr | Asn | Leu | Ala | Gln | Asn | Phe | Val | Gly | Ser | Asn | Asn | Leu | Asn | Leu | Leu |
| | 50 | | | | | 55 | | | | | 60 | | | | |

|  |  |  |  |  |  |  |  |  |  |  |  |  |  |  |
|---|---|---|---|---|---|---|---|---|---|---|---|---|---|---|
| Gln | Pro | Ile | Gly | Gln | Phe | Gly | Thr | Arg | Leu | His | Gly | Gly | Lys | Asp | Ser |
| 65 | | | | 70 | | | | | 75 | | | | | | 80 |
| Ala | Ser | Pro | Arg | Tyr | Ile | Phe | Thr | Met | Leu | Ser | Ser | Leu | Ala | Arg | Leu |
| | | | | 85 | | | | | 90 | | | | | 95 | |
| Leu | Phe | Pro | Pro | Lys | Asp | Asp | His | Thr | Leu | Lys | Phe | Leu | Leu | Tyr | Asp |
| | | | 100 | | | | | 105 | | | | | 110 | | |
| Asp | Asn | Gln | Arg | Val | Glu | Pro | Glu | Trp | Tyr | Ile | Pro | Ile | Ile | Pro | Met |
| | | 115 | | | | | 120 | | | | | 125 | | | |
| Val | Leu | Ile | Asn | Gly | Ala | Glu | Gly | Ile | Gly | Thr | Gly | Trp | Ser | | |
| | 130 | | | | | 135 | | | | | 140 | | | | |

( 2 ) INFORMATION FOR SEQ ID NO:31:

( i ) SEQUENCE CHARACTERISTICS:
        ( A ) LENGTH: 142 amino acids
        ( B ) TYPE: amino acid
        ( C ) STRANDEDNESS:
        ( D ) TOPOLOGY: Not Relevant ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Saccharomyces cerevisiae ( x i ) SEQUENCE DESCRIPTION: SEQ ID NO:31:

|  |  |  |  |  |  |  |  |  |  |  |  |  |  |  |  |
|---|---|---|---|---|---|---|---|---|---|---|---|---|---|---|---|
| Asp | Gly | Phe | Lys | Pro | Gly | Gln | Arg | Lys | Val | Leu | Tyr | Gly | Cys | Phe | Lys |
| 1 | | | | 5 | | | | | 10 | | | | | 15 | |
| Lys | Asn | Leu | Lys | Ser | Glu | Leu | Lys | Val | Ala | Gln | Leu | Ala | Pro | Tyr | Val |
| | | | 20 | | | | | 25 | | | | | 30 | | |
| Ser | Glu | Cys | Thr | Ala | Tyr | His | His | Gly | Glu | Gln | Ser | Leu | Ala | Gln | Thr |
| | | | 35 | | | | | 40 | | | | | 45 | | |
| Ile | Ile | Gly | Leu | Ala | Gln | Asn | Phe | Val | Gly | Ser | Asn | Asn | Ile | Tyr | Leu |
| | | 50 | | | | | 55 | | | | | 60 | | | |
| Leu | Leu | Pro | Asn | Gly | Ala | Phe | Gly | Thr | Arg | Ala | Thr | Gly | Gly | Lys | Asp |
| 65 | | | | | 70 | | | | | 75 | | | | | 80 |
| Ala | Ala | Ala | Ala | Arg | Tyr | Ile | Tyr | Thr | Glu | Leu | Asn | Lys | Leu | Thr | Arg |
| | | | | 85 | | | | | 90 | | | | | 95 | |
| Lys | Ile | Phe | His | Pro | Ala | Asp | Asp | Pro | Leu | Tyr | Lys | Tyr | Ile | Gln | Glu |
| | | | | 100 | | | | | 105 | | | | | 110 | |
| Asp | Glu | Lys | Thr | Val | Glu | Pro | Glu | Trp | Tyr | Leu | Pro | Ile | Leu | Pro | Met |
| | | | 115 | | | | | 120 | | | | | 125 | | |
| Ile | Leu | Val | Asn | Gly | Ala | Glu | Gly | Ile | Gly | Thr | Gly | Arg | Ser | | |
| | 130 | | | | | 135 | | | | | 140 | | | | |

( 2 ) INFORMATION FOR SEQ ID NO:32:

( i ) SEQUENCE CHARACTERISTICS:
        ( A ) LENGTH: 145 amino acids
        ( B ) TYPE: amino acid
        ( C ) STRANDEDNESS:
        ( D ) TOPOLOGY: Not Relevant ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
 ( A ) ORGANISM: Schizosaccharomyces pombe ( x i ) SEQUENCE DESCRIPTION: SEQ ID NO:32:

```
Asp Gly Leu Lys Pro Gly Gln Arg Lys Val Val Tyr Tyr Cys Phe Lys
 1               5                  10                  15

Arg Asn Leu Val His Glu Thr Lys Val Ser Arg Leu Ala Gly Tyr Val
              20                  25                  30

Ala Ser Glu Thr Ala Tyr Glu Thr Ala Tyr His His Gly Glu Val Ser
         35                  40                  45

Met Glu Gln Thr Ile Val Asn Leu Ala Gln Asn Phe Val Gly Ser Asn
     50                  55                  60

Asn Ile Asn Leu Leu Met Pro Asn Gly Gln Phe Gly Thr Arg Ser Glu
 65              70                  75                  80

Gly Gly Lys Asn Ala Ser Ala Ser Arg Tyr Leu Asn Thr Ala Leu Ser
              85                  90                  95

Pro Leu Ala Arg Val Leu Phe Asn Ser Asp Asp Gln Leu Leu Asn Tyr
             100                 105                 110

Gln Asn Asp Glu Gly Gln Trp Ile Glu Pro Glu Tyr Tyr Val Pro Ile
             115                 120                 125

Leu Pro Met Val Leu Val Asn Gly Ala Glu Gly Ile Gly Thr Gly Trp
     130                 135                 140

Ser
145
```

( 2 ) INFORMATION FOR SEQ ID NO:33:

( i ) SEQUENCE CHARACTERISTICS:
  ( A ) LENGTH: 423 base pairs
  ( B ) TYPE: nucleic acid
  ( C ) STRANDEDNESS: double
  ( D ) TOPOLOGY: Not Relevant ( i i ) MOLECULE TYPE: other nucleic acid
  ( A ) DESCRIPTION: /desc ="GyrA gene segment"

( i i i ) HYPOTHETICAL: NO ( i v ) ANTI-SENSE: NO ( v i ) ORIGINAL SOURCE:
  ( A ) ORGANISM: Bacteriodes fragilis ( x i ) SEQUENCE DESCRIPTION: SEQ ID NO:33:

```
GACGGGCTGA AGCCAGTGCA CCGCAGAATT CTCTACGGAA TGATGGAACT GGGAAATACA    60
TCAGACAAAC CCTATAAGAA ATCAGCCAGA ATCGTAGGTG AAGTACTTGG TAAGTATCAC   120
CCGCACGGAG ACTCTTCTGT ATATTTTGCG ATGGTACGTA TGGCTCAGGA ATGGGCAATG   180
CGCTATCCGC TGGTAGACGG GCAAGGTAAC TTCGGCTCTG TAGACGGCGA CAGTCCTGCT   240
GCCATGCGTT ACACTGAAGC ACGTCTGAAC AAATTAGGTG AAGAAATGAT GCAGGACCTC   300
TACAAAGAGA CTGTAGATTT CGAACCTAAC TTCGATAATA CGCTGATGGA ACCCAAAGTG   360
ATGCCGACAC GTATTCCGAA TTTGCTGGTT AACGGTGCTT CCGGGATCGC GGTAGGTATG   420
GCA                                                                 423
```

( 2 ) INFORMATION FOR SEQ ID NO:34:

( i ) SEQUENCE CHARACTERISTICS:
  ( A ) LENGTH: 396 base pairs
  ( B ) TYPE: nucleic acid
  ( C ) STRANDEDNESS: double (D) TOPOLOGY: Not Relevant (ii) MOLECULE TYPE: other nucleic acid
  (A) DESCRIPTION: /desc ="ParC gene segment"

(iii) HYPOTHETICAL: NO (iv) ANTI-SENSE: NO (vi) ORIGINAL SOURCE:
  (A) ORGANISM: Bacteriodes fragilis (xi) SEQUENCE DESCRIPTION: SEQ ID NO:34:

| | | | | | | |
|---|---|---|---|---|---|---|
| GACGGGCTGA | AGCCAGTGCA | CCGCCGCATC | CTGCACTCCA | TGAAACGCAT | GGACGACGGG | 60 |
| CGGTACAATA | AGGTGGCCAA | CATCGTAGGA | CATACCATGC | AGTTTCACCC | TCATGGCGAT | 120 |
| GCATCCATCG | GTGACGCATT | GGTACAGCTG | GGGCAGAAAG | ACCTGTTGGT | TGACTGCCAG | 180 |
| GGAAACTGGG | GTAATATCCT | TACCGGTGAC | GGTGCTGCTG | CTCCTCGTTA | TATTGAAGCA | 240 |
| CGCTTGTCGA | AGTTTGCACT | CGATGTAGTA | TTCAACCCCA | AAACCACCGA | ATGGAAGTTG | 300 |
| TCGTACGACG | GACGCAACAA | GGAGCCTATT | ACCTTACCGG | TAAAGTTCCC | GCTTTTGCTG | 360 |
| GCGCAAGGTG | TAGAGGGTAT | CGCCGTGGGT | ATGGCA | | | 396 |

(2) INFORMATION FOR SEQ ID NO:35:

(i) SEQUENCE CHARACTERISTICS:
    (A) LENGTH: 423 base pairs
    (B) TYPE: nucleic acid
    (C) STRANDEDNESS: double
    (D) TOPOLOGY: Not Relevant (ii) MOLECULE TYPE: other nucleic acid
    (A) DESCRIPTION: /desc ="GyrA gene segment"

(iii) HYPOTHETICAL: NO (iv) ANTI-SENSE: NO (vi) ORIGINAL SOURCE:
    (A) ORGANISM: Bacteroides melaninogenicus (xi) SEQUENCE DESCRIPTION: SEQ ID NO:35:

| | | | | | | |
|---|---|---|---|---|---|---|
| GACGGGTTAA | AGCCGGTACA | CAGGCGCATT | TTGTATGGAA | TGCTAGGGCT | GGGAAATACC | 60 |
| AGCGACAAGC | CATATAAGAA | ATGTGCGCGC | GTGGTGGGTG | ATGTTTTGGG | TAAGTATCAC | 120 |
| CCACATGGCG | ACTCCTCGGT | TTACGGGGCT | TTGGTGCGCT | TGGCACAAGA | TTGGAACATG | 180 |
| CGTTACACCT | TGGTAGACGG | TCAAGGAAAC | TTCGGAAGCG | TTGATGGAGA | CTCGGCTGCG | 240 |
| GCCATGCGTT | ACACAGAGTG | TAGGCTCTCG | AAGTTGGGCG | AACGTATCAT | GGACGACCTT | 300 |
| GATAAGGACA | CCGTTGATAT | GGACGAGAAC | TTCGATGCCA | CGCTGCAAGA | GCCTCAGGTG | 360 |
| ATGCCTACCA | AGATACCAAA | CCTACTCGTT | AACGGTGGAA | ACGGTATCGC | TGTCGGTATG | 420 |
| GCA | | | | | | 423 |

(2) INFORMATION FOR SEQ ID NO:36:

(i) SEQUENCE CHARACTERISTICS:
    (A) LENGTH: 396 base pairs
    (B) TYPE: nucleic acid
    (C) STRANDEDNESS: double
    (D) TOPOLOGY: Not Relevant (ii) MOLECULE TYPE: other nucleic acid
    (A) DESCRIPTION: /desc ="parC gene segment"

(iii) HYPOTHETICAL: NO (iv) ANTI-SENSE: NO ( v i ) ORIGINAL SOURCE:
     ( A ) ORGANISM: Bacteroides melaninogenicus ( x i ) SEQUENCE DESCRIPTION: SEQ ID NO:36:

| | | | | | | |
|---|---|---|---|---|---|---|
| GATGGGTTGA | AGCCGGTGCA | ACGCCGTATA | CTGCACTCGA | TGAAGCGCAT | GGACGATGGA | 60 |
| AGGTACAACA | AAGTGGCCAA | TATCGTGGGC | CATACCATGC | AGTTTCACCC | TCATGGTGAC | 120 |
| GCTTCTATCG | GCGACGCCCT | TGTGCAGATG | GGGCAAAAAG | ACTTGCTTAT | CGACACGCAA | 180 |
| GGAAACTGGG | GAAACATTCT | CACGGGCGAC | CGCGCAGCCG | CTCCGCGTTA | TATCGAGGCG | 240 |
| AGGCTTTCTA | AGTTCGCCCT | CGACACCGTT | TTCAATCCCA | AACCACGCA | ATGGCTAGCT | 300 |
| AGTTACGACG | GTAGAAATAA | AGAACCCATC | TCGCTACCTG | TGAAATTCCC | CTTGCTTTTG | 360 |
| GCTCAAGGGG | CGGAAGGCAT | AGCCGTAGGT | ATGGCA | | | 396 |

( 2 ) INFORMATION FOR SEQ ID NO:37:

( i ) SEQUENCE CHARACTERISTICS:
     ( A ) LENGTH: 423 base pairs
     ( B ) TYPE: nucleic acid
     ( C ) STRANDEDNESS: double
     ( D ) TOPOLOGY: Not Relevant ( i i ) MOLECULE TYPE: other nucleic acid
     ( A ) DESCRIPTION: /desc ="GyrA gene segment"

( i i i ) HYPOTHETICAL: NO ( i v ) ANTI-SENSE: NO ( v i ) ORIGINAL SOURCE:
     ( A ) ORGANISM: Bacteroides thetaiotamicron ( x i ) SEQUENCE DESCRIPTION: SEQ ID NO:37:

| | | | | | | |
|---|---|---|---|---|---|---|
| GATGGGTTGA | AACCTGTCCA | CCGTAGAATT | TTATACGGAA | TGATGGAATT | GGGTAATACT | 60 |
| TCAGACAAAC | CTTATAAAAA | ATCTGCAAGA | ATCGTGGGTG | AAGTATTGGG | TAAGTACCAT | 120 |
| CCGCATGGAG | ACTCTTCAGT | TTATTATGCT | ATGGTGCGTA | TGGCTCAGGA | ATGGGCAATG | 180 |
| CGTTATCCTT | TAGTAGATGG | CCAAGGTAAC | TTTGGTTCTG | TAGATGGAGA | TAGCCCCGCT | 240 |
| GCCATGCGTT | ATACGGAGGC | TCGTCTAAAC | AAGTTGGGTG | AAGCGATGAT | GGATGACCTG | 300 |
| TATAAGGAAA | CTGTAGACTT | CGAACCTAAC | TTTGATAATA | CGTTGACAGA | GCCGAAGGTG | 360 |
| ATGCCGACCC | GTATTCCTAA | TCTTTTGGTT | AATGGTGCTT | CCGGTATTGC | AGTGGGTATG | 420 |
| GCG | | | | | | 423 |

( 2 ) INFORMATION FOR SEQ ID NO:38:

( i ) SEQUENCE CHARACTERISTICS:
     ( A ) LENGTH: 423 base pairs
     ( B ) TYPE: nucleic acid
     ( C ) STRANDEDNESS: double
     ( D ) TOPOLOGY: Not Relevant ( i i ) MOLECULE TYPE: other nucleic acid
     ( A ) DESCRIPTION: /desc ="GyrA gene segment"

( i i i ) HYPOTHETICAL: NO ( i v ) ANTI-SENSE: NO ( v i ) ORIGINAL SOURCE:
     ( A ) ORGANISM: Bacteroides ureolyticus ( x i ) SEQUENCE DESCRIPTION: SEQ ID NO:38:

| | | | | | | |
|---|---|---|---|---|---|---|
| GACGGGTTTA | AGCCCGTGCA | TAGAAGGATA | CTTTATGCTA | TGAATGACTT | GGGTGTTGGA | 60 |

| | | | | | | |
|---|---|---|---|---|---|---|
| AGTAGAAGTC | CATATAAAAA | ATCAGCCCGT | ATCGTAGGAG | ATGTTATTGG | TAAGTACCAC | 120 |
| CCACATGGTG | ATACTGCAGT | TTATGATGCA | TTAGTTAGAA | TGGCTCAGCC | TTTTAGTATG | 180 |
| AGAATAACAA | CTGTCGATGG | ACAAGGAAAC | TTTGGTTCTG | TTGATGGCGA | TCCTGCTGCT | 240 |
| GCTATGCGTT | ATACAGAAGC | TAGAATGACA | AATTTAGCAG | AAGAGCTTTT | AAAAGACTTA | 300 |
| GATAAAGAAA | CTGTTGATTT | TACACCAAAT | TATGATGGAA | GCATGAGTGA | GCCAGATGTT | 360 |
| TTACCAGCAC | GCGTTCCAAA | TTTGTTATTA | AATGGCTCAA | GTGGTATCGC | GGTCGGTATG | 420 |
| GCA | | | | | | 423 |

(2) INFORMATION FOR SEQ ID NO:39:

(i) SEQUENCE CHARACTERISTICS:
        (A) LENGTH: 423 base pairs
        (B) TYPE: nucleic acid
        (C) STRANDEDNESS: double
        (D) TOPOLOGY: Not Relevant (ii) MOLECULE TYPE: other nucleic acid
        (A) DESCRIPTION: /desc ="gyrA gene segment"

(iii) HYPOTHETICAL: NO (iv) ANTI-SENSE: NO (vi) ORIGINAL SOURCE:
        (A) ORGANISM: Borrelia anserina (xi) SEQUENCE DESCRIPTION: SEQ ID NO:39:

| | | | | | | |
|---|---|---|---|---|---|---|
| GATGGGTTCA | AGCCTGTCCA | CAGAAGGATT | CTTTATTCAA | TGCACGAAAT | GGGGCTTAGG | 60 |
| TCTGAAAAGG | CATTTAAGAA | AGCTGGAAGA | ATCGTTGGAG | ATGTTCTTGG | TAAATATCAT | 120 |
| CCTCATGGTG | ATCAATCTAT | TTATGAAGCA | CTTGTGAGGC | TTGCACAAGA | TTTTTCTTTA | 180 |
| AGATACCCTA | TAGTAAGTGG | ACAGGGAAAT | TTTGGTTCTA | TTGATGGTGA | CCCTCCTGCC | 240 |
| GCTATGAGGT | ATACTGAAGC | TCGAATGGCA | AAAATAGCTG | AGGAGCTTGT | TAGAGATATA | 300 |
| GATAAGCAAA | CTGTTGATTT | TAAAGCCAAT | TATGATGATT | CTTTGCTTGA | GCCTGAAGTT | 360 |
| TTGCCAGCTG | CTTTTCCATT | TCTATTAGTC | AACGGTTCTA | GTGGTATAGC | GGTAGGTATG | 420 |
| GCG | | | | | | 423 |

(2) INFORMATION FOR SEQ ID NO:40:

(i) SEQUENCE CHARACTERISTICS:
        (A) LENGTH: 396 base pairs
        (B) TYPE: nucleic acid
        (C) STRANDEDNESS: double
        (D) TOPOLOGY: Not Relevant (ii) MOLECULE TYPE: other nucleic acid
        (A) DESCRIPTION: /desc ="ParC gene segment"

(iii) HYPOTHETICAL: NO (iv) ANTI-SENSE: NO (vi) ORIGINAL SOURCE:
        (A) ORGANISM: Borrelia anserina (xi) SEQUENCE DESCRIPT

| CGGTTAACTC | CTTTGGCATT | TGAGGTACTT | TATAGCAAGG | AATAACATC | TTATGAACCT | 300 |
| TCTTATGATG | GTCGAAATGA | TGAACCTTTA | ATTTTTCCTG | CCAAAATTCC | TGTAATACTT | 360 |
| GTTCAGGGGA | GTGAAGGTAT | CGCCGTCGGT | ATGGCG |  |  | 396 |

( 2 ) INFORMATION FOR SEQ ID NO:41:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="gyrA gene segment"

( i i i ) HYPOTHETICAL: NO ( i v ) ANTI-SENSE: NO ( v i ) ORIGINAL SOURCE:
        ( A ) ORGANISM: Borrelia burgdorferi ( x i ) SEQUENCE DESCRIPTION: SEQ ID NO:41:

| GATGGTCTTA | AACCAGTTCA | CAGGAGAATA | CTTTATTCTA | TGTATGAGAT | GGGACTTCGT | 60 |
| TCTGATAAGG | CTTTTAAAAA | AGCTGGTAGA | ATAGTGGGAG | ATGTTCTTGG | GAAATATCAT | 120 |
| CCTCATGGAG | ATCAATCAAT | TTATGATGCT | CTTGTAAGAC | TTGCTCAGGA | TTTTTCTCTT | 180 |
| AGATATCCCG | TAATACGGGG | ACAGGGAAAT | TTTGGATCTA | TTGACGGAGA | TCCCCCCGCT | 240 |
| GCTATGAGAT | ATACTGAAGC | TAAAATGGAA | AAAATAACTG | AATATATTGT | TAAGGATATA | 300 |
| GACAAAGAGA | CTGTTAATTT | TAAGTCTAAT | TATGACGATT | CTTTAAGTGA | GCCTGAGATT | 360 |
| ATGCCGTCAT | CATTTCCATT | TCTTTTGGTA | AATGGCTCTA | GTGGAATTGC | TGTTGGAATG | 420 |
| GCT |  |  |  |  |  | 423 |

( 2 ) INFORMATION FOR SEQ ID NO:42:

( i ) SEQUENCE CHARACTERISTICS:
        ( A ) LENGTH: 173 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="gyrB gene segment"

( i i i ) HYPOTHETICAL: NO ( i v ) ANTI-SENSE: NO ( v i ) ORIGINAL SOURCE:
        ( A ) ORGANISM: Borrelia burgdorferi ( x i ) SEQUENCE DESCRIPTION: SEQ ID NO:42:

| AAAAGGCCTG | GCATGTATAT | AGGCTCAGTT | TCTATTAATG | GATTGCACCA | TTTGGTTTAT | 60 |
| GAGGTGGTTG | ACAATAGCAT | TGATGAGGCT | TTAGCTGGGT | TTTGTGATAG | AATAGATGTT | 120 |
| ATTATCAATT | TAGATAATAC | TATAACTGTA | ATTGATAATG | GGAGAGGTAT | TCC | 173 |

( 2 ) INFORMATION FOR SEQ ID NO:43:

( i ) SEQUENCE CHARACTERISTICS:
        ( A ) LENGTH: 396 base pairs
        ( B ) TYPE: nucleic acid
        ( C ) STRANDEDNESS: double
        ( D ) TOPOLOGY: Not Relevant ( i i ) MOLECULE TYPE: other nucleic acid (A) DESCRIPTION: /desc ="parC gene segment"

(iii) HYPOTHETICAL: NO (iv) ANTI-SENSE: NO (vi) ORIGINAL SOURCE:
(A) ORGANISM: Borrelia burgdorferi (xi) SEQUENCE DESCRIPTION: SEQ ID NO:43:

| | | | | | |
|---|---|---|---|---|---|
| GATGGGTTTA | AACCAGTTCA | AAGGAGAATT | ATACATTCTC | TTTTTGAAAT | GCATGATGGC | 60 |
| AACTTTCATA | AAGTTGCAAA | TGTTGTTGGT | AATACAATGA | AATATCATCC | CCACGGCGAT | 120 |
| ACGTCAATTT | ATGAGGCTCT | TGTTAATATT | GCCAATAAGG | ATCTATTTAT | TGAAAAGCAG | 180 |
| GGCAATTTTG | GCAATTTATT | CACAGGTGAT | CCTGCTTCTG | CTTCTAGATA | TATTGAATGT | 240 |
| AGGCTAACTC | CCTTAGCCTT | TGATGTTCTT | TACAGCAAAG | AGATAACAAT | TTATGAATCT | 300 |
| TCTTATGATG | GAAGAAATAA | TGAACCTTTG | CTTTATCCTG | CCAAAATTCC | TGTTATTTTA | 360 |
| ATTCAAGGAA | GTGAGGGAAT | TGCTGTTGGA | ATGGCA | | | 396 |

(2) INFORMATION FOR SEQ ID NO:44:

(i) SEQUENCE CHARACTERISTICS:
(A) LENGTH: 188 base pairs
(B) TYPE: nucleic acid
(C) STRANDEDNESS: double
(D) TOPOLOGY: Not Relevant (ii) MOLECULE TYPE: other nucleic acid
(A) DESCRIPTION: /desc ="parE gene segment"

(iii) HYPOTHETICAL: NO (iv) ANTI-SENSE: NO (vi) ORIGINAL SOURCE:
(A) ORGANISM: Borrelia burgdorferi (xi) SEQUENCE DESCRIPTION: SEQ ID NO:44:

| | | | | | |
|---|---|---|---|---|---|
| AGATTAAGAT | CTGGTATGTA | TATTGGACGT | TTGGGAGATG | GCTCTAATAT | TGATGATGGT | 60 |
| ATTTATGTTT | TAATTAAAGA | GATAATAGAC | AATTCAATTG | ATGAGTTTAT | TATGGGTTAC | 120 |
| GGAAATGAAA | TTTTTATAAA | AAAAGAAAAT | AATCTTATTT | CTATTAGGGA | TTATGGAAGA | 180 |
| GGAATTCC | | | | | | 188 |

(2) INFORMATION FOR SEQ ID NO:45:

(i) SEQUENCE CHARACTERISTICS:
(A) LENGTH: 423 base pairs
(B) TYPE: nucleic acid
(C) STRANDEDNESS: double
(D) TOPOLOGY: Not Relevant (ii) MOLECULE TYPE: other nucleic acid
(A) DESCRIPTION: /desc ="gyrA gene segment"

(iii) HYPOTHETICAL: NO (iv) ANTI-SENSE: NO (vi) ORIGINAL SOURCE:
(A) ORGANISM: Borrelia coriaceae (xi)

```
AGATATCCGA TAGTAACTGG ACAGGGCAAT TTTGGTTCTA TTGATGGCGA TCCTCCTGCT      240

GCTATGAGAT ATACTGAAGC TCGAATGGCC AAAATAGCTG AGGAGCTTGT TAGGGATATA      300

GATAGACAAA CTGTTGATTT TAGAGCCAAT TATGATGATT CTTTATTTGA GCCTGAAGTT      360

TTGCCAGCTG CTTTTCCATT TCTTTTAGTT AATGGTTCTA GTGGGATAGC AGTAGGTATG      420

GCG                                                                   423
```

( 2 ) INFORMATION FOR SEQ ID NO:46:

( i ) SEQUENCE CHARACTERISTICS:
        ( A ) LENGTH: 396 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="parC gene segment"

( i i i ) HYPOTHETICAL: NO ( i v ) ANTI-SENSE: NO ( v i ) ORIGINAL SOURCE:
        ( A ) ORGANISM: Borrelia coriaceae ( x i ) SEQUENCE DESCRIPTION: SEQ ID NO:46:

```
GATGGGCTAA AGCCCGTTCA GAGACGAATC ATACATTCTC TTTTTGAGAT GAATGATGGT       60

AATTTTCATA AGGTTGCAAA TGTTGTTGGA AATACAATGA AATATCATCC GCATGGAGAT      120

ACTTCAATTT ATGAAGCACT TGTTAATATG GCAAATAAAG ATTTATTTAT TGAAAAGCAA      180

GGGAATTTTG GTAATCTTTT AACAGGAGAT CCTGCTTCTG CATCGCGTTA TATTGAATGT      240

CGATTAACCC CGCTAGCATT TGAAGTGCTT TATAGCAAGG AAATAACCTC TTATGAAGCT      300

TCTTATGATG GTCGTAATTA TGAACCTTTG ATTTTCCTG CCAAGATTCC TGTAATACTT       360

ATTCAAGGGA GTGAGGGAAT AGCAGTTGGT ATGGCG                                396
```

( 2 ) INFORMATION FOR SEQ ID NO:47:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="gyrA gene segment"

( i i i ) HYPOTHETICAL: NO ( i v ) ANTI-SENSE: NO ( v i ) ORIGINAL SOURCE:
        ( A ) ORGANISM: Borrelia crocidurae ( x i ) SEQUENCE DESCRIPTION: SEQ ID NO:47:

```
GATGGGTTAA AGCCAGTACA CAGAAGAATT TTATATTCAA TGCATGAAAT GGGTCTTAAG       60

TCTGATAAGT CGTTTAAGAA GGCTGGGCGG ATTGTTGGAG ATGTTCTTGG TAAGTATCAT      120

CCTCATGGTG ATCAGTCAAT TTATGAGGCT CTTGTAAGGC TTGCACAGGA TTTTTCGTTA      180

AGATATCCTA TAGTTAGTGG ACAGGGAAAT TTTGGTTCTA TTGATGGCGA TCCTCCTGCT      240

GCTATGCGAT ATACTGAAGC TCGAATGGCA AAAATAGCAG AAGAACTCGT TATAGATATA      300

GATAAACAAA CTGTTAATTT TAAGCCCAAT TATGATGATT CTTTGCTTGA ACCTGAGGTT      360

TTACCAGCAG CTTTTCCATT TCTTTTAGTT AATGGTTCTA GTGGGATCGC AGTGGGTATG      420
```

GCG                                                                                                                                  423

( 2 ) INFORMATION FOR SEQ ID NO:48:

( i ) SEQUENCE CHARACTERISTICS:
        ( A ) LENGTH: 396 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="parC gene segment"

( i i i ) HYPOTHETICAL: NO ( i v ) ANTI-SENSE: NO ( v i ) ORIGINAL SOURCE:
        ( A ) ORGANISM: Borrelia crocidurae ( x i ) SEQUENCE DESCRIPTION: SEQ ID NO:48:

```
GATGGGTTTA   AGCCCGTTCA   GAGACGAATA   ATACATTCTC   TTTTTGAAAT   GAATGATGGT        60

AATTTTCATA   AAGTTGCAAA   TGTTGTTGGA   AATACAATGA   AATATCATCC   TCATGGAGAT       120

ACTTCAATTT   ATGAAGCTCT   TGTTAATATG   GCAAATAAAG   ATTTATTTAT   TGAAAAGCAA       180

GGAAATTTTG   GTAATCTTTT   AACGGGTGAT   CCTGCTTCTG   CATCTCGTTA   TATTGAATGT       240

CGATTAACTC   CTTTAGCGTT   TGAAGTGCTC   TATAGTAAGG   AAATAACGAC   TTATGAGCCT       300

TCTTATGATG   GTCGTAATGC   TGAGCCTTTG   ATTTTCCTG    CTAAAATTCC   TGTAATACTT       360

ATTCAGGGAA   GTGAAGGGAT   CGCGGTCGGT   ATGGCG                                    396
```

( 2 ) INFORMATION FOR SEQ ID NO:49:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="gyrA gene segment"

( i i i ) HYPOTHETICAL: NO ( i v ) ANTI-SENSE: NO ( v i ) ORIGINAL SOURCE:
        ( A ) ORGANISM: Borrelia hermsii ( x i ) SEQUENCE DESCRIPTION: SEQ ID NO:49:

```
GATGGGTTTA   AACCGGTGCA   CAGAAGAATC   CTTTATTCAA   TGCATGAAAT   GGGACTTAGG        60

GCTGATAAGG   CATTTAAGAA   GGCTGGACGA   ATCGTTGGAG   ATGTTCTTGG   TAAATACCAT       120

CCCCATGGTG   ATCAGTCGAT   TTACGAAGCA   CTTGTAAGGC   TTGCACAGGA   TTTTTCTTTA       180

AGATACCCTA   TAGTAATCGG   ACAGGAAAT   TTTGGTTCTA   TTGATGGCGA   CCCTCCTGCT       240

GCTATGAGGT   ATACTGAAGC   TCGAATGGCA   AGAGTAGCTG   AAGAGCTTGT   TAGAGATATA       300

GATAAGCAAA   CTGTTGATTT   TAGAGCCAAT   TATGATGATT   CTTGCTTGA    GCCTGAAGTT       360

TTGCCAGCTG   CTTTTCCATT   TCTATTAGTC   AATGGTTCTA   GTGGCATCGC   CGTGGGTATG       420

GCA                                                                              423
```

( 2 ) INFORMATION FOR SEQ ID NO:50:

( i ) SEQUENCE CHARACTERISTICS:
        ( A ) LENGTH: 396 base pairs (B) TYPE: nucleic acid
(C) STRANDEDNESS: double
(D) TOPOLOGY: Not Relevant (ii) MOLECULE TYPE: other nucleic acid
(A) DESCRIPTION: /desc ="parC gene segment"

(iii) HYPOTHETICAL: NO (iv) ANTI-SENSE: NO (vi) ORIGINAL SOURCE:
(A) ORGANISM: Borrelia hermsii (xi) SEQUENCE DESCRIPTION: SEQ ID NO:50:

| | | | | | | |
|---|---|---|---|---|---|---|
| GACGGGTTTA | AGCCAGTGCA | GAGACGGATC | ATACATTCTC | TTTTTGAGAT | GAATGATGGT | 60 |
| AATTTCCATA | AGGTTGCAAA | TGTTGTTGGA | AATGCAATGA | AATACCATCC | CCATGGAGAC | 120 |
| ACCTCAATTT | ATGAAGCACT | TGTTAATATG | GCAAATAAGG | ATTTATTTAT | TGAAAAACAA | 180 |
| GGAAATTTTG | GTAATCTTTT | AACGGGTGAC | CCCGCTTCTG | CATCGCGTTA | TATTGAATGT | 240 |
| CGATTAACTC | CCCTGGCATT | TGATGTGCTT | TATAGCAAGG | AAATAACATC | TTATGAGCCT | 300 |
| TCTTATGATG | GCCGTAATAA | TGAACCTTTG | ATTTTCCTG | CTAAAATTCC | TGTAATACTT | 360 |
| ATTCAGGGAA | GTGAAGGGAT | CGCGGTCGGT | ATGGCA | | | 396 |

(2) INFORMATION FOR SEQ ID NO:51:

(i) SEQUENCE CHARACTERISTICS:
(A) LENGTH: 423 base pairs
(B) TYPE: nucleic acid
(C) STRANDEDNESS: double
(D) TOPOLOGY: Not Relevant (ii) MOLECULE TYPE: other nucleic acid
(A) DESCRIPTION: /desc ="gyrA gene segment"

(iii) HYPOTHETICAL: NO (iv) ANTI-SENSE: NO (vi) ORIGINAL SOURCE:
(A) ORGANISM: Borrelia parkeri (xi) SEQUENCE DESCRIPTION: SEQ ID NO:51:

| | | | | | | |
|---|---|---|---|---|---|---|
| GATGGGTTAA | AGCCCGTCC (i v) ANTI-SENSE: NO (v i) ORIGINAL SOURCE:
    (A) ORGANISM: Borrelia parkeri (x i) SEQUENCE DESCRIPTION: SEQ ID NO:52:

| | | | | | | |
|---|---|---|---|---|---|---|
| GATGGGTTCA | AGCCTGTACA | GAGACGAATC | ATACATTCTC | TTTTTGAGAT | GAATGATGGC | 60 |
| AATTTTCATA | AAGTTGCAAA | TGTTGTTGGA | AATACAATGA | AATATCATCC | CCATGGTGAT | 120 |
| ACTTCAATTT | ATGAAGCACT | TGTTAATATG | GCAATAAGG | ATTTATTTAT | TGAAAAGCAA | 180 |
| GGAAATTTTG | GTAATCTTTT | AACAGGAGAT | CCTGCTTCTG | CATCGCGTTA | CATTGAATGT | 240 |
| CGATTAACTC | CTCTAGCGTT | TGAAGTGCTT | TATAGCAAGG | AAATAACCTC | TTATGAACCT | 300 |
| TCTTATGATG | GTCGCAATGA | TGAACCTTTA | ATTTTTCCTG | CTAAAATTCC | TGTAATACTT | 360 |
| GTTCAGGGAA | GTGAAGGGAT | AGCAGTGGGT | ATGGCG | | | 396 |

(2) INFORMATION FOR SEQ ID NO:53:

(i) SEQUENCE CHARACTERISTICS:
        (A) LENGTH: 423 base pairs
        (B) TYPE: nucleic acid
        (C) STRANDEDNESS: double
        (D) TOPOLOGY: Not Relevant (i i) MOLECULE TYPE: other nucleic acid
        (A) DESCRIPTION: /desc ="gyrA gene segment"

(i i i) HYPOTHETICAL: NO (i v) ANTI-SENSE: NO (v i) ORIGINAL SOURCE:
        (A) ORGANISM: Borrelia turicatae (x i) SEQUENCE DESCRIPTION: SEQ ID NO:53:

| | | | | | | |
|---|---|---|---|---|---|---|
| GATGGGTTTA | AACCAGTACA | CAGAAGAATC | CTTTATTCAA | TGCATGAAAT | GGGACTTAGG | 60 |
| GCTGATAAAG | CATTTAAGAA | GGCTGGAAGA | ATTGTTGGAG | ATGTTCTTGG | TAAATATCAT | 120 |
| CCTCATGGTG | ATCAGTCAAT | TTATGAAGCA | CTTGTAAGAC | TTGCACAGGA | TTTTTCGTTA | 180 |
| AGATATCCTA | TAGTAAGCGG | ACAGGGAAAT | TTTGGTTCTA | TTGATGGAGA | CCCTCCTGCT | 240 |
| GCTATGAGGT | ATACTGAAGC | TCGAATGGCA | AAAATAGCTG | AAGAGCTTGT | TAAAGATATC | 300 |
| GATAGGCAAA | CTGTTGATTT | TAGAGCCAAT | TATGATGATT | CTTTGCTTGA | GCCTGAAGTT | 360 |
| TTACCAGCTG | CTTTTCCATT | TCTCTTGGTT | AACGGTTCTA | GTGGTATCGC | AGTGGGTATG | 420 |
| GCG | | | | | | 423 |

(2) INFORMATION FOR SEQ ID NO:54:

(i) SEQUENCE CHARACTERISTICS:
        (A) LENGTH: 396 base pairs
        (B) TYPE: nucleic acid
        (C) STRANDEDNESS: double
        (D) TOPOLOGY: Not Relevant (i i) MOLECULE TYPE: other nucleic acid
        (A) DESCRIPTION: /desc ="parC gene segment"

(i i i) HYPOTHETICAL: NO (i v) ANTI-SENSE: NO (v i) ORIGINAL SOURCE:
        (A) ORGANISM: Borrelia turicatae (x i) SEQUENCE DESCRIPTION: SEQ ID NO:54:

-continued

| | | | | | | |
|---|---|---|---|---|---|---|
| GATGGGTTCA | AGCCCGTCCA | GAGACGAATC | ATACATTCTC | TTTTTGAGAT | GAATGATGGT | 60 |
| AATTTTCATA | AAGTTGCAAA | TGTTGTTGGA | AATACAATGA | AATATCATCC | CCATGGCGAT | 120 |
| ACTTCAATTT | ATGAAGCACT | TGTTAATATG | GCAAACAAGG | ATTTATTTAT | TGAAAAGCAA | 180 |
| GGAAATTTTG | GTAATCTTTT | AACAGGAGAT | CCTGCTTCTG | CATCGCGTTA | CATTGAATGT | 240 |
| CGATTAACCC | CTCTAGCATT | TGAAGTGCTT | TATAGCAAGG | AAATAACCTC | TTATGAACCT | 300 |
| TCTTATGATG | GTCGCAATGA | TGAACCTTTA | ATTTTTCCTG | CTAAAATTCC | TGTTATACTT | 360 |
| GTTCAGGGAA | GTGAAGGGAT | TGCAGTTGGT | ATGGCG | | | 396 |

( 2 ) INFORMATION FOR SEQ ID NO:55:

( i ) SEQUENCE CHARACTERISTICS:
( A ) LENGTH: 423 base pairs
( B ) TYPE: nucleic acid
( C ) STRANDEDNESS: double
( D ) TOPOLOGY: Not Relevant ( i i ) MOLECULE TYPE: other nucleic acid
( A ) DESCRIPTION: /desc ="gyrA gene segment"

( i i i ) HYPOTHETICAL: NO ( i v ) ANTI-SENSE: NO ( v i ) ORIGINAL SOURCE:
( A ) ORGANISM: Campylobacter jejuni ( x i ) SEQUENCE DESCRIPTION: SEQ ID NO:55:

| | | | | | | |
|---|---|---|---|---|---|---|
| GATGGTTTAA | AGCCTGTTCA | TAGAAGAATT | TTATATGCTA | TGCAAAATGA | TGAGGCAAAA | 60 |
| AGTAGAACAG | ATTTTGTCAA | ATCAGCCCGT | ATAGTGGGTG | CTGTTATAGG | TCGTTATCAC | 120 |
| CCACATGGAG | ATACAGCAGT | TTATGATGCT | TTGGTTAGAA | TGGCTCAAGA | TTTTTCTATG | 180 |
| AGATATCCAA | GTATTACAGG | ACAAGGCAAC | TTTGGATCTA | TAGATGGTGA | TAGTGCCGCT | 240 |
| GCGATGCGTT | ATACTGAAGC | AAAAATGAGT | AAACTTTCTC | ATGAGCTTTT | AAAAGATATA | 300 |
| GATAAAGATA | CGGTCGATTT | TGTTCCAAAT | TATGATGGTT | CAGAAAGCGA | ACCTGATGTT | 360 |
| TTACCTTCTA | GGGTTCCAAA | TTTATTATTA | AATGGTTCAA | GTGGTATAGC | TGTAGGTATG | 420 |
| GCG | | | | | | 423 |

( 2 ) INFORMATION FOR SEQ ID NO:56:

( i ) SEQUENCE CHARACTERISTICS:
( A ) LENGTH: 423 base pairs
( B ) TYPE: nucleic acid
( C ) STRANDEDNESS: double
( D ) TOPOLOGY: Not Relevant ( i i ) MOLECULE TYPE: other nucleic acid
( A ) DESCRIPTION: /desc ="gyrA gene segment"

( i i i ) HYPOTHETICAL: NO ( i v ) ANTI-SENSE: NO ( v i ) ORIGINAL SOURCE:
( A ) ORGANISM: Chlamydia psittaci ( x i ) SEQUENCE DESCRIPTION: SEQ ID NO:56:

| | | | | | | |
|---|---|---|---|---|---|---|
| GATGGGTTGA | AGCCGGTGCA | AAGGCGTATT | CTTTATGCAA | TGAAGCAATT | AAACCTCACT | 60 |
| CCTGGTGCGA | AAGCTCGTAA | ATGCGCTAAA | ATTTGCGGTG | ATACTTCCGG | AGATTACCAT | 120 |
| CCTCATGGAG | AGAGCGTTAT | TTATCCTACG | TTAGTGCGTA | TGGCTCAAAA | CTGGGCGATG | 180 |
| CGTTATCCAC | TGGTCGATGG | TCAAGGAAAC | TTTGGCTCTA | TTGATGGGGA | CCCTGCGGCT | 240 |

| GCTATGCGTT | ATACGGAAGC | TCGTTTAACC | CATAGTGCGA | TCTTCCTAAT | GGAAGATTTA | 300 |
| GATAAAGATA | CTGTAGATAT | GGTATCTAAC | TATGACGAAA | CGAAGCACGA | GCCTGTTGTT | 360 |
| TTTCCTTCGA | AGTTTCCTAA | TCTTCTTTGT | AACGGTTCCT | CTGGAATCGC | AGTCGGTATG | 420 |
| GCA | | | | | | 423 |

( 2 ) INFORMATION FOR SEQ ID NO:57:

( i ) SEQUENCE CHARACTERISTICS:
        ( A ) LENGTH: 174 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="gyrB gene segment"

( i i i ) HYPOTHETICAL: NO ( i v ) ANTI-SENSE: NO ( v i ) ORIGINAL SOURCE:
        ( A ) ORGANISM: Chlamydia psittaci ( x i ) SEQUENCE DESCRIPTION: SEQ ID NO:57:

| AAGCGGCCGG | GGATGTACAT | AGGAGATACT | GGGATCACAG | GGCTTCATCA | CTTAGTGT (A) DESCRIPTION: /desc ="gyrA gene segment"

(iii) HYPOTHETICAL: NO (iv) ANTI-SENSE: NO (vi) ORIGINAL SOURCE:
　　(A) ORGANISM: Chlamydia trachomatis (xi) SEQUENCE DESCRIPTION: SEQ ID NO:59:

| | | | | | | |
|---|---|---|---|---|---|---|
| GACGGATTAA | AACCTTCTCA | GCGACGTATT | TTATACGCTA | TGAAACAATT | AAATCTGACT | 60 |
| CCAGGAGCAA | AGCACAGAAA | ATGCGCAAAA | ATTTGCGGTG | ATACTTCCGG | AGATTATCAC | 120 |
| CCTCATGGAG | AAAGTGTCAT | TTATCCTACT | TTAGTAAGGA | TGGCACAGGA | TTGGGCCATG | 180 |
| CGATACCCTC | TTGTTGATGG | TCAAGGGAAT | TTTGGATCCA | TCGACGGGGA | TCCAGCTGCT | 240 |
| GCCATGCGAT | ATACAGAGGC | TCGCCTGACT | CAGAGCGCTA | TCTTTTGTT | AGAGGACCTA | 300 |
| GATAAAGATA | CTGTAGATAT | GGTCCCTAAC | TACGATGAAA | CTAAATATGA | ACCTGTAGTT | 360 |
| TTTCCTTCAA | AATTCCCTAA | TTTACTTTGT | AATGGCTCCT | CAGGCATCGC | AGTCGGTATG | 420 |
| GC | | | | | | 422 |

(2) INFORMATION FOR SEQ ID NO:60:

(i) SEQUENCE CHARACTERISTICS:
　　　　(A) LENGTH: 174 base pairs
　　　　(B) TYPE: nucleic acid
　　　　(C) STRANDEDNESS: double
　　　　(D) TOPOLOGY: Not Relevant (ii) MOLECULE TYPE: other nucleic acid
　　　　(A) DESCRIPTION: /desc ="gyrB gene segment"

(iii) HYPOTHETICAL: NO (iv) ANTI-SENSE: NO (vi) ORIGINAL SOURCE:
　　　　(A) ORGANISM: Chlamydia trachomatis (xi) SEQUENCE DESCRIPTION: SEQ ID NO:60:

| | | | | | | |
|---|---|---|---|---|---|---|
| GAGCGTCCTG | GAATGTACAT | TGGTGATACA | GGAGTTACCG | GATTGCATCA | CTTGGTTTAT | 60 |
| GAAGTGGTGG | ATAACAGTAT | CGATGAGGCA | ATGGCGGGTT | TTTGTACCGA | GGTCGTTGTT | 120 |
| CGCATATTGG | AAGACGGAGG | TATTTCTATT | TCGGATAACG | GTCGAGGAAT | TCCT | 174 |

(2) INFORMATION FOR SEQ ID NO:61:

(i) SEQUENCE CHARACTERISTICS:
　　　　(A) LENGTH: 396 base pairs
　　　　(B) TYPE: nucleic acid
　　　　(C) STRANDEDNESS: double
　　　　(D) TOPOLOGY: Not Relevant (ii) MOLECULE TYPE: other nucleic acid
　　　　(A) DESCRIPTION: /desc ="parC gene segment"

(iii) HYPOTHETICAL: NO (iv) ANTI-SENSE: NO (vi) ORIGINAL SOURCE:
　　　　(A) ORGANISM: Chlamydia trachomatis (xi) SEQUENCE DESCRIPTION: SEQ ID NO:61:

| | | | | | | |
|---|---|---|---|---|---|---|
| GATGGCCTCA | AGCCTGTTCA | AGAAGGCTT | CTTTGGACCT | TATTCCGCAT | GGATGATGGT | 60 |
| AAAATGCATA | AGGTGGCTAA | TATCGCAGGA | CGTACGATGG | CGCTGCACCC | GCATGGTGAT | 120 |
| GCGCCTATCG | TGGAAGCTCT | TGTCGTTTTG | GCAAATAAAG | GGTTCCTGAT | AGAGACACAA | 180 |

```
GGGAACTTTG  GTAACCCTCT  CACAGGAGAT  CCTCATGCAG  CGGCTCGTTA  TATAGAAGCG    240

CGGCTAAGCC  CTTTAGCTAA  GGAGGTACTT  TTTAATACGG  ATCTCATGAC  CTTCCATGAT    300

TCTTACGATG  GAAGAGAGCA  AGAACCCGAT  ATCTTAGCTG  CAAAGATTCC  TCTACTACTC    360

CTTCATGGCG  TGGATGGAAT  CGCCGTCGGT  ATGGCA                                396
```

( 2 ) INFORMATION FOR SEQ ID NO:62:

( i ) SEQUENCE CHARACTERISTICS:
        ( A ) LENGTH: 189 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="parE gene segment"

( i i i ) HYPOTHETICAL: NO ( i v ) ANTI-SENSE: NO ( v i ) ORIGINAL SOURCE:
        ( A ) ORGANISM: Chlamydia trachomatis ( x i ) SEQUENCE DESCRIPTION: SEQ ID NO:62:

```
CGCCTACGCG  CGGGAATGTA  TATCGGAAGA  TTAGGCGACG  GATCTCAAGC  TGAAGACGGC     60

ATTTACACGT  TATTTAAAGA  AGTAGTCGAT  AATGCTATTG  ATGAATTTGT  CATGGGATAT    120

GGACATACCA  TCCACATAAC  AGGAGACGCA  CACGAACTGT  CTATTCGTGA  TGAAGGCCGC    180

GGCATTCCC                                                                189
```

( 2 ) INFORMATION FOR SEQ ID NO:63:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="gyrA gene segment"

( i i i ) HYPOTHETICAL: NO ( i v ) ANTI-SENSE: NO ( v i ) ORIGINAL SOURCE:
        ( A ) ORGANISM: Clostridium difficiles ( x i ) SEQUENCE DESCRIPTION: SEQ ID NO:63:

```
GACGGGTTCA  AACCAGTTCA  TAGAAGAATA  TTATATTCAA  TGAGTGAGTT  AAATTTAACT     60

CCAGATAAAC  CATACAGGAA  GTCAGCTCGT  ATTGTTGGGG  ACGTTTTAGG  TAAGTACCAT    120

CCTCATGGAG  ATACTGCTGT  TTATTATGCT  ATGGTAAGAA  TGGCACAAGA  TTTTTCAACT    180

AGAGCACTTT  TAGTAGATGG  TCATGGTAAC  TTTGGTTCTG  TTGATGGGGA  TTCACCAGCT    240

GCTATGCGTT  ATACAGAAGC  TAAAATGAGT  AAATTATCAT  TAGAACTACT  AAGAGATATT    300

GAAAAGGAAA  CTGTAGACTT  TAAACCAAAC  TTTGATGAGT  CGTTAAAAGA  GCCTTCAGTA    360

TTGCCAGCTA  GATATCCTAA  TTTATTAGTA  AATGGCTCAA  ATGGCATCGC  AGTTGGTATG    420

GCA                                                                      423
```

( 2 ) INFORMATION FOR SEQ ID NO:64:

( i ) SEQUENCE CHARACTERISTICS:
        ( A ) LENGTH: 423 base pairs (B) TYPE: nucleic acid
(C) STRANDEDNESS: double
(D) TOPOLOGY: Not Relevant (ii) MOLECULE TYPE: other nucleic acid
(A) DESCRIPTION: /desc ="gyrA gene segment"

(iii) HYPOTHETICAL: NO (iv) ANTI-SENSE: NO (vi) ORIGINAL SOURCE:
(A) ORGANISM: Clostridium perfringens (xi) SEQUENCE DESCRIPTION: SEQ ID NO:64:

| | | | | | | |
|---|---|---|---|---|---|---|
| GACGGGCTGA | A ( i i i ) HYPOTHETICAL: NO ( i v ) ANTI-SENSE: NO ( v i ) ORIGINAL SOURCE:
    ( A ) ORGANISM: Fusobacterium necrophorum ( x i ) SEQUENCE DESCRIPTION: SEQ ID NO:66:

```
GACGGGCTTA AGCCGGTGCA TAGAAGAATT TTATTTGCTA TGAACGAAAT GGGAATGACG      60
AATGATAAAC CTTTTAAAAA ATCCGCAAGA ATTGTTGGGG AAGTTTTGGG AAAATATCAT     120
CCGCACGGAG ATACTGCCGT ATATAATACT ATGGTTAGAA TGGCTCAAGA ATTCAATTAT     180
CGTTATATGT TAGTAGAGGG ACATGGAAAT TTTGGTTCTA TTGATGGAGA TTCCGCTGCA     240
GCGATGAGAT ATACAGAAGC AAGGATGTCA AAAATAACGG CAGAATTACT TGAGGATATT     300
GATAAAAATA CCATCGACTT TCGTAAAAAT TTTGATGATT CCTTAGATGA ACCGACAGTA     360
TTGCCATCTA AACTGCCGCA TTTACTATTG AATGGTTCTA CAGGGATAGC GGTCGGTATG     420
GCA                                                                  423
```

( 2 ) INFORMATION FOR SEQ ID NO:67:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="gyrA gene segment"

( i i i ) HYPOTHETICAL: NO ( i v ) ANTI-SENSE: NO ( v i ) ORIGINAL SOURCE:
        ( A ) ORGANISM: Fusobacterium nucleatum ( x i ) SEQUENCE DESCRIPTION: SEQ ID NO:67:

```
GATGGGTTCA AGCCTGTGCA TAGAAGAATT CTATTTGCAA TGAATGAAAT GGGAATGACT      60
AATGACAAAC CATTTAAGAA ATCTGCCAGA ATCGTTGGAG AAGTTCTAGG TAAGTATCAC     120
CCTCATGGAG ATTCAGCAGT ATATGGAACT ATGGTAAGAA TGGCACAAGA TTTCAACTAT     180
AGGTATTTAC TTGTTGAAGG GCATGGAAAC TTTGGTTCTA TTGATGGAGA TTCAGCAGCA     240
GCAATGAGAT ATACAGAAGC AAGAATGGAA AAGATAACTG CTGAATTATT AGAAGATATA     300
GATAAAGATA CTATTGATTG GAGAAAAAAC TTTGATGACT CCTTAGATGA ACCAACGGTG     360
TTACCAGCTA AGTTACCTAA TTTATTATTA AATGGAGCAA TAGGCATTGC TGTCGGTATG     420
GCA                                                                  423
```

( 2 ) INFORMATION FOR SEQ ID NO:68:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="gyrA gene segment"

( i i i ) HYPOTHETICAL: NO ( i v ) ANTI-SENSE: NO ( v i ) ORIGINAL SOURCE:

(A) ORGANISM: Lactobacillus acidophilus (xi) SEQUENCE DESCRIPTION: SEQ ID NO:68:

| | | | | | |
|---|---|---|---|---|---|
| GACGGGCTCA | AACCTGTGCA | GCGCCGGATT | CTGTATGGCA | TGAATGAACT | CGGGGTCACA | 60 |
| CCGGAGAAGC | CATACAAGAA | GAGTGCGCGG | ATCGTCGGGG | ATGTCATGGG | GAAGTACCAT | 120 |
| CCGCATGGTG | ACAGCTCGAT | TTATGAAGGG | CTTGTGCGGA | TGGCGCAGGA | CTTTAGTTAC | 180 |
| CGGTATATGC | TGGTTGACGG | CCACGGGAAC | TTTGGCTCGG | TTGACGGTGA | CGGTGCGGCG | 240 |
| GCGATGCGTT | ACACCGAAGC | CCGGATGAGT | AAAATTGCCG | TCGAAATGTT | ACGCGACATC | 300 |
| AACAAAGACA | CGATTGATTT | TCAGGATAAT | TACGATGGCA | CCGAAAAAGA | ACCGGTTGTT | 360 |
| TTGCCAGCGC | GCTTCCCGAA | TCTGCTGGTC | AACGGTGCGA | CCGGGATCGC | TGTAGGTATG | 420 |
| GCA | | | | | | 423 |

(2) INFORMATION FOR SEQ ID NO:69:

(i) SEQUENCE CHARACTERISTICS:
(A) LENGTH: 426 base pairs
(B) TYPE: nucleic acid
(C) STRANDEDNESS: double
(D) TOPOLOGY: Not Relevant (ii) MOLECULE TYPE: other nucleic acid
(A) DESCRIPTION: /desc ="gyrA gene segment"

(iii) HYPOTHETICAL: NO (iv) ANTI-SENSE: NO (vi) ORIGINAL SOURCE:
(A) ORGANISM: Legionella pneumophila (xi) SEQUENCE DESCRIPTION: SEQ ID NO:69:

| | | | | | |

| TTTGAGGTTG | TAGATAATTC | AATAGATGAA | TCCCTGGCAG | GTTATTGCAA | GGAAATTTTT | 120 |
| GTTACCATTC | ATAGCGATGA | ATCAATTACC | GTTAAGGATG | ATGGCCGCGG | TATTCCG | 177 |

( 2 ) INFORMATION FOR SEQ ID NO:71:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="parC gene segment"

( i i i ) HYPOTHETICAL: NO ( i v ) ANTI-SENSE: NO ( v i ) ORIGINAL SOURCE:
        ( A ) ORGANISM: Legionella pneumophila ( x i ) SEQUENCE DESCRIPTION: SEQ ID NO:71:

| GATGGGCTGA | AGCCGGTTCA | CAGGCGAGTT | CTTTTGCGA | TGAGTGAGTT | AAGTAATGAT | 60 |
| TGGAATAAGC | CGTATAAAAA | ATCTGCTCGT | GTAGTAGGGG | ATGTCATTGG | TAAATATCAT | 120 |
| CCTCATGGGG | ATACACGTGT | TTATGACACT | ATTGTTCGTA | TGGCTCAGCC | CTTTTCCATG | 180 |
| CGTTATATGC | TGATTGATGG | GCAGGGTAAT | TTTGGCTCTG | TAGATGGAGA | TGCTCCAGCT | 240 |
| GCCATGCGTT | ACACTGAAGT | AAGAATGTCC | AAAGTGGCGC | ATGCTTACT | GGCTGATTTG | 300 |
| GATAAGGAAA | CCGTTGATTT | TAGTCCTAAC | TATGATGAAA | CAGAATTTGC | TCCAGTGGTA | 360 |
| TTGCCATCGA | GAATTCCCAA | TTTACTAGTT | AATGGCTCTT | CCGGCATAGC | CGTCGGTATG | 420 |
| GCA | | | | | | 423 |

( 2 ) INFORMATION FOR SEQ ID NO:72:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="gyrA gene segment"

( i i i ) HYPOTHETICAL: NO ( i v ) ANTI-SENSE: NO ( v i ) ORIGINAL SOURCE:
        ( A ) ORGANISM: Leptonema illini ( x i ) SEQUENCE DESCRIPTION: SEQ ID NO:72:

| GACGGGCTTA | AACCTGTCCA | CCGTCGCATC | CTCTTTGCCA | TGCACGAACG | TGCCTGGAGG | 60 |
| CACGACCGCC | CCTTCGTCAA | ATGCGCGAAG | ATCGTCGGCG | AGGTTATCGG | TAACTTCCAC | 120 |
| CCGCACGGAG | ACGGCGCCGT | TTACGACACG | ATGGTGCGTA | TGGCGCAGGA | CTTCGTGATG | 180 |
| AAGATGCCTC | TGGTCGAAGG | CCAGGGGAAC | TTCGGTTCGA | TCGACGGCGA | CAATGCGGCA | 240 |
| GCCTATCGTT | ATACAGAGGC | CCGACTGACG | CGCGCCGCCG | AAGAGCTTCT | GCGCGACATC | 300 |
| GACAAAAACA | CCGTCGACTT | CAGCCCGAAC | TTCGACGACA | CCAAGCAGGA | ACCTAAGGTT | 360 |
| TTACCGGCAG | GCCTGCCGAA | CCTGCTCATC | AACGGAGCCA | GCGGCATCGC | AGTCGGTATG | 420 |
| GCA | | | | | | 423 |

( 2 ) INFORMATION FOR SEQ ID NO:73:

( i ) SEQUENCE CHARACTERISTICS:
   ( A ) LENGTH: 422 base pairs
   ( B ) TYPE: nucleic acid
   ( C ) STRANDEDNESS: double
   ( D ) TOPOLOGY: Not Relevant ( i i ) MOLECULE TYPE: other nucleic acid
   ( A ) DESCRIPTION: /desc ="gyrA gene segment"

( i i i ) HYPOTHETICAL: NO ( i v ) ANTI-SENSE: NO ( v i ) ORIGINAL SOURCE:
   ( A ) ORGANISM: Leptospira biflexa ( x i ) SEQUENCE DESCRIPTION: SEQ ID NO:73:

| | | | | | | |
|---|---|---|---|---|---|---|
| GACGGGCTGA | AGCCTGTTCA | TAGACGTGTC | CTCCATGCGA | TGAACGAAAG | AGCCTGGAGA | 60 |
| TCTGACAGAC | CTTACGTCAA | GTCGGCAAAG | ATTGTTGGGG | AAGTGATTGG | TAACTATCAC | 120 |
| CCTCATGGTG | ACTCTGCAGT | ATATGAAACA | ATGGTTCGTA | TGGCGCAAAC | TTTTTCCATG | 180 |
| CGAGAGACAT | TGATTGATGG | CCAAGGTAAC | TTTGGATCTG | TCGATGGTGA | CAATGCGGCG | 240 |
| GCATATCGGT | ATACAGAAGC | TCGTCTGACA | AAACTTGCAG | AAGAACTTCT | CAAAGACATC | 300 |
| GAAAAAACA | CAGTAAGTTT | TTCCCCTAAC | TTTGATGATA | CGAGACAACA | ACCTGATGTT | 360 |
| TTACCTGCTA | ATTTTCCAAA | TATTTAGTC | AATGGTTCCA | CAGGAATAGC | TGTCGGTATG | 420 |
| GC | | | | | | 422 |

( 2 ) INFORMATION FOR SEQ ID NO:74:

( i ) SEQUENCE CHARACTERISTICS:
      ( A ) LENGTH: 423 base pairs
      ( B ) TYPE: nucleic acid
      ( C ) STRANDEDNESS: double
      ( D ) TOPOLOGY: Not Relevant ( i i ) MOLECULE TYPE: other nucleic acid
      ( A ) DESCRIPTION: /desc ="gyrA gene segment"

( i i i ) HYPOTHETICAL: NO ( i v ) ANTI-SENSE: NO ( v i ) ORIGINAL SOURCE:
      ( A ) ORGANISM: Leptospira interrogans ( x i ) SEQUENCE DESCRIPTION: SEQ ID NO:74:

| | | | | | | |
|---|---|---|---|---|---|---|
| GATGGGTTGA | AGCCGGTCCA | TAGAAGAATC | CTTCATGCTA | TGAACGAACG | TGCATGGAGA | 60 |
| AGTGATCGTC | CTTTCGTTAA | ATGCGCTAAA | ATTGTTGGGG | AAGTAATCGG | TAATTATCAT | 120 |
| CCTCACGGAG | ACGCATCTGT | TTACGAAGCG | CTTGTGAGAA | TGGTTCAGGA | ATTTTCCTTA | 180 |
| AGAGTTCCTT | TAATTGATGG | ACAAGGAAAT | TTCGGTTCTA | TCGACGGAGA | TAACCCGGCG | 240 |
| GCTTATCGAT | ATACGGAAGC | AAGGCTTGAA | AAAGTCGCCG | AAGAATTATT | ACGCGACATC | 300 |
| GAAAAAGAAA | CGGTTAGTTT | TTCACCTAAC | TATGATGATA | CGAAAGAACA | ACCGGATGTT | 360 |
| TTACCTGCAA | ATTTTCCAAA | CTTACTTGTA | AACGGTTCTT | CTGGCATCGC | CGTCGGTATG | 420 |
| GCA | | | | | | 423 |

( 2 ) INFORMATION FOR SEQ ID NO:75:

( i ) SEQUENCE CHARACTERISTICS:
      ( A ) LENGTH: 423 base pairs
      ( B ) TYPE: nucleic acid
      ( C ) STRANDEDNESS: double
      ( D ) TOPOLOGY: Not Relevant (i i) MOLECULE TYPE: other nucleic acid
    (A) DESCRIPTION: /desc ="gyrA gene segment"

(i i i) HYPOTHETICAL: NO (i v) ANTI-SENSE: NO (v i) ORIGINAL SOURCE:
    (A) ORGANISM: Mycoplasma fermentans (x i) SEQUENCE DESCRIPTION: SEQ ID NO:75:

| | | | | | | |
|---|---|---|---|---|---|---|
| GACGGGCTCA | AGCCGGTCCA | TAGACGTATC | CTTTTTGATA | TGAATGAATT | AGGAATTACA | 60 |
| TTTGGATCGC | AACATAGAAA | AAGCGCTCGT | ATTGTCGGGG | ACGTTTAGG | TAAGTACCAC | 120 |
| CCACATGGCG | ACAGTTCAGT | TTATGAAGCT | ATGGTTCGTA | TGGCGCAAGA | TTTTAGTATG | 180 |
| CGTTATCCTT | TAGTTGATGG | TCACGGTAAC | TTTGGATCTA | TTGATGGTGA | TGAAGCTGCT | 240 |
| GCGATGCGTT | ATACTGAAGC | AAGAATGAGC | AAATTAGCTG | CTGAAATGCT | TGAAGGTATT | 300 |
| AAAAAGATA | CAGTAGATTT | TGTTGATAAC | TATGATGCTA | GTGAAAAAGA | ACCTTCAGTA | 360 |
| TTACCATCAA | GATTCCCTAA | CCTTTTAGTT | TCAGGTGGTA | GTGGCATAGC | TGTCGGTATG | 420 |
| GCA | | | | | | 423 |

(2) INFORMATION FOR SEQ ID NO:76:

(i) SEQUENCE CHARACTERISTICS:
        (A) LENGTH: 423 base pairs
        (B) TYPE: nucleic acid
        (C) STRANDEDNESS: double
        (D) TOPOLOGY: Not Relevant (i i) MOLECULE TYPE: other nucleic acid
        (A) DESCRIPTION: /desc ="parC gene segment"

(i i i) HYPOTHETICAL: NO (i v) ANTI-SENSE: NO (v i) ORIGINAL SOURCE:
        (A) ORGANISM: Mycoplasma fermentans (x i) SEQUENCE DESCRIPTION: SEQ ID NO:76:

| | | | | | | |
|---|---|---|---|---|---|---|
| GATGGGTTAA | AGCCTGTACA | AAGAAGAATT | CTTTATTCTA | TGTATGAATT | AGGTTTGCAA | 60 |
| TGAAATAAAC | CTTTTAAAAA | ATCTGCTCGT | GTTGTTGGTG | ATGTTATTGG | TAAATATCAC | 120 |
| CCACATGGTG | ATAGTTCAAT | TTATGAAGCT | ATGGTTCGTA | TGGCTCAAGA | TTGAAAAATG | 180 |
| GGACATACAC | TTTTAGAAAT | GCATGGGAAT | GTTGGATCTA | TTGATGATGA | CCCTGCAGCT | 240 |
| GCAATGCGTT | ATACTGAAGT | TAGATTAGCT | GCTTAGCTG | ACTTAGTTAT | TGGTGACTTA | 300 |
| AAGAAAAATA | CAGTTAAGTT | TGCTCCTAAC | TTTGATGATA | GTGAAAAAGA | GCCAGTTGTT | 360 |
| TTACCTTCAC | TTATTCCAAA | TTTATTATTA | AATGGGGCTA | AAGGGATAGC | CGTGGGTATG | 420 |
| GCA | | | | | | 423 |

(2) INFORMATION FOR SEQ ID NO:77:

(i) SEQUENCE CHARACTERISTICS:
        (A) LENGTH: 423 base pairs
        (B) TYPE: nucleic acid
        (C) STRANDEDNESS: double
        (D) TOPOLOGY: Not Relevant (i i) MOLECULE TYPE: other nucleic acid
        (A) DESCRIPTION: /desc ="gyrA gene segment"

(i i i) HYPOTHETICAL: NO

-continued ( i v ) ANTI-SENSE: NO ( v i ) ORIGINAL SOURCE:
    ( A ) ORGANISM: Mycoplasma genitalium ( x i ) SEQUENCE DESCRIPTION: SEQ ID NO:77:

| | | | | | | |
|---|---|---|---|---|---|---|
| GATGGGCTCA | AGCCGGTGCA | TCGTCGTGTT | CTTTATGGTG | CTTATATTGG | TGGCATGCAC | 60 |
| CATGATCGTC | CTTTTAAAAA | GTCTGCGAGG | ATTGTTGGTG | ATGTAATGAG | TAAATTCCAC | 120 |
| CCTCATGGTG | ATATGGCAAT | ATATGACACC | ATGTCAAGAA | TGGCTCAAGA | CTTTTCATTA | 180 |
| AGATACCTTT | TAATTGATGG | TCATGGTAAT | TTTGGTTCTA | TAGATGGTGA | TAGACCTGCT | 240 |
| GCACAACGTT | ATACAGAAGC | AAGATTATCT | AAACTTGCAG | CAGAACTTTT | AAAAGATATT | 300 |
| GATAAAGATA | CAGTTGACTT | TATTGCTAAT | TATGATGGTG | AGGAAAAAGA | ACCAACTGTT | 360 |
| CTACCAGCAG | CTTTCCCTAA | CTTACTTGCA | AATGGTTCTA | GTGGCATTGC | AGTCGGTATG | 420 |
| GCA | | | | | | 423 |

( 2 ) INFORMATION FOR SEQ ID NO:78:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="parC gene segment"

( i i i ) HYPOTHETICAL: NO ( i v ) ANTI-SENSE: NO ( v i ) ORIGINAL SOURCE:
        ( A ) ORGANISM: Mycoplasma genitalium ( x i ) SEQUENCE DESCRIPTION: SEQ ID NO:78:

| | | | | | | |
|---|---|---|---|---|---|---|
| GATGGGCTTA | AGCCTGTCCA | AAGACGGATC | TTATATGGGA | TGTTTCAAAT | GGGCTTAAAA | 60 |
| CCCACCACTC | CCTATAAAAA | ATCAGCCCGT | GCTGTTGGGG | AGATCATGGG | GAAATACCAC | 120 |
| CCCCATGGTG | ATAGTTCCAT | TTATGATGCA | ATTATCAGAA | TGTCCCAAAG | CTGAAAGAAC | 180 |
| AACTGAACAA | CTGTTTCTAT | CCATGGTAAC | AATGGTTCAG | TGGATGGGGA | TAATGCTGCA | 240 |
| GCAATGCGTT | ACACAGAAAC | CCGCTTAAGC | TTGTATGGAT | TTGAACTATT | AAAAGACATT | 300 |
| GATAAAAAGT | TAGTTAGTTT | TATCAATAAC | TTTGATGATA | GTGAAAAAGA | ACCAACGGTT | 360 |
| TTACCAACCT | TACTGCCTAA | CCTCTTTATC | AATGGTGCGA | GTGGAATAGC | AGTAGGTATG | 420 |
| GCA | | | | | | 423 |

( 2 ) INFORMATION FOR SEQ ID NO:79:

( i ) SEQUENCE CHARACTERISTICS:
        ( A ) LENGTH: 424 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="gyrA gene segment"

( i i i ) HYPOTHETICAL: NO ( i v ) ANTI-SENSE: NO ( v i ) ORIGINAL SOURCE:
        ( A ) ORGANISM: Mycoplasma incognitus ( x i ) SEQUENCE DESCRIPTION: SEQ ID NO:79:

```
GATGGGCTGA  AACCGGTGCA  TAGACGTATC  CTTTTTGATA  TGAATGAATT  AGGAATTACA      60

TTTGGATCGC  AACATAGAAA  AAGCGCCCGT  ATTGTCGGGG  ACGTTTTAGG  TAAGTACCAC     120

CCACATGGTG  ACAGTTCAGT  TTATGAAGCT  ATGGTTCGTA  TGGCGCAAGA  TTTTAGTATG    180

CGTTATCCTT  TAGTTGATGG  TCACGGTAAC  TTTGGATCTA  TTGATGGTGA  TGAAGCTGCT    240

GCGATGCGTT  ATACTGAAGC  AAGAATGAGC  AAATTAGCTG  CTGAAATGCT  TGAAGGTATT    300

AAAAAGATA   CAGTAGATTT  TGTTGATAAC  TATGATGCTA  GTGAAAAAGA  ACCTTCAGTA    360

TTACCATCAA  GATTCCCTAA  CCTTTTAGTT  TCAGGTGGTA  GTGGCATCGC  TGTCGGTATG    420

GCAT                                                                      424
```

( 2 ) INFORMATION FOR SEQ ID NO:80:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="parC gene segment"

( i i i ) HYPOTHETICAL: NO ( i v ) ANTI-SENSE: NO ( v i ) ORIGINAL SOURCE:
        ( A ) ORGANISM: Mycoplasma incognitus ( x i ) SEQUENCE DESCRIPTION: SEQ ID NO:80:

```
GATGGGTTGA  AACCCGTGCA  AAGAAGAATT  CTTTATTCTA  TGTATGAATT  AGGTTTGCAA     60

TGAAATAAAC  CTTTTAAAAA  ATCTGCTCGT  GTTGTTGGTG  ATGTTATTGG  TAAATATCAC    120

CCACATGGTG  ATAGTTCAAT  TTATGAAGCT  ATGGTTCGTA  TGGCTCAAGA  TTGAAAAATG    180

GGACATACAC  TTTTAGAAAT  GCATGGGAAT  GTTGGATCTA  TTGATGATGA  CCCTGCAGCT    240

GCAATGCGTT  ATACTGAAGT  TAGATTAGCT  GCTTTAGCTG  ACTTAGTTAT  TGGTGACTTA    300

ATGAAAAATA  CAGTTAAGTT  TGCTCCTAAC  TTTGATGATA  GTGAAAAAGA  GCCAGTTGTT    360

TTACCTTCAC  TTATTCCAAA  TTTATTATTA  AATGGGGCTA  AAGGTATCGC  AGTTGGTATG    420

GCA                                                                       423
```

( 2 ) INFORMATION FOR SEQ ID NO:81:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="gyrA gene segment"

( i i i ) HYPOTHETICAL: NO ( i v ) ANTI-SENSE: NO ( v i ) ORIGINAL SOURCE:
        ( A ) ORGANISM: Neisseria gonorrheae ( x i ) SEQUENCE DESCRIPTION: SEQ ID NO:81:

```
GACGGCCTAA  AGCCGGTGCA  CCGGCGCGTA  CTGTACGCGA  TGCACGAGCT  GAAAAATAAC     60

TGGAATGCCG  CCTACAAAAA  ATCGGCGCGC  ATCGTCGGCG  ACGTCATCGG  TAAATACCAC    120

CCCCACGGCG  ATTCCGCAGT  TTACGACACC  ATCGTCCGTA  TGGCGCAAAA  TTTCGCTATG    180
```

| CGTTATGTGC | TGATAGACGG | ACAGGGCAAC | TTCGGATCGG | TGGACGGGCT | TGCCGCCGCA | 240 |
| GCCATGCGCT | ATACCGAAAT | CCGCATGGCG | AAAATCTCAC | ATGAAATGCT | GGCAGACATT | 300 |
| GAGGAAGAAA | CCGTTAATTT | CGGCCCGAAC | TACGACGGTA | GCGAACACGA | GCCGCTTGTA | 360 |
| CTGCCGACCC | GTTTCCCCAC | ACTGCTCGTC | AACGGCTCGT | CCGGTATCGC | CGTCGGTATG | 420 |
| GCG | | | | | | 423 |

( 2 ) INFORMATION FOR SEQ ID NO:82:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="parC gene segment"

( i i i ) HYPOTHETICAL: NO ( i v ) ANTI-SENSE: NO ( v i ) ORIGINAL SOURCE:
        ( A ) ORGANISM: Neisseria gonorrheae ( x i ) SEQUENCE DESCRIPTION: SEQ ID NO:82:

| GACGGCCAAA | AGCCCGTGCA | GCGGCGCATT | TTGTTTGCCA | TGCGCGATAT | GGGTTTGACG | 60 |
| GCGGGGGCGA | AGCCGGTGAA | ATCGGCGCGC | GTGGTCGGCG | AGATTTGGG | TAAATACCAT | 120 |
| CCGCACGGCG | ACAGTTCCGC | CTATGAGGCG | ATGGTGCGCA | TGGCTCAGGA | TTTTACCTTG | 180 |
| CGCTATCCCT | TAATCGACGG | CATCGGCAAC | TTCGGTTCGC | GCGACGGCGA | CGGGCGGCG | 240 |
| GCGATGCGTT | ACACCGAAGC | GCGGCTCACG | CCGATTGCGG | AATTGCTGTT | GTCCGAAATC | 300 |
| AATCAGGGGA | CGGTGGATTT | TATGCCGAAC | TACGACGGCG | CGTTTGACGA | GCCGCTGCAC | 360 |
| CTTCCCGCCC | GCTTGCCTAT | GGTGTTGCTC | AACGGCGCGT | CGGGCATCGC | GGTGGGTATG | 420 |
| GCG | | | | | | 423 |

( 2 ) INFORMATION FOR SEQ ID NO:83:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="gyrA gene segment"

( i i i ) HYPOTHETICAL: NO ( i v ) ANTI-SENSE: NO ( v i ) ORIGINAL SOURCE:
        ( A ) ORGANISM: Pseudomonas aeruginosa ( x i ) SEQUENCE DESCRIPTION: SEQ ID NO:83:

| GACGGGCTGA | AACCTGTGCA | CCGCCGTGTG | CTTTATGCCA | TGAGCGAGCT | GGGCAACGAC | 60 |
| TGGAACAAGC | CCTACAAGAA | ATCTGCCCGT | GTGGTCGGCG | ACGTGATCGG | TAAGTACCAC | 120 |
| CCGCACGGCG | ACACCGCGGT | CTACGACACC | ATCGTGCGCT | GGCGCAGCC | GTTCTCGCTG | 180 |
| CGCTACATGC | TGGTAGACGG | CCAGGGCAAC | TTCGGTTCGG | TGGACGGCGA | CAACGCCGCA | 240 |
| GCCATGCGAT | ACACCGAAGT | GCGCATGGCC | AAGCTGGCCC | ACGAACTGCT | GGCGGACCTG | 300 |
| GAAAAGGAAA | CCGTCGACTG | GGTGCCCAAC | TACGATGGCA | CCGAGCAGAT | CCCGGCGGTC | 360 |

```
ATGCCGACCA  AGATTCCCAA  CCTGCTGGTC  AACGGTTCCA  GCGGCATCGC  AGTAGGTATG        420

GCA                                                                          423
```

( 2 ) INFORMATION FOR SEQ ID NO:84:

( i ) SEQUENCE CHARACTERISTICS:
        ( A ) LENGTH: 177 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="gyrB gene segment"

( i i i ) HYPOTHETICAL: NO ( i v ) ANTI-SENSE: NO ( v i ) ORIGINAL SOURCE:
        ( A ) ORGANISM: Pseudomonas aeruginosa ( x i ) SEQUENCE DESCRIPTION: SEQ ID NO:84:

```
AAAAGGCCTG  GGATGTATAT  AGGCGACACC  GACGATGGCA  CCGGTCTGCA  CCACATGGTG         60

TTCGAGGTGG  TGGATAACTC  CATCGACGAA  GCGCTGGCCG  GTTACTGCAG  CGAAATCAGC        120

ATCACCATCC  ATACGGATGA  GTCGATCACT  GTCCGCGATG  ACGGCCGCGG  TATTCCG          177
```

( 2 ) INFORMATION FOR SEQ ID NO:85:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="gyrA gene segment"

( i i i ) HYPOTHETICAL: NO ( i v ) ANTI-SENSE: NO ( v i ) ORIGINAL SOURCE:
        ( A ) ORGANISM: Rickettsia rickettsii ( x i ) SEQUENCE DESCRIPTION: SEQ ID NO:85:

```
GACGGGCTGA  AGCCGGTACA  TCGTAGGTTA  TTATACGCAA  TGCTACAGTT  AAGGCTTGAG         60

CCGAATTCCG  GCTATAAGAA  ATGTGCGAGG  GTAGTCGGTG  ACGTAATAGG  TAAATACCAC        120

CCGCACGGTG  ATGTGGCAGT  GTATGATACC  TTGGTACGCC  TTGCTCAGCA  TTTTTCGTTG        180

CGTTATCCTT  TAATTGATGG  GCAGGGTAAT  TTCGGCTCTA  TCGACGGTGA  TAATTCAGCA        240

GCTATGCGTT  ATACCGAATC  ACGTATGACG  GACATATGTA  CGTTATTAAT  GGAGGACATC        300

GATAAAGATA  CGGTAGATTT  TCGCCCTACT  TATGATGGTT  CCGATTTAGA  ACCGGTAATA        360

ATGCCGGCAA  GTTTTCCGAA  TTTACTAGCT  AATGGTTCTG  AAGGCATTGC  TGTCGGTATG        420

GCA                                                                          423
```

( 2 ) INFORMATION FOR SEQ ID NO:86:

( i ) SEQUENCE CHARACTERISTICS:
        ( A ) LENGTH: 177 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="gyrB gene segment"

( i i i ) HYPOTHETICAL: NO ( i v ) ANTI-SENSE: NO ( v i ) ORIGINAL SOURCE:
    ( A ) ORGANISM: Rickettsiae rickettsii ( x i ) SEQUENCE DESCRIPTION: SEQ ID NO:86:

| AAGAGACCAG | GGATGTATAT | CGGGGATGTT | GGAGACGGGT | CGGGTCTACA | TCATATGATT | 60 |
| TATGAAGTAG | TCGACAACGC | TATCGATGAG | TCGCTTGCTG | GTTATTGCGA | TCTAGTACGA | 120 |
| GTAACATTAA | ATAAAAACGG | TTCAGTAACC | GTATCCGATA | ACGGCCGCAG | CATTCCG | 177 |

( 2 ) INFORMATION FOR SEQ ID NO:87:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="parC gene segment"

( i i i ) HYPOTHETICAL: NO ( i v ) ANTI-SENSE: NO ( v i ) ORIGINAL SOURCE:
        ( A ) ORGANISM: Rickettsia rickettsii ( x i ) SEQUENCE DESCRIPTION: SEQ ID NO:87:

| GACGGGTTGA | AGCCCGTGCA | TCGCCGAATT | ATCT ( 2 ) INFORMATION FOR SEQ ID NO:89:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="gyrA gene segment"

( i i i ) HYPOTHETICAL: NO ( i v ) ANTI-SENSE: NO ( v i ) ORIGINAL SOURCE:
        ( A ) ORGANISM: Salmonella typhimurium ( x i ) SEQUENCE DESCRIPTION: SEQ ID NO:89:

```
GACGGGTTTA  AGCCGGTCCA  CCGTCGCGTA  CTTTACGCCA  TGAACGTATT  GGGCAATGAC     60
TGGAACAAAG  CCTATAAAAA  ATCTGCCCGT  GTCGTTGGTG  ACGTAATCGG  TAAATACCAT    120
CCCCACGGCG  ATTCCGCAGT  GTATGACACC  ATCGTTCGTA  TGGCGCAGCC  ATTCTCGCTG    180
CGTTACATGC  TGGTGGATGG  TCAGGGTAAC  TTCGGTTCTA  TTGACGGCGA  CTCCGCGGCG    240
GCAATGCGTT  ATACGGAGAT  CCGTCTGGCG  AAAATCGCCC  ACGAACTGAT  GGCCGATCTC    300
GAAAAGAGA   CGGTGGATTT  CGTGGATAAC  TATGACGGTA  CGGAAAAAAT  TCCGGACGTC    360
ATGCCGACCA  AAATTCCGAA  TCTGCTGGTG  AACGGTTCTT  CCGGAATAGC  CGTTGGTATG    420
GCA                                                                      423
```

( 2 ) INFORMATION FOR SEQ ID NO:90:

( i ) SEQUENCE CHARACTERISTICS:
        ( A ) LENGTH: 177 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="gyrB gene segment"

( i i i ) HYPOTHETICAL: NO ( i v ) ANTI-SENSE: NO ( v i ) ORIGINAL SOURCE:
        ( A ) ORGANISM: Salmonella typhimurium ( x i ) SEQUENCE DESCRIPTION: SEQ ID NO:90:

```
AAGAGACCGG  GGATGTATAT  CGGCGACACG  GATGACGGCA  CCGGTCTGCA  CCACATGGTA     60
TTCGAGGTGG  TAGATAACGC  TATCGACGAA  GCGCTCGCAG  GTCACTGTAA  AGATATCGTC    120
GTGACTATTC  ACGCCGATAA  CTCCGTGTCC  GTAACGGATG  ATGGCCGCGG  TATTCCC       177
```

( 2 ) INFORMATION FOR SEQ ID NO:91:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="gyrA gene segment"

( i i i ) HYPOTHETICAL: NO ( i v ) ANTI-SENSE: NO (vi) ORIGINAL SOURCE:
    (A) ORGANISM: Serpulina hyodysenteriae (xi) SEQUENCE DESCRIPTION: SEQ ID NO:91:

| | | | | | |
|---|---|---|---|---|---|
| GATGGGCTGA | AGCCGGTTCA | TAGAAGAATC | CTATATGCTA | TGTATGATGC | TAATCTTACT | 60 |
| CATGATAAAC | CATATAAGAA | GTCTGCAGCC | ACTGTAGGTG | AAGTTTTAGC | ACGTTATCAC | 120 |
| CCGCATGGAG | ATGCTGCTGT | TTATGGTACT | ATGGTAAGAA | TGGCTCAGGA | TTTCTCTATG | 180 |
| CGTTACTTGC | TTGTAGACGG | ACAGGGAAAC | TTCGGTTCTA | TAGATGATGA | CCCGCCTGCA | 240 |
| GCAATGCGTT | ATACTGAAGC | TAGAATGACG | CGTTTGCTG  | AAGAAATGCT | TAATGATATA | 300 |
| GAAAAAGAAA | CTGTAAAATT | TGTACCAAAC | TTCGATGATT | CCAGAACTGA | ACCTTCTGTA | 360 |
| TTACCAGCAA | CAGTACCTCA | GCTTTTAGTT | AATGGAAGTA | TGGGCATCGC | AGTTGGTATG | 420 |
| GCA | | | | | | 423 |

(2) INFORMATION FOR SEQ ID NO:92:

(i) SEQUENCE CHARACTERISTICS:
        (A) LENGTH: 423 base pairs
        (B) TYPE: nucleic acid
        (C) STRANDEDNESS: double
        (D) TOPOLOGY: Not Relevant (ii) MOLECULE TYPE: other nucleic acid
        (A) DESCRIPTION: /desc ="gyrA gene segment"

(iii) HYPOTHETICAL: NO (iv) ANTI-SENSE: NO (vi) ORIGINAL SOURCE:
        (A) ORGANISM: Serpulina innocens (xi) SEQUENCE DESCRIPTION: SEQ ID NO:92:

| | | | | | |
|---|---|---|---|---|---|
| GATGGGTTCA | AGCCTGTACA | TCGTCGTATC | CTCTATGGGA | TGAATGAACT | CGGTGTGACA | 60 |
| CCTGATAAAC | CGCATAAAAA | ATCTGCTCGT | ATTACGGGTG | ATGTCATGGG | TAAATATCAC | 120 |
| CCGCATGGGG | ATTCTTCTAT | TTATGAAGCT | ATGGTTCGTA | TGGCTCAGTG | GTGGAGTTAT | 180 |
| CGCCATATGC | TTGTTGATGG | GCATGGCAAT | TTTGGTTCTA | TGGATGGTGA | TGGTGCTGCC | 240 |
| GCACAACGTT | ATACTGAAGC | GCGCATGAGT | AAAATTGCGC | TTGAATTATT | AAGGGATATC | 300 |
| AATAAAAATA | CCGTTAATTT | TCAAGATAAC | TACGATGGAA | GCGAAAGAGA | ACCAGTAGTA | 360 |
| TTACCAGCTC | GCTTTCCTAA | TTTATTAGTC | AATGGAGCGA | CAGGTATCGC | AGTCGGTATG | 420 |
| GCA | | | | | | 423 |

(2) INFORMATION FOR SEQ ID NO:93:

(i) SEQUENCE CHARACTERISTICS:
        (A) LENGTH: 423 base pairs
        (B) TYPE: nucleic acid
        (C) STRANDEDNESS: double
        (D) TOPOLOGY: Not Relevant (ii) MOLECULE TYPE: other nucleic acid
        (A) DESCRIPTION: /desc ="gyrA gene segment"

(iii) HYPOTHETICAL: NO (iv) ANTI-SENSE: NO (vi) ORIGINAL SOURCE:
        (A) ORGANISM: Shigella dysenteriae (xi) SEQUENCE DESCRIPTION: SEQ ID NO:93:

| | | | | | |
|---|---|---|---|---|---|
| GACGGGCTAA | AGCCAGTTCA | CCGTCGCGTA | CTTTACGCCA | TGAACGTACT | AGGCAATGAC | 60 |

```
TGGAACAAAG  CCTATAAAAA  ATCTGCCCGT  GTCGTTGGTG  ACGTAATCGG  TAAATACCAT   120

CCCCATGGTG  ACTCGGCGGT  TTATGACACG  ATCGTCCGTT  TGGCGCAGCC  ATTCTCGCTG   180

CGTTACATGC  TGGTAGACGG  TCAGGGTAAC  TTCGGTTCCA  TCGACGGCGA  CTCTGCGGCG   240

GCAATGCGTT  ATACGGAAAT  CCGTCTGGCG  AAAATTGCCC  ATGAACTGAT  GGCCGATCTC   300

GAAAAGAGA   CGGTCGATTT  CGTTGATAAC  TATGACGGCA  CGGAAAAAAT  TCCCGACGTC   360

ATGCCAACCA  AAATTCCTAA  CCTGCTGGTG  AACGGTTCTT  CCGGCATTGC  TGTAGGTATG   420

GCA                                                                     423
```

(2) INFORMATION FOR SEQ ID NO:94:

(i) SEQUENCE CHARACTERISTICS:
        (A) LENGTH: 180 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
        (A) ORGANISM: Shigella dysenteriae (xi) SEQUENCE DESCRIPTION: SEQ ID NO:94:

```
AAGCGGCCTG  GGATGTACAT  TGGCGACACG  GATGACGGCA  CCGGTCTGCA  CCACATGGTA    60

TTCGAGGTGG  TAGATAACGC  TATCGACGAA  GCGCTCGCGG  GTCACTGTAA  AGAAATTATC   120

GTCACCATTC  ACGCCGATAA  CTCTGTCTCC  GTACAGGATG  ATGGCCGCGG  TATTCCGGGG   180
```

(2) INFORMATION FOR SEQ ID NO:95:

(i) SEQUENCE CHARACTERISTICS:
        (A) LENGTH: 423 base pairs
        (B) TYPE: nucleic acid
        (C) STRANDEDNESS: double
        (D) TOPOLOGY: Not Relevant (ii) MOLECULE TYPE: other nucleic acid
        (A) DESCRIPTION: /desc ="gyrA gene segment"

(iii) HYPOTHETICAL: NO (iv) ANTI-SENSE: NO (vi) ORIGINAL SOURCE:
        (A) ORGANISM: Streptococcus faecalis (xi) SEQUENCE DESCRIPTION: SEQ ID NO:95:

```
GATGGGCTGA  AACCTGTTCA  TCGCCGTATT  TTATACGGGA  TGAACGAATT  GGGTGTGACC    60

CCAGATAAAG  CCCATAAAAA  ATCTGCCAGA  ATCGTTGGGG  ATGTTATGGG  TAAGTATCAC   120

CCCCATGGAG  ACAGTTCTAT  TTATGAATCC  ATGGTGCGGA  TGGCACAACC  ATTTAGTTAT   180

CGGTACATGC  TAGTGGATGG  ACATGGTAAC  TTTGGTTCTG  TCGATGGTGA  TGGAGCAGCT   240

GCGATGCGGT  ATACCGAAGC  ACGTATGAGT  AAAATTGCCA  CGGAGATGCT  ACGGGATATC   300

AATAAAAATA  CTGTAGATTT  CCAAAGTAAC  TATGACGATA  CAGAAAGGGA  ACCAGTCGTA   360

CTTCCAGCAC  GCTTTCCTAA  TCTGTTAGTT  AACGGAACAA  CAGGAATAGC  AGTCGGTATG   420

GCA                                                                     423
```

(2) INFORMATION FOR SEQ ID NO:96:

(i) SEQUENCE CHARACTERISTICS:
  (A) LENGTH: 423 base pairs
  (B) TYPE: nucleic acid
  (C) STRANDEDNESS: double
  (D) TOPOLOGY: Not Relevant (ii) MOLECULE TYPE: other nucleic acid
  (A) DESCRIPTION: /desc ="gyrA gene segment"

(iii) HYPOTHETICAL: NO (iv) ANTI-SENSE: NO (v) ORIGINAL SOURCE:
  (A) ORGANISM: Streptococcus faecium (xi) SEQUENCE DESCRIPTION: SEQ ID NO:96:

| | | | | | | |
|---|---|---|---|---|---|---|
| GACGGGTTAA | AGCCGGTTCA | CCGCCGTATC | TTATACGGAA | TGAATGAATT | AGGTGTAACG | 60 |
| CCAGATGAAG | CACATAAAAA | ATCAGCCAGA | ATCGTTGGGG | ATGTCATGGG | TAAATACCAT | 120 |
| CCCCACGGTG | ATAGTGCGAT | CTATGAATCC | ATGGTACGTA | TGGCACAGCC | ATTTAGTTAC | 180 |
| CGCTACATGT | TGGTAGACGG | TCACGGAAAC | TTTGGTTCAG | TCGATGGAGA | TGGGGCTGCT | 240 |
| GCGATGCGTT | ATACCGAAGC | GCGTATGAGC | AAAATCGCCA | CAGAAATGCT | CCGTGATATC | 300 |
| AATAAAAATA | CAGTCGATTT | CCAAAGCAAC | TATGATGATA | CAGAAAAAGA | ACCTGTTGTG | 360 |
| TTACCAGCCC | GTTTCCCTAA | CCTTTTAGTG | AACGGCACAA | CTGGCATTGC | TGTCGGTATG | 420 |
| GCA | | | | | | 423 |

(2) INFORMATION FOR SEQ ID NO:97:

(i) SEQUENCE CHARACTERISTICS:
  (A) LENGTH: 423 base pairs
  (B) TYPE: nucleic acid
  (C) STRANDEDNESS: double
  (D) TOPOLOGY: Not Relevant (ii) MOLECULE TYPE: other nucleic acid
  (A) DESCRIPTION: /desc ="gyrA gene segment"

(iii) HYPOTHETICAL: NO (iv) ANTI-SENSE: NO (v) ORIGINAL SOURCE:
  (A) ORGANISM: Streptococcus pneumoniae (xi) SEQUENCE DESCRIPTION: SEQ ID NO:97:

| | | | | | | |
|---|---|---|---|---|---|---|
| GATGGGTTGA | AGCCGGTTCA | CCGTCGCATC | CTCTACGGAA | TGAATGAATT | GGGTGTGACC | 60 |
| CCAGACAAAC | CCCATAAAAA | ATCTGCTCGT | ATTACAGGGG | ATGTCATGGG | TAAATACCAC | 120 |
| CCACACGGGG | ATTCCTCTAT | TTATGAAGCC | ATGGTCCGTA | TGGCTCAATG | GTGGAGCTAC | 180 |
| CGTTACATGC | TTGTAGATGG | TCATGGGAAT | TTTGGTTCCA | TGGATGGAGA | TAGTTCTGCC | 240 |
| GCTCAACGTT | ATACCGAGGC | ACGTATGAGC | AAGATTGCTC | TGGAAATGCT | TCGTGATATC | 300 |
| AACAAAAATA | CAGTTGATTT | CGTTGATAAC | TATGATGCCA | ATGAACGGGA | ACCCTTGGTC | 360 |
| TTGCCAGCGC | GTTTTCCAAA | CCTTTTGGTT | AATGGAGCAA | CTGGCATTGC | GGTTGGTATG | 420 |
| GCA | | | | | | 423 |

(2) INFORMATION FOR SEQ ID NO:98:

(i) SEQUENCE CHARACTERISTICS:
  (A) LENGTH: 423 base pairs
  (B) TYPE: nucleic acid
  (C) STRANDEDNESS: double
  (D) TOPOLOGY: Not Relevant (i i) MOLECULE TYPE: other nucleic acid
  (A) DESCRIPTION: /desc ="gyrA gene segment"

(i i i) HYPOTHETICAL: NO (i v) ANTI-SENSE: NO (v i) ORIGINAL SOURCE:
  (A) ORGANISM: Streptococcus pyogenes (x i) SEQUENCE DESCRIPTION: SEQ ID NO:98:

| | | | | | | |
|---|---|---|---|---|---|---|
| GATGGGCTGA | AGCCGGTTCA | TAGAAGAATA | CTATATGCTA | TGTATGATGC | TAATCTTACT | 60 |
| CATGACAAAC | CATATAAGAA | GTCAGCAGCG | ACAGTAGGTG | AAGTTTTGGC | ACGTTATCAC | 120 |
| CCGCATGGAG | ATGCTGCAGT | TTACGGCACT | ATGGTAAGAA | TGGCACAGGA | TTTTTCTATG | 180 |
| CGTTATTTAC | TTGTAGACGG | ACAGGGTAAC | TTCGGTTCTA | TAGATGATGA | CCCGCCTGCT | 240 |
| GCTATGCGTT | ATACTGAAGC | TAGAATGACT | CGTTTTGCAG | AAGAAATGCT | CAATGATATA | 300 |
| GAAAAGAAA | CTGTTAAATT | TGTTCCGAAC | TTTGATGATT | CCAGAACTGA | GCCTTCTGTA | 360 |
| CTTCCAGCTA | CAGTTCCTCA | GCTTCTTGTA | AATGGAAGTA | TGGGGATCGC | AGTAGGTATG | 420 |
| GCA | | | | | | 423 |

(2) INFORMATION FOR SEQ ID NO:99:

(i) SEQUENCE CHARACTERISTICS:
    (A) LENGTH: 423 base pairs
    (B) TYPE: nucleic acid
    (C) STRANDEDNESS: double
    (D) TOPOLOGY: Not Relevant (i i) MOLECULE TYPE: other nucleic acid
    (A) DESCRIPTION: /desc ="gyrA gene segment"

(i i i) HYPOTHETICAL: NO (i v) ANTI-SENSE: NO (v i) ORIGINAL SOURCE:
    (A) ORGANISM: Treponema denicola (x i) SEQUENCE DESCRIPTION: SEQ ID NO:99:

| | | | | | | |
|---|---|---|---|---|---|---|
| GATGGGCTAA | AACCGGTGCA | CAGGCGTATC | CTTTATTCAA | TGGAGGAAAA | GGGCTTACGC | 60 |
| AGTTCAGGCC | CCACCCGAAA | ATGTGCTAAG | ATCGTAGGTG | ATGTATTAGG | AAGTTACCAC | 120 |
| CCTCACGGCG | ACGCTTCGGT | CTATGATGCC | CTCGTCCGCC | TTGGACAGGA | CTTCTCTCTC | 180 |
| CGCTATCCGG | TTATTTATCC | CCAAGGAAAC | TTCGGAACCA | TAGGAGGCGA | CCCGCCCGCA | 240 |
| GCTTACCGAT | ACACGGAAGC | TAAGATGGCC | AAAATAGCCG | AAACCATGGT | CGAGGATATA | 300 |
| AAAAAAGAAA | CAGTCGATTT | TATTCCGAAC | TTTGACGATT | CTACAAAAGA | ACCGACCGTT | 360 |
| CTTCCGGCTA | AATTTCCCTT | CTTGCTTGCA | AACGGTTCAA | GCGGCATAGC | CGTAGGTATG | 420 |
| GCA | | | | | | 423 |

(2) INFORMATION FOR SEQ ID NO:100:

(i) SEQUENCE CHARACTERISTICS:
    (A) LENGTH: 424 base pairs
    (B) TYPE: nucleic acid
    (C) STRANDEDNESS: double
    (D) TOPOLOGY: Not Relevant (i i) MOLECULE TYPE: other nucleic acid
    (A) DESCRIPTION: /desc ="gyrA gene segment"

(i i i) HYPOTHETICAL: NO ( i v ) ANTI-SENSE: NO ( v i ) ORIGINAL SOURCE:
    ( A ) ORGANISM: Treponema pallidum ( x i ) SEQUENCE DESCRIPTION: SEQ ID NO:100:

| | | | | | | |
|---|---|---|---|---|---|---|
| GACGGGTTGA | AGCCGGTTCA | CAGACGTATC | CTCTACGCGA | TGGAGGAAAA | AGGGCTACGC | 60 |
| TTTTCAGGAC | CTACACGAA | GTGTGCCAAG | ATAGTGGGGG | ACGTTTGGG | AAGCTTTCAT | 120 |
| CCTCATGGGG | ATGCGTCCGT | CTATGACGCG | CTAGTGCGTC | TTGGGCAAGA | TTTTTCCCTT | 180 |
| CGTTATCCAG | TCATTCATCC | TCAAGGAAAT | TTCGGGACTA | TCGGGGGCGA | CCCTCCGGCA | 240 |
| GCGTATCGGT | ACACCGAAGC | GAAGATGGCG | CGTATTGCAG | AATCTATGGT | AGAGGACATA | 300 |
| AAAAGGAAA | CGGTTTCCTT | TGTTCCCAAT | TTTGACGATT | CTGACGTAGA | GCCCACGGTT | 360 |
| CTTCCTGGAA | GGTTTCCTTT | TCTTCTTGCG | AATGGGTCCA | GTGGCATCGC | TGTGGGTATG | 420 |
| GCAT | | | | | | 424 |

( 2 ) INFORMATION FOR SEQ ID NO:101:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: Not Relevant ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:101:

Lys  Arg  Pro  Gly  Met  Tyr  Ile  Gly
    1                      5

( 2 ) INFORMATION FOR SEQ ID NO:102:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: Not Relevant ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:102:

Asn  Asn  Gly  Arg  Gly  Ile  Pro
    1                      5

( 2 ) INFORMATION FOR SEQ ID NO:103:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: Not Relevant ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:103:

Asn Gly Leu Lys Pro Val His Arg Arg
    1               5

( 2 ) INFORMATION FOR SEQ ID NO:104:

( i ) SEQUENCE CHARACTERISTICS:
                    ( A ) LENGTH: 7 amino acids
                    ( B ) TYPE: amino acid
                    ( C ) STRANDEDNESS:
                    ( D ) TOPOLOGY: Not Relevant ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:104:

Gly Ile Ala Val Gly Met Ala
    1               5

( 2 ) INFORMATION FOR SEQ ID NO:105:

( i ) SEQUENCE CHARACTERISTICS:
                    ( A ) LENGTH: 36 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i v ) ANTI-SENSE: NO ( v i ) ORIGINAL SOURCE:
                    ( A ) ORGANISM: Common to many species ( x i ) SEQUENCE DESCRIPTION: SEQ ID NO:105:

AACTGCAGGT ACCAAGAGGC CGGGGATGTA TATAGG                                       36

( 2 ) INFORMATION FOR SEQ ID NO:106:

( i ) SEQUENCE CHARACTERISTICS:
                    ( A ) LENGTH: 19 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i v ) ANTI-SENSE: YES ( v i ) ORIGINAL SOURCE:
                    ( A ) ORGANISM: Common to many species ( x i ) SEQUENCE DESCRIPTION: SEQ ID NO:106:

GGAATGCCGC GGCCGTTAT                                                          19

( 2 ) INFORMATION FOR SEQ ID NO:107:

( i ) SEQUENCE CHARACTERISTICS:
                    ( A ) LENGTH: 423 base pairs
                    ( B ) TYPE: nucleic acid
                    ( C ) STRANDEDNESS: double
                    ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Actinomyces israelii ( x i ) SEQUENCE DESCRIPTION: SEQ ID NO:107:

| GATGGGCTTA | AGCCGGTTCA | CCGCCGCGTC | CTGTACGCCA | TGTACGACGG | CGGCTACCGC | 60 |
|---|---|---|---|---|---|---|
| CCCAGCGCCT | CCTTCTCCAA | GTCCTCGCGC | GTCGTGGGCG | AGGTCATGGG | GAACTACCAC | 120 |
| CCGCACGGCG | ACGCCGCCAT | CTACGACGCC | CTGGCGCGCC | TGGTGCAGTG | GTGGTCGCTG | 180 |
| CGCTACCCGC | TGGTGGCCGG | GCAGGGCAAC | TTCGGCACGC | CGGGAAACCT | GGGGCCCGCC | 240 |
| GCCCCCCGGT | ACACCGAGTG | CAAGATGGCG | CCGCTGGCCA | TGGAGATGGT | CCGCGACATC | 300 |
| GACGAGGAGA | GCGTCGACTT | CCAGGACAAC | TACGACGGGC | GCAACCAGGA | GCCGGTCATC | 360 |
| CTGCCCGCGC | GCTTCCCCAA | CCTCCTGGTC | AACGGCTCCG | AGGGCATCGC | AGTAGGTATG | 420 |
| GCA | | | | | | 423 |

( 2 ) INFORMATION FOR SEQ ID NO:108:

( i ) SEQUENCE CHARACTERISTICS:
        ( A ) LENGTH: 420 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Actinomyces israelii ( x i ) SEQUENCE DESCRIPTION: SEQ ID NO:108:

| GATGGGCTAA | AGCCGGTGCA | GCGCCGCATC | CTGTTCCAGA | TGGACCGCAT | GGGGCTGCGC | 60 |
|---|---|---|---|---|---|---|
| CCCGACCGGC | CGCACGTGAA | GTCGTCGCGC | GTCGTCGGCG | ACGTCATGGG | GCGGCTCCAC | 120 |
| CCGCACGGCG | ACGTCGCCAT | CTACGAGGCC | CTGGTGCGCC | TGGCCCAGCC | CTTCACCATG | 180 |
| CGCCTGCCGC | TGGTCGACGG | GCACGGCAAC | TTCGGCTCCC | TGGACGACGG | CCCGGCCGCG | 240 |
| GCCCGCTACA | CCGAGGCGAG | GCTGGCCAGC | AGCGCCCTGG | CGCTGACGGC | GGACATCGAC | 300 |
| GAGGACACCG | TCGACTTCTC | CCCCAACTAC | GACTACACCC | TCACCGAGCC | GGGTGTCCTG | 360 |
| CCGGCGGCCT | TCCCCAACCT | GCTGGTCAAC | GGCGCCTCGG | GAATCGCCGT | TGGTATGGCA | 420 |

( 2 ) INFORMATION FOR SEQ ID NO:109:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Actinomyces naesundii ( x i ) SEQUENCE DESCRIPTION: SEQ ID NO:109:

-continued

```
GATGGGCTTA AGCCGGTCCA CCGCCGCGTC CTGTACGCCA TGTACGACGG CGGCTACCGC      60

CCCACCGCCT CCTTCTCCAA GTCCTCCCGC GTCGTCGGTG AGGTGATGGG TAACTACCAC     120

CCCCACGGAG ACAGCGCCAT CTACGACGCC CTGGCCCGCC TGGTCCAGTG GTGGTCGATG     180

CGCTACCCGC TGGTGGCCGG TCAGGGGAAC TTCGGCACGC CCGGCAACCT GGGGCCCGCC     240

GCCCCCCGGT ACACCGAGTG CAAGATGGCG CCCCTGGCCA TGGAGATGCT CCGGGACATC     300

GACGAGGACA GCGTCGACTT CCAGGACAAC TACGACGGCA AGAACCAGGA GCCGGTCATT     360

CTGCCGGCCC GCTTCCCCAA CCTCCTGGTC AACGGCTCCG AGGGTATCGC CGTGGGTATG     420

GCA                                                                   423
```

( 2 ) INFORMATION FOR SEQ ID NO:110:

( i ) SEQUENCE CHARACTERISTICS:
      ( A ) LENGTH: 420 base pairs
      ( B ) TYPE: nucleic acid
      ( C ) STRANDEDNESS: double
      ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
      ( A ) ORGANISM: Actinomyces naesundii ( x i ) SEQUENCE DESCRIPTION: SEQ ID NO:110:

```
GACGGGTTTA AGCCGGTGCA GCGCCGCATC CTGTTCCAGA TGGACCGCAT GGGGCTGCGC      60

CCCGACCGCC CGCACGTGAA GTCCTCCCGG GTCGTGGGCG ACGTCATGGG CCGACTCCAC     120

CCACACGGCG ACACCGCGAT CTACGAGGCG CTGGTGCGTC TGGCCCAGCC CTTCACGATG     180

CGTCTGCCGC TCATTGACGG GCACGGTAAC TTCGGCTCCC TGGATGACGG ACCGGCGGCC     240

CCCCGCTACA CCGAGGCACG CCTGGCCGAG CCGGCGCTGG CGCTGACGGC GGATCTGGAC     300

GAGGACACGG TCGACTTCGC CCCCAACTAC GACTACACGC TCACCGAGCC CGAGGTCCTG     360

CCCGCGGCCT TCCCGAACCT GCTGGTCAAC GGCGCGGCCG GCATAGCGGT CGGTATGGCA     420
```

( 2 ) INFORMATION FOR SEQ ID NO:111:

( i ) SEQUENCE CHARACTERISTICS:
      ( A ) LENGTH: 423 base pairs
      ( B ) TYPE: nucleic acid
      ( C ) STRANDEDNESS: double
      ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
      ( A ) ORGANISM: Arthrobacter globiformis ( x i ) SEQUENCE DESCRIPTION: SEQ ID NO:111:

```
GATGGGTTGA AACCTGTCCA CCGCCGCGTG CTGTATGCGA TGTTCGACGG CGGCTACCGC      60

CCGGACCGCG CCTTCAACAA GTGTGCTCGT GTGGTCGGCG AGGTCATGGG CCAGTACCAC     120

CCGCACGGTG ACACGGCCAT CTACGATGCG CTGGTACGCC TGATCCAGGA CTGGACCATG     180

CGGTACCCGC TGGCGCTCGG CCAGGGCAAC TTCGGCTCAC CCGGCAACGA CGGCGCTGCG     240

GCTCCGCGGT ACACGGAAAC CAAGATGGCA CCGCTGGCCA TGGAAATGGT CCGGGACATC     300
```

| | | | | | |
|---|---|---|---|---|---|
| GACGAGGAGA | CCGTCGACTT | CCAGGACAAC | TATGACGGCA | AGAACCAGGA | ACCCACGATC | 360
| CTCCCGGCGC | GGTTCCCCAA | CCTGCTGGTC | AACGGGTCCT | CAGGCATCGC | GGTGGGTATG | 420
| GCA | | | | | | 423

( 2 ) INFORMATION FOR SEQ ID NO:112:

( i ) SEQUENCE CHARACTERISTICS:
        ( A ) LENGTH: 420 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Arthrobacter globiformis ( x i ) SEQUENCE DESCRIPTION: SEQ ID NO:112:

| | | | | | |
|---|---|---|---|---|---|
| GATGGGCTAA | AGCCGGTACA | GCGCCGCATC | CTCTACATGA | TGAGCGACAT | GGGCCTCCGT | 60
| CCCGACCGCG | GCCACGTCAA | GAGCGCCCGC | GTGGTGGGTG | AGGTCATGGG | CAAGCTCCAC | 120
| CCGCACGGCG | ACACCGCCAT | CTACGACGCC | ATGGTGCGCA | TGGCCCAGGA | CTTCTCGCTC | 180
| CGGCTCCCCC | TGATCGACGG | CCATGGGAAC | TTCGGCTCGC | TCGACGACGG | CCCCGCGGCA | 240
| CCGCGGTACA | CCGAGGCCCG | GCTGGCGGCG | GCAGCGCTCA | CCATGACGGA | CCACCTCGAC | 300
| GAAGACGTGG | TGGACTTCGT | CCCCAATTAC | GACAACCAGC | TCACCCAGCC | GGAGGTCCTG | 360
| CCCGCAGCGT | TCCCCAACCT | GCTGGTCAAC | GGCACCACCG | GCATAGCTGT | GGGTATGGCA | 420

( 2 ) INFORMATION FOR SEQ ID NO:113:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Arthrobacter luteus ( x i ) SEQUENCE DESCRIPTION: SEQ ID NO:113:

| | | | | | |
|---|---|---|---|---|---|
| GATGGGCTAA | AGCCCGTGCA | CCGGCGCGTG | CTGTACGCGA | TGTACGACGG | CGGCTACCGC | 60
| CCCGACCGCT | CGTACTCGAA | GTGCTCGCGC | GTCGTCGGCG | ACGTCATGGG | CAAGTTCCAC | 120
| CCGCACGGCG | ACAGCGCGAT | CTACGACGCG | CTCGTGCGCC | TCGTGCAGGA | CTGGTCCCTG | 180
| CGCTACCCGC | TCGTCGCCGG | CCAGGGGAAC | TTCGGCTCCC | CCGGCAACGA | CCCGGCGGCC | 240
| GCCCCGCGAT | ACACCGAGTG | CCGCATGGCG | CCGATCGCCA | TGGAGATGGT | CCGGGACATC | 300
| GATAAGGACA | CCGTCGACTT | CCAGGACAAC | TACGACGGCC | GCACGCAGGA | GCCGTCGGTC | 360
| CTGCCGGCCC | GGTTCCCGAA | CCTGCTGGTC | AACGGCTCGG | CGGGCATAGC | CGTTGGTATG | 420
| GCA | | | | | | 423

( 2 ) INFORMATION FOR SEQ ID NO:114:

( i ) SEQUENCE CHARACTERISTICS:
    ( A ) LENGTH: 426 base pairs
    ( B ) TYPE: nucleic acid
    ( C ) STRANDEDNESS: double
    ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Arthrobacter luteus ( x i ) SEQUENCE DESCRIPTION: SEQ ID NO:114:

| | | | | | |
|---|---|---|---|---|---|
| GACGGGCTGA | AGCCGGTTCA | GCGGCGCATC | ATCTACGCCA | TGAGTGAGTT | GGGCCTGGAC | 60 |
| GCCGATTCCA | AGCACAAGAA | GTCGGCGCGT | ACCGTCGGTG | ACGTGCTCGG | TAAGTTCCAC | 120 |
| CCCCACGGCG | ACTCTGCCTG | CTACGAAGCC | ATGGTGCTGA | TGGCGCAGCC | GTTCAGCTAC | 180 |
| CGCTACACGC | TGGTGGACGG | CCAGGGTAAC | TGGGGTGCGC | CGGATGATCC | CAAGTCCTTC | 240 |
| GCCGCCATGC | GATACACCGA | GGCGCGCCTG | TCGCGTTACT | CGGAAGTCTT | GTTGAGCGAA | 300 |
| TTGGGGCAGG | GCACTGCGGA | CTGGGCCCG  | AACTTCGACG | GCACCCTCGA | TGAACCGCTG | 360 |
| GTATTGCCAG | CACGTTTGCC | GAATATCCTG | CTCAATGGCA | CCACCGGTAT | CGCAGTCGGT | 420 |
| ATGGCA | | | | | | 426 |

( 2 ) INFORMATION FOR SEQ ID NO:115:

( i ) SEQUENCE CHARACTERISTICS:
    ( A ) LENGTH: 426 base pairs
    ( B ) TYPE: nucleic acid
    ( C ) STRANDEDNESS: double
    ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Anacystis nidulans ( x i ) SEQUENCE DESCRIPTION: SEQ ID NO:115:

| | | | | | |
|---|---|---|---|---|---|
| GACGGGTTCA | AGCCAGTGCA | CCGGCGCATT | CTTTACGCGA | TGTATGAGCT | GGGCCTGACG | 60 |
| CCCGATCGCC | CCTTCCGAAA | ATGTGCACGG | GTGGTCGGGG | AAGTGCGCGG | TAAGTATCAC | 120 |
| CCCCACGGCG | ACACGGCGGT | CTATGACGCC | TTGGTTCGCA | TGGCCCAAGA | CTTCTCGATG | 180 |
| CGATCGCCCT | TGATCGATGG | CCACGGCAAC | TTCGGATCGA | TCGACAACGA | TCCGCCGGCG | 240 |
| GCGATGCGGT | ACACCGAGTC | GCGCCTGAAG | CCGCTGACAA | CTGATGGTTT | GCTTCAGGAT | 300 |
| ATCGAAGCCG | AAACTGTCGA | TTTCAGCGAT | AACTTTGACG | GCTCGCAACA | GGAACCAACA | 360 |
| GTTCTGCCGG | CGCGGCTGCC | GCAACTGCTG | CTGAACGGTT | CCTCCGGCAT | AGCTGTCGGT | 420 |
| ATGGCA | | | | | | 426 |

( 2 ) INFORMATION FOR SEQ ID NO:116:

( i ) SEQUENCE CHARACTERISTICS:
    ( A ) LENGTH: 426 base pairs
    ( B ) TYPE: nucleic acid
    ( C ) STRANDEDNESS: double
    ( D ) TOPOLOGY: Not Relevant ( i i ) MOLECULE TYPE: DNA (genomic)

5,645,994

119                                                                                           120
-continued ( i i i ) HYPOTHETICAL: NO ( i v ) ANTI-SENSE: NO ( v i ) ORIGINAL SOURCE:
    ( A ) ORGANISM: Anacystis nidulans ( x i ) SEQUENCE DESCRIPTION: SEQ ID NO:116:

| GACGGGCTCA | AGCCAGTTCA | GCGGCGCATC | CTTTATGCCA | TGCATGAACT | GGGTTTGACC | 60 |
|---|---|---|---|---|---|---|
| CCCGATCGCC | CCTTCCGCAA | AAGTACGCGG | GTGGTGGGTG | ACGTACTGGG | TAAGTATCAT | 120 |
| CCCCACGGCG | ATCAGGCAGT | TTACGACGCG | CTTGTGCGCT | TGGTACAGGA | CTTTAGCAGT | 180 |
| CGCTATCCCT | TGCTGGCGGG | GCATGGCAAC | TTTGGCTCGA | TCGATAACGA | TCCGCCCGCC | 240 |
| GCGATGCGCT | ACACCGAGAC | GCGCTTAGCG | CCGGTGAGTC | ATGTGGCACT | GCTGGAAGAA | 300 |
| ATCGGCGAAG | AAACCGTTGA | TTTTGTTGCC | AACTTCGACA | ACTCCCAACA | GGAGCCTTCA | 360 |
| GTTCTCCCGG | CTCAGCTTCC | GTTCCTGCTG | CTGAATGGTT | GCTCGGGAAT | CGCTGTCGGT | 420 |
| ATGGCA | | | | | | 426 |

( 2 ) INFORMATION FOR SEQ ID NO:117:

( i ) SEQUENCE CHARACTERISTICS:
        ( A ) LENGTH: 417 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Anabaena ( x i ) SEQUENCE DESCRIPTION: SEQ ID NO:117:

| AAGCCTGTGC | ATCGTCGCAT | CCTCTACGCC | ATGCACGAAT | TGGGTTTAAC | CCACGATCGC | 60 |
|---|---|---|---|---|---|---|
| CCTTTTAAGA | AATGCGCCCG | TGTGGTCGGG | GAAGTGTTGG | GTAAATATCA | CCCCCACGGC | 120 |
| GACACAGCAG | TATATGATGC | CTTGGTGCGG | ATGGCGCAGG | ATTTTCCAT | GCGATCGCCC | 180 |
| TTAGTCAACG | GACATGGTAA | CTTCGGTTCT | GTAGATAACG | ATCCCCGGC | GGCAATGCGT | 240 |
| TATACAGAAT | GTCGCCTACA | AGCCCTAACC | AGTTCCGCCC | TCCTCCAAGA | CATCGAATCA | 300 |
| GAAACAGTAG | ATTTTGCTGA | TAACTTCGAT | GGTTCCCAAC | AAGAACCCAC | AGTTTTGCCA | 360 |
| TCTCGTATTC | CCCAGTTACT | ACTAAATGGT | TCTTCGGGTA | TCGCTGTCGG | TATGGCA | 417 |

( 2 ) INFORMATION FOR SEQ ID NO:118:

( i ) SEQUENCE CHARACTERISTICS:
        ( A ) LENGTH: 426 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Anabaena ( x i ) SEQUENCE DESCRIPTION: SEQ ID NO:118:

| GATGGGCTGA | AGCCAGTTCA | TCGGCGGATT | TTATATGCCA | TGCACGAACT | TGGTTTGACC | 60 |

```
CCCGATAGAC  CATACCGGAA  ATGCGCCCGT  GTGGTGGGGG  ATGTGCTGGG  TAAATACCAC      120

CCTCATGGCG  ATCAAGCTGT  TTATGATGCT  TTGGTGAGGC  TGGTGCAGGA  TTTTTCCAGC      180

CGTTACCCTT  TACTGGGTGG  ACATGGCAAT  TTTGGCAGCG  TCGATAATGA  CCCACCGGCG      240

GCGATGCGTT  ACACAGAAAC  GCGCCTAGCT  CCCATTAGTC  ATGAGGGAAT  GCTGACAGAA      300

ATTGGTGAAG  AAACTGTGGA  ATTTGTGGGT  AACTTTGATA  ACTCCAACA   AGAGCCGACA      360

GTATTACCTG  CTCAGTTACC  GTTTTATTG   CTGAATGGTT  GTTCCGGCAT  AGCGGTAGGT      420

ATGGCA                                                                     426
```

( 2 ) INFORMATION FOR SEQ ID NO:119:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bdellovibrio bacteriovorus ( x i ) SEQUENCE DESCRIPTION: SEQ ID NO:119:

```
GATGGGCTGA  AGCCGGTCCA  CCGCCGTGTC  TTGTTTGCTC  AAAGTGAAAT  GAACAACCGC      60

CACGACAGAC  CGTACTTGAA  GTCGGCCCGT  GTGGTCGGCG  ACGTGATCGG  TAAATATCAC      120

CCGCACGGTG  ATGCTTCCGT  TTACGATACC  ATGGTTCGTA  TGGCCCAGGA  CTTCTCCCTG      180

CGCTACCCGC  TTGAGGATGG  TCAGGGAAC   TTCGGTTCCA  TCGACGGTGA  CTCTCCGGCA      240

GCTATGCGTT  ACACCGAGAT  CCGTTTGACC  GCTTTGGCAG  AAGAACTGCT  GAATGATCTG      300

GAAAAGAAA   CTGTTTCTTT  CGGTCCGAAC  TACGATGACT  CTTTGTTGAT  CCCGACGGTT      360

CTTCCATCCA  AGTTCCCGAA  CTTGCTGGTG  AACGGTTCTG  CGGGTATCGC  GGTCGGTATG      420

GCA                                                                        423
```

( 2 ) INFORMATION FOR SEQ ID NO:120:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Borrelia garinii ( x i ) SEQUENCE DESCRIPTION: SEQ ID NO:120:

```
GATGGGTTCA  AGCCTGTTCA  TAGGAGAATA  CTTTATTCTA  TGTATGAAAT  GGGACTTCGT      60

TCTGATAAAG  CTTTTAAAAA  AGCTGGAAGA  ATAGTAGGGG  ATGTTCTTGG  TAAATATCAT      120

CCCCATGGAG  ATCAATCAAT  TTATGATGCT  CTTGTAAGAC  TTGCTCAAGA  CTTTTCACTT      180

AGATATCCTG  TAATACGGGG  ACAGGGAAAT  TTTGGATCTA  TTGACGGAGA  TCCTCCTGCT      240

GCTATGCGAT  ATACTGAAGC  TAAAATGGAA  AGAATAACTG  AGTATATTGT  TAAGGATATA      300
```

| GACAAAGAGA | CTGTTAATTT | TAAGTCTAAT | TATGATGATT | CTTTAAGTGA | GCCTGAGATC | 360 |
| ATGCCTTCAT | CATTCCCATT | TCTTTTGGTA | AATGGCTCTA | GTGGCATCGC | TGTTGGTATG | 420 |
| GCG | | | | | | 423 |

( 2 ) INFORMATION FOR SEQ ID NO:121:

( i ) SEQUENCE CHARACTERISTICS:
        ( A ) LENGTH: 396 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Borrelia garinii ( x i ) SEQUENCE DESCRIPTION: SEQ ID NO:121:

| GATGGGTTTA | AGCCCGTCCA | AAGGAGAATT | ATACATTCTC | TTTTGAAAT | GCATGATGGT | 60 |
| AATTTTCATA | AAGTTGCAAA | TGTTGTTGGT | AATACAATGA | AATACCATCC | TCACGGTGAT | 120 |
| ACGTCAATTT | ATGAGGCTCT | TGTTAATATT | GCCAACAAGG | ATCTATTTAT | TGAAAAGCAA | 180 |
| GGCAATTTTG | GAAATTTATT | GACAGGTGAT | CCTGCTTCTG | CTTCTCGATA | TATTGAATGT | 240 |
| AGATTGACCC | CTTTAGCTTT | TGATGTTCTT | TACAGCAAAG | AGATAACAGT | TTATGAATCT | 300 |
| TCTTATGATG | GAAGAAATAA | TGAACCTTTG | CTTTATCCTG | CAAAAATTCC | TGTTATTTTA | 360 |
| ATTCAGGGAA | GCGAGGGTAT | AGCAGTTGGT | ATGGCG | | | 396 |

( 2 ) INFORMATION FOR SEQ ID NO:122:

( i ) SEQUENCE CHARACTERISTICS:
        ( A ) LENGTH: 428 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bordetella pertussis ( x i ) SEQUENCE DESCRIPTION: SEQ ID NO:122:

| GATGGGCTTA | AGCCGGTGCA | TCGCCGCGTG | CTGTACGCGA | TGCACGAACT | GAACAACGAT | 60 |
| TGGAACCGTG | CCTATAAGAA | GTCCGCGCGT | ATCGTCGGGG | ACGTCATCGG | TAAGTACCAC | 120 |
| CCGCACGGCG | ACCGGTCGGT | ATACGACACC | ATCGTCCGCA | TGGCGCAGGA | CTTCTCCATG | 180 |
| CGCTACATGC | TGGTCGACGG | CCAGGGCAAC | TTCGGCTCCA | TCGACGGCGA | CAACGCCGCG | 240 |
| GCGATGCGCT | ACACCGAAAT | CCGCCTGGCC | AAGATCGCGC | ACGAGTTGCT | GGCCGATATC | 300 |
| GACCAGGAAA | CGGTCGACTT | CGGGCCCAAC | TACGACGGCA | GCGAACAGGA | GCCCCTGCTG | 360 |
| CTGCCTTCGC | GCCTGCCCAA | CCTGCTGGTC | AACGGCAGCT | CGGGCATCGC | CGTGGGTATG | 420 |
| GCAAGCTT | | | | | | 428 |

( 2 ) INFORMATION FOR SEQ ID NO:123:

( i ) SEQUENCE CHARACTERISTICS:
    ( A ) LENGTH: 423 base pairs
    ( B ) TYPE: nucleic acid
    ( C ) STRANDEDNESS: double
    ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Borrelia afzelii ( x i ) SEQUENCE DESCRIPTION: SEQ ID NO:123:

| | | | | | | |
|---|---|---|---|---|---|---|
| GATGGGTTCA | AACCTGTCCA | CAGGAGAATA | CTTTATTCTA | TGTATGAGAT | GGGACTGCGT | 60 |
| TCTGATAAAG | CTTTTAAAAA | AGCTGGAAGA | ATAGTAGGGG | ATGTTCTTGG | GAAATATCAT | 120 |
| CCCCATGGAG | ATCAATCAAT | TTACGATGCT | CTTGTAAGAC | TTGCTCAAGA | TTTTTCACTT | 180 |
| AGATATCCTG | TAATACGGGG | GCAGGGAAAT | TTTGGATCTA | TTGATGGAGA | TCCTCCTGCT | 240 |
| GCTATGCGAT | ACACTGAAGC | TAAAATGGCA | AGAATAGCTG | AATATATTGT | TAAGGATATA | 300 |
| GACAAAGAGA | CTGTTAATTT | TAAGTCTAAT | TATGACGATT | CTTTAAGTGA | GCCTGAGATT | 360 |
| ATGCCTTCAT | CATTTCCATT | TCTTTTGGTA | AATGGCTCTA | GTGGTATAGC | GGTGGGTATG | 420 |
| GCG | | | | | | 423 |

( 2 ) INFORMATION FOR SEQ ID NO:124:

( i ) SEQUENCE CHARACTERISTICS:
        ( A ) LENGTH: 396 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Borrelia afzelii ( x i ) SEQUENCE DESCRIPTION: SEQ ID NO:124:

GATGGGTTCA AGCCGGTACA AAGGAGAATT ATACATTCTC TTTTTGAAAT GCATGATGGT 60

AATTTCCATA AAGTTGCGAA TGTTGTTGGC AATACAATGA AATACCATCC TCACGGCGAT 120

ACGTCAATTT ATGAGGCCCT TGTTAATATT GCTAACAAAG ATCTATTTAT TGAAAAGCAG 180

GGTAATTTTG GCAATTTATT TACAGGTGAT CCTGCTTCTG CCTCTCGATA TATTGAGTGC 240

AGATTAACCC CTTTAGCTTT TGATGTTCTT TACAGTAAAG AGATAACAAT TTATGAATCT 300

TCTTATGATG GAAGAAATAA TGAACCTTTG CTTTATCCTG CAAAAATTCC TGTTATTTTA 360

ATTCAGGGAA GTGAGGGTAT CGCGGTGGGT ATGGCG 396

( 2 ) INFORMATION FOR SEQ ID NO:125:

( i ) SEQUENCE CHARACTERISTICS:
( A ) LENGTH: 423 base pairs
( B ) TYPE: nucleic acid
( C ) STRANDEDNESS: double
( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Coxiella burnetti ( x i ) SEQUENCE DESCRIPTION: SEQ ID NO:125:

| | | | | | | |
|---|---|---|---|---|---|---|
| GATGGGTT

| | | | | | |
|---|---|---|---|---|---|
| CCCGACGCCG | CCGCGCGCAA | GTGCGCCAAG | GTGGTCGGCG | AGGTGATGGG | TAACTTCCAC | 120
| CCGCACGGCG | ACCAGTCGAT | CTATGACGCC | CTGGTGCGCC | TGGCGCAGGA | CTTTGCGCAG | 180
| CGCATCCCGC | TGGTCGAAGG | GCAGGGGAAC | TTCGGCAATA | TCGACGGCGA | TAACGCCGCA | 240
| GCCATGCGTT | ACACCGAATG | CAAGATGACG | GAGGCGGCGA | CGCTTCTGCT | GGACGGCATC | 300
| GACGAGGACG | CGGTCGACTT | CCGCCCGACC | TATGACGGCC | AGGACGAAGA | GCCGGTCGTG | 360
| CTGCCCTCGG | GCTTCCCGAA | CCTGTTGGCC | AACGGCTCGT | CGGGCATCGC | AGTCGGTATG | 420
| GCA | | | | | | 423

( 2 ) INFORMATION FOR SEQ ID NO:128:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Campylobacter fetus ( x i ) SEQUENCE DESCRIPTION: SEQ ID NO:128:

| | | | | | |
|---|---|---|---|---|---|
| GATGGGCTAA | AGCCGGTGCA | TCGTCGCATA | CTTTATGCTA | TGAACGATCT | TGGCGTAGGT | 60
| AGTCGCAGCC | CATATAAAAA | GTCTGCTCGT | ATAGTAGGTG | ATGTTATCGG | TAAGTATCAC | 120
| CCGCACGGCG | ATACTGCGGT | ATATGACGCT | TTAGTTAGAA | TGGCTCAGAA | CTTTTCTATG | 180
| AGAGTTCCTG | CAGTAGATGG | TCAAGGAAAC | TTTGGCTCAG | TCGATGGCGA | TGGCGCAGCC | 240
| GCTATGCGTT | ATACTGAAGC | TAGAATGACG | GTTTTGGCAG | AGGAACTTTT | AAGAGATTTA | 300
| GATAAAGATA | CGGTTGATTT | TATACCAAAT | TATGATGATA | GTTAAGCGA | ACCAGATGTT | 360
| TTACCCGCGC | GCGTACCGAA | TTTGTTGTTA | AATGGATCGA | GCGGAATCGC | TGTTGGTATG | 420
| GCA | | | | | | 423

( 2 ) INFORMATION FOR SEQ ID NO:129:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Chloroflexus aurantiacus ( x i ) SEQUENCE DESCRIPTION: SEQ ID NO:129:

| | | | | | |
|---|---|---|---|---|---|
| GATGGGCTTA | AGCCGGTGCA | GCGCCGTATC | CTCTACGGCA | TGTGGGACAT | GGGACTTCGC | 60
| AGTAATCAGC | CATACAAAAA | GAGTACCCGT | ATCGTGGGCG | ATGTGCTCGG | TAAAATGCAC | 120
| CCCCACGGTG | ACAGTACCGT | CTACGATGCG | CTGGCCCGCA | TGGCTCAGCC | CTGGAGTATG | 180
| CGGTATCCCC | TGATCGATGG | CCAGGGTAAC | TTCGGTTCCA | TCGATGGCGA | ATCCGCCGCA | 240
| GCGATGCGCT | ACACCGAAGC | GCGCCTGGAC | CCAATTGCCG | AAGAGTTGCT | CAGTGAGATT | 300

```
GAGAAAGATA  CCGTCGATTT  TCGTGATAAC  TTCGATGGCA  GCTACCGCGA  GCCGGTCGTG    360

CTCCCGGCCA  TTCTGCCCAA  TCTGCTGCTC  AACGGTGCTT  CCGGGATTGC  TGTTGGTATG    420

GCA                                                                       423
```

( 2 ) INFORMATION FOR SEQ ID NO:130:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Chlorobium limicola ( x i ) SEQUENCE DESCRIPTION: SEQ ID NO:130:

```
GATGGGCTGA  AGCCGGTGCA  TCGCCGTGTG  CTGTACGGTA  TGCACGAGCT  TGGCCTCCAG    60

TCAAACAAGC  CTCACAAGAA  ATCGGCTCGC  GTGGTCGGTG  AGGTGCTCGG  TAAGTATCAT    120

CCGCATGGTG  ACTCGGCTGT  TTACGACAGC  CTTGTTCGCA  TGGTGCAGGA  CTTCTCGCTG    180

CGCTATCCTC  TGATCGACGG  TCAAGGTAAC  TTCGGTTCGG  TCGATGGCGA  CTCTCCGGCG    240

GCGATGCGTT  ACACCGAGGT  GCGCATGAAG  GCGATCGCAG  GCGAAATGCT  CAAGGATCTC    300

GACAAGGAGA  CGGTCGATTT  CGCGCTGAAC  TTCGACGATT  CGCTCGAAGA  GCCGACGGTG    360

CTTCCCTCGG  CGATTCCGAA  CCTGCTGGTG  AACGGTGCTT  CGGGGATCGC  CGTCGGTATG    420

GCA                                                                       423
```

( 2 ) INFORMATION FOR SEQ ID NO:131:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Chlorobium tepidum ( x i ) SEQUENCE DESCRIPTION: SEQ ID NO:131:

```
GATGGGCTTA  AGCCGGTGCA  TCGCCGCGTG  CTTTACGGCA  TGCACGAGCT  GGGTCTGCAG    60

GCGGGCAAGC  CGTACAAGAA  ATCGGCTCGT  GTCGTCGGTG  AAGTGCTCGG  TAAGTATCAC    120

CCGCATGGCG  ACTCCGCTGT  TTACGACAGT  CTTGTGCGCA  TGGTGCAGGA  TTTTTCGCTG    180

CGTTATCCGC  TGATCGACGG  CCAGGGCAAC  TTCGGCTCGG  TCGATGGCGA  CTCCCCTGCG    240

GCCATGCGTT  ACACCGAGGT  GCGCATGAAG  GCCATCGCTG  GCGAGATGCT  CAAGGACCTC    300

GACAAGGAGA  CGGTTGATTT  CTCGCTCAAC  TTCGACGATT  CGCTCGAAGA  GCCAACGGTG    360

CTTCCGGCGG  CGATTCCGAA  CCTGCTGGTC  AATGGCGCTT  CGGGCATCGC  CGTCGGTATG    420

GCA                                                                       423
```

(2) INFORMATION FOR SEQ ID NO:132:

(i) SEQUENCE CHARACTERISTICS:
        (A) LENGTH: 396 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
        (A) ORGANISM: Chlamydia pneumoniae (xi) SEQUENCE DESCRIPTION: SEQ ID NO:132:

```
GATGGGTTTA AGCCCGTTCA GCGTCGACTT CTATGGACTT TATTCCTTAT GGACGACGGG      60
AAAATGCATA AAGTTGCCAA TATTGCAGGA AGAACTATGG CTCTCCATCC CCATGGCGAT     120
GCCCCTATTG TTGAAGCTCT TGTTGTCTTA GCAAATAAAG GCTACCTCAT CGACACGCAA     180
GGAAACTTCG GAAATCCCCT TACGGGAGAT CCTCACGCTG CTGCCCGTTA TATAGAAGCA     240
CGACTCAGTC CTTTAGCTCG AGAAACGCTC TTTAATACCG ACTTGATAGC TTTTCATGAC     300
TCTTATGATG GAAGAGAAAA AGAACCTGAT ATTTACCTG  CAAAGCTCCC CGTGCTTTTA     360
CTTCATGGTG TGGACGGCAT TGCAGTTGGT ATGGCA                               396
```

(2) INFORMATION FOR SEQ ID NO:133:

(i) SEQUENCE CHARACTERISTICS:
        (A) LENGTH: 423 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
        (A) ORGANISM: Corynebacterium pseudodiptheriae (xi) SEQUENCE DESCRIPTION: SEQ ID NO:133:

```
GATGGGTTGA AGCCGGTCCA CCGCCGCGTC ATCTACGCCA TGTGGGACGG CGGCTACCGT      60
CCCGACTCGG CTTTCTCGAA GTCGGTGAAG ATCGTCGGCG ACGTCATGGG TAACTATCAC     120
CCGCACGGCG ACGCCGCTAT CTACGACACG ATGGTGCGCA TGGTTCAGCC GTGGAATCTG     180
CGCTACCCGC TCGTGGCAGG CCAGGGTAAC TTCGGAACAG CGGGTGACCT AGGAGCGGCA     240
GCGCCCAGGT ACACCGAGGC CAGGATGGCT CAGCTGGCCG TAGAAATGGT TCGCGACATC     300
AACGAAGATA CCGTTGATTT TCAGCCGAAC TTTGACGGTT CAGTTCAAGA GCCGGTGGTG     360
CTGACCAGCC GCATTCCCAA CCTGCTCATC AACGGATCCG AAGGCATAGC CGTTGGTATG     420
GCG                                                                  423
```

(2) INFORMATION FOR SEQ ID NO:134:

(i) SEQUENCE CHARACTERISTICS:
        (A) LENGTH: 425 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
    (A) ORGANISM: Corynebacterium pseudodiptheriae (xi) SEQUENCE DESCRIPTION: SEQ ID NO:134:

| | | | | | |
|---|---|---|---|---|---|
| GATGGGTTAA | AGCCGGTACA | GCGGCGAATC | CTGTTCCAGA | TGGATCGTAT | GGGCTTGCGC | 60 |
| CCGGACAAGG | GGCATGTGAA | GTCCTCGCGC | GTCATTGGCG | ACGTCATGGG | CCGCCTCCAT | 120 |
| CCACACGGTG | ACGCCGCCAT | CTACGACGCA | ATGGTGCGCC | TCTCCCAGCC | CTTCACCATG | 180 |
| CTGCTACCTA | TGGTCGATGG | CCACGGCAAC | TTCGGCTCTC | TCGACGACGG | CCCTGCTGCG | 240 |
| CCGCGGTACA | CCGAGGTTCG | CATGGCTCCG | GCTGCGCTAG | CTATGACGGC | GAGTCTCGAC | 300 |
| GAGGACGTCG | TCGATATGGT | TCCCAATTAC | GACAACACCT | ACATGCAGCC | GGAGGTATTA | 360 |
| CCCGCCGCCA | TCCCTAACCT | GCTCGTCAAT | GGCTCCTCCG | GCATCGCGGT | AGGTATGGCA | 420 |
| AGCTT | | | | | | 425 |

(2) INFORMATION FOR SEQ ID NO:135:

(i) SEQUENCE CHARACTERISTICS:
        (A) LENGTH: 423 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
        (A) ORGANISM: Caulobacter subvibroides (xi) SEQUENCE DESCRIPTION: SEQ ID NO:135:

| | | | | | |
|---|---|---|---|---|---|
| GACGGGCTGA | AGCCAGTGCA | CCGGCGCATC | CTGTATTCGA | TGCACGACCT | GAACATGACG | 60 |
| CCGGAGCGCT | CGTACTCGAA | GTGTGCCCGC | GTGGTCGGTG | ACGTGCTGGG | CCGGTTCCAC | 120 |
| CCCCACGGCG | ATGCCTCGGT | CTATATGGCC | CTGGTACGGA | TGGCGCAGCC | GTTCTCGATG | 180 |
| GGGCTGATGC | TGATCGACGG | CCAGGGCAAC | TTCGGCTCCG | TCGACGGCGA | TATGCCCGCC | 240 |
| TCGATGCGTT | ATACCGAGGC | CCGGATGGCC | CCGGCCGCCA | GCGCCTTGCT | GACCGACATC | 300 |
| GACAAGGACA | CCGTCGATTT | CCAGCCGAAC | TACGACGAGA | AGGAGCTGGA | GCCCGTCGTC | 360 |
| CTGCCGGCGC | GGATCCCGAA | CCTGCTTGTC | AATGGTGCCG | GCGGCATAGC | CGTCGGTATG | 420 |
| GCA | | | | | | 423 |

(2) INFORMATION FOR SEQ ID NO:136:

(i) SEQUENCE CHARACTERISTICS:
        (A) LENGTH: 424 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
        (A) ORGANISM: Caulobacter subvibroides (xi) SEQUENCE DESCRIPTION: SEQ ID NO:136:

```
GATGGGTTTA  AGCCCGTTCA  CCGCCGCATC  CTGTACGCCA  TGCACCAGAT  GCGGCTGAAC     60

CCGCAGGCGG  CGGCGCGGAA  GTGCGCCAAG  GTCGTGGGCG  AGGTGATGGG  CGGCTATCAC    120

CCGCACGGCG  ACGCCTCCAT  CTATGACGCT  CTGGTCCGCC  TGGCGCAGGA  CTTCGCGCAG    180

AGCTACCCGT  TGGTCGACGG  GCAGGGCAAT  TTCGGCAACA  TCGACGGCGA  TAACGCCGCG    240

GCAATGCGCT  ACACCGAGTG  CAAGCTGACG  GCCGCATCAG  TCCTTCTGAT  GGAGGGAATC    300

GATCAGGATT  CCGTGGACTT  CCGTCCCACC  TATGACGATC  AGGATGAAGA  GCCGACCGTC    360

CTTCCGGCGG  GCTTCCCGAA  CCTGCTGGCG  AATGGATCGT  CGGGGATAGC  CGTTGGTATG    420

GCGA                                                                     424
```

(2) INFORMATION FOR SEQ ID NO:137:

(i) SEQUENCE CHARACTERISTICS:
        (A) LENGTH: 423 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
        (A) ORGANISM: Deinococcus radiodurans (xi) SEQUENCE DESCRIPTION: SEQ ID NO:137:

```
GACGGGTTTA  AGCCGGTGCA  GCGCCGCATC  ATGTACGCGA  TGTTGCAAGA  AGGGCTGATG     60

AGCAACGTCA  AGCACGCCAA  GTCCGCCAGC  GTGGTGGGCG  AAGTGATGAA  GCGTTACCAC    120

CCCCACGGCG  ACAGCTCCAT  CTACGACGCG  ATGGTGCGGC  TCGGGCAGTG  GTGGAACATG    180

CGGTACACTC  TGGTCGATCC  CCAGGGCAAC  TTCGGGTCTA  TGGACGGCGA  TATGGCCGCC    240

GCCATGCGCT  ACACCGAAGC  CCGCATGACC  AAGGTGGCCG  AGGAGATCCT  GGCCGACCTC    300

GAAAAAGAGA  CGGTGGACCT  CAAGCCCAAC  TACGACGAGA  CGACCACCGA  GCCGACGGTG    360

CTGCCCAGCG  CCGTGCCCAA  CCTGCTCATC  AACGGCGCGT  CGGGCATCGC  TGTCGGTATG    420

GCA                                                                      423
```

(2) INFORMATION FOR SEQ ID NO:138:

(i) SEQUENCE CHARACTERISTICS:
        (A) LENGTH: 423 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
        (A) ORGANISM: Helicobacter pyroli (xi) SEQUENCE DESCRIPTION: SEQ ID NO:138:

```
GATGGGTTCA  AACCAGTCCA  TAGGCGTATT  TTGTATGCGA  TGCATGAATT  AGGCCTTACT     60

TCCAAAGTCG  CTTATAAAAA  AAGCGCTAGG  ATCGTGGGTG  ATGTGATCGG  TAAATACCAC    120

CCCCATGGCG  ATAATGCGGT  TTATGATGCG  CTAGTGAGAA  TGGCGCAAGA  TTTTTCTATG    180

CGTTTGGAAT  TAGTGGATGG  GCAGGGCAAC  TTTGGCTCTA  TTGATGGCGA  TAACGCTGCA    240
```

| | | | | | |
|---|---|---|---|---|---|
| GCGATGCGTT | ACACTGAAGC | CAGAATGACT | AAGGCGAGTG | AAGAAATTTT | AAGGGATATT | 300
| GATAAAGACA | CCATTGATTT | TGTGCCTAAT | TATGATGACA | CCTTAAAAGA | GCCAGATATT | 360
| TTACCAAGCC | GTCTGCCTAA | CCTTTTAGTC | AATGGGGCTA | ATGGCATCGC | GGTGGGTATG | 420
| GCG | | | | | | 423

( 2 ) INFORMATION FOR SEQ ID NO:139:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Leptospira borgpetersenii ( x i ) SEQUENCE DESCRIPTION: SEQ ID NO:139:

| | | | | | |
|---|---|---|---|---|---|
| GATGGGTTGA | AGCCCGTTCA | TAGAAGAATC | CTTCATGCCA | TGAACGAACG | AGCGTGGAGA | 60
| AGCGATCGTC | CTTATGTGAA | ATGCGCTAAG | ATTGTGGGGG | AAGTGATTGG | TAATTATCAC | 120
| CCGCACGGAG | ATGCGTCTGT | TTATGAAGCT | CTTGTAAGAA | TGGTTCAGGA | TTTTTCCCTG | 180
| CGCGTTCCAT | TGATTGATGG | GCAAGGAAAT | TTCGGTTCTA | TAGACGGCGA | TAACCCTGCG | 240
| GCTTATCGGT | ACACCGAAGC | AAGACTTGAA | AAAGTCGCGG | AAGAATTGTT | ACGCGACATT | 300
| GAAAAAGAGA | CCGTTAGTTT | CTCGCCTAAT | TACGATGATA | CAAAACAACA | ACCGGACGTA | 360
| TTACCCGCAA | ATTTTCCGAA | TTTACTCGTA | AATGGATCTT | CCGGGATCGC | TGTTGGTATG | 420
| GCG | | | | | | 423

( 2 ) INFORMATION FOR SEQ ID NO:140:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Listeria monocytogenes ( x i ) SEQUENCE DESCRIPTION: SEQ ID NO:140:

| | | | | | |
|---|---|---|---|---|---|
| GATGGGTTAA | AACCGGTACA | CCGTCGGATT | TTATATGCGA | TGAATGACTT | AGGTATGACT | 60
| TCTGATAAAG | CCTATAAAAA | ATCGGCTCGT | ATCGTTGGTG | AAGTAATCGG | TAAGTATCAC | 120
| CCCCACGGCG | ATACAGCGGT | TTATTTTACA | ATGGTACGTA | TGGCGCAAGA | TTTTAGTTAC | 180
| CGTAATATGC | TAGTTGATGG | ACATGGTAAC | TTTGGTTCGG | TCGATGGCGA | TATGGCGGCA | 240
| GCGATGCGTT | ATACAGAAGC | ACGTATGTCA | AAAATTTCGA | TGGAACTTCT | CGCGATATT | 300
| AACAAAGATA | CAATTGATTA | CGCTGATAAC | TACGATGGTT | CTGAACGTGA | GCCAGTTATT | 360
| TTACCAGCGC | GTTTCCCTAA | CTTACTAGTC | AATGGTTCGT | CAGGTATCGC | CGTAGGTATG | 420
| GCA | | | | | | 423

( 2 ) INFORMATION FOR SEQ ID NO:141:

( i ) SEQUENCE CHARACTERISTICS:
        ( A ) LENGTH: 424 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Listeria monocytogenes ( x i ) SEQUENCE DESCRIPTION: SEQ ID NO:141:

```
GATGGGCTGA  AGCCTGTGCA  ACGTCGTATA  TTATTCGCAA  CGAATGTCGA  AGGAAATACT     60
GCTGAGAAAG  GTTTCCGCAA  ATCTGCCAAA  ACAGTCGGAA  ATGTTATCGG  TAACTACCAT    120
CCACATGGTG  ACTCTTCGGT  TTACGAAGCA  ATGGTACGGA  TGAGTCAAGA  CTGGAAAGTA    180
CGTAACATGC  TGATTGAAAT  GCATGGTAAT  AACGGTAGTG  TCGACGGGGA  TCCACCGGCA    240
GCAATGCGTT  ATACAGAAGC  GCGCCTTTCC  CCAATTTCAG  CAGAACTTTT  GCGCGATATT    300
GAAAAAGAAA  CAGTCGATTT  TATTCCTAAC  TTTGATGATA  CATTCAGTGA  GCCAACTGTT    360
TTACCAGCAC  GTTTTCCAAA  CCTTTTAGTG  AATGGTTCTA  CTGGCATCTC  TGCAGATTAT    420
GCGA                                                                    424
```

( 2 ) INFORMATION FOR SEQ ID NO:142:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Mycoplasma arthritidis ( x i ) SEQUENCE DESCRIPTION: SEQ ID NO:142:

```
GATGGGTTTA  AACCAGTTCA  TAGAAGAGTT  TTGTATGCAG  CTTATAACTT  AGGAATGACA     60
CATGATAAAC  CTCACAAAAA  GTCAGCTAGA  CTTGTTGGGG  AAGTAATCGG  TAAGTTCCAC    120
CCACATGGTG  ATTCTGCAGT  TTATGAAACT  ATGGTTAGAA  TGGCACAAGA  TTTTTCAATG    180
AGATATTTAT  TAGTTGATGG  TCATGGTAAC  TTTGGTTCAA  TTGATGGTGA  CTCTGCAGCT    240
GCAATGAGAT  ATACAGAAGC  AAGATTATCT  AAAATATCTA  ATGAAATGTT  AAAAAACATT    300
GAAAAAGATA  CAATTGATTT  TATTGATAAC  TATGATGGTA  GTGAACAAGA  ACCATCAGTA    360
TTACCAGCTT  TATTTCCAAA  TTTATTAGCT  AATGGAACAT  CAGGGATTGC  TGTTGGTATG    420
GCG                                                                     423
```

( 2 ) INFORMATION FOR SEQ ID NO:143:

( i ) SEQUENCE CHARACTERISTICS:
        ( A ) LENGTH: 423 base pairs
        ( B ) TYPE: nucleic acid
        ( C ) STRANDEDNESS: double ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Mycoplasma arthritidis ( x i ) SEQUENCE DESCRIPTION: SEQ ID NO:143:

| | | | | | |
|---|---|---|---|---|---|
| GATGGGTTCA | AGCCAGTCCA | AAGAAGAATT | TTATATGCTA | TGAATGAATT | AAAAATTCAT | 60 |
| CATGATAAAC | CATATAAAAA | ATCAGCTAGA | ACAGTTGGGG | AAGTAATTGG | TAAATATCAC | 120 |
| CCACATGGTG | ATAGTTCAAT | TTATGAAGCT | ATGGTTAGAA | TGTCTCAGGA | ATGAAAGAAC | 180 |
| AATATCCCAT | TACTTGATAT | GCAAGGTAAC | AAAGGTTCTC | TTGATGGTGA | TGGACCAGCA | 240 |
| GCGATGAGAT | ATACAGAGTG | TAGACTTTCT | TTATTTGGAG | AGCTTATGCT | TGAAGATATT | 300 |
| GATAAAGATA | CAGTTAAATT | CATTCCTAAC | TTTGATGATT | CTGAAAGTGA | ACCATCTATT | 360 |
| TTACCATCTC | TTTTGCCAAA | TGTTTTAGTT | AACGGTTCAA | CAGGCATAAC | TGCAGGTTAT | 420 |
| GCG | | | | | | 423 |

( 2 ) INFORMATION FOR SEQ ID NO:144:

( i ) SEQUENCE CHARACTERISTICS:
    ( A ) LENGTH: 423 base pairs
    ( B ) TYPE: nucleic acid
    ( C ) STRANDEDNESS: double
    ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Mycobacterium fortuitum ( x i ) SEQUENCE DESCRIPTION: SEQ ID NO:144:

| | | | | | |
|---|---|---|---|---|---|
| GATGGGTTCA | AGCCCGTGCA | CCGCCGCGTG | CTCTACGCGA | TGTACGACTC | CGGCTTCCGC | 60 |
| CCCGACCGCA | GCCACGCCAA | GTCGGCCCGC | TCGGTGGCCG | AGACGATGGG | TAACTACCAC | 120 |
| CCGCACGGTG | ACTCGTCGAT | CTACGACACC | CTGGTCCGGA | TGGCCCAGCC | GTGGTCACTG | 180 |
| CGCTATCCGC | TGGTCGACGG | TCAGGGCAAC | TTCGGTTCGC | CGGGTAACGA | TCCGCCAGCC | 240 |
| GCCATGCGTT | ACACCGAGGC | GCGGCTGACT | CCCCTGGCGA | TGGAGATGCT | GCGCGAAATC | 300 |
| GACGAGGAGA | CAGTCGATTT | CATCCCGAAC | TACGACGGTC | GGGTGCAGGA | GCCCACGGTT | 360 |
| CTGCCGAGCC | GGTTCCCCAA | CCTGCTGGCC | AACGGTTCGG | GCGGCATCGC | AGTCGGTATG | 420 |
| GCA | | | | | | 423 |

( 2 ) INFORMATION FOR SEQ ID NO:145:

( i ) SEQUENCE CHARACTERISTICS:
    ( A ) LENGTH: 423 base pairs
    ( B ) TYPE: nucleic acid
    ( C ) STRANDEDNESS: double
    ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Mycoplasma hominis ( x i ) SEQUENCE DESCRIPTION: SEQ ID NO:145:

| | | | | | | |
|---|---|---|---|---|---|---|
| GATGGGTTCA | AGCCGGTGCA | CCGTAGAATT | TTATATGGTA | TGAGTGAACT | TGGAATGTTT | 60 |
| TATACAGCGC | CACATAAAAA | ATCGGCAAGA | ATCGTCGGAG | ATGTTTTAGG | TAAATATCAC | 120 |
| CCACATGGAG | ATTCATCAGT | ATATGAAGCT | ATGGTAAGAA | TGGCTCAAGA | TTTTTCACTT | 180 |
| CGCTATCCTT | TAATTGATGG | ACACGGTAAC | TTTGGATCTG | TTGACGGAGA | CGAAGCTGCT | 240 |
| GCAATGCGTT | ATACAGAAGC | TAGAATGAGC | AAGATTGCTG | GTGCAATGGT | TGATGGTATT | 300 |
| AAGAAAAATA | CTGTTGACTT | TATGGACAAC | TATGACGCAA | CTGAAAAAGA | ACCAGTTGTC | 360 |
| TTGCCATCAC | GTTTCCCTAA | TTTATTAGTT | TCTGGTTCAA | GTGGAATAGC | GGTCGGTATG | 420 |
| GCA | | | | | | 423 |

( 2 ) INFORMATION FOR SEQ ID NO:146:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Mycoplasma hominis ( x i ) SEQUENCE DESCRIPTION: SEQ ID NO:146:

| | | | | | | |
|---|---|---|---|---|---|---|
| GACGGGTTGA | AACCGGTTCA | ACGTCGGATT | TTATATTCAA | TGTGAAATTT | ACATTTAAAA | 60 |
| AATAGCGAAC | CTTTTAAAAA | ATCAGCTAGA | ATCGTTGGGG | ATGTTATCGG | ACGTTATCAC | 120 |
| CCTCATGGAG | ATAGTTCAAT | ATACGAAGCA | TTAGTCAGAA | TGGCTCAAGA | TTGAAAAAGC | 180 |
| AATTTCCCAT | TAATTGAAAT | GCATGGTAAT | AAAGGTTCAA | TTGATGATGA | CCCTGCCGCT | 240 |
| GCAATGCGTT | ACACTGAATC | AAGACTTGAA | AAAATTAGTG | AACTGATGTT | GAAAGATTTA | 300 |
| GACAGAAAAG | TTGTAAAAAT | GGCTCCAAAC | TTTGATGACT | CTGAATACGA | ACCAATTGTT | 360 |
| TTGCCGGCCT | TATTTCCTAA | TTTATTAGTT | AACGGTGCTA | AAGGAATCAC | CGCCGGTTAT | 420 |
| GCG | | | | | | 423 |

( 2 ) INFORMATION FOR SEQ ID NO:147:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Micrococcus leteus ( x i ) SEQUENCE DESCRIPTION: SEQ ID NO:147:

| | | | | | | |
|---|---|---|---|---|---|---|
| GATGGGTTCA | AGCCTGTTCA | CCGTCGCGTG | CTCTACGCGA | TGTACGACGG | CGGCTACCGT | 60 |
| CCGGACCGTG | TGTTCAACAA | GTCCGCCCGC | GTGGTGGGCG | ACGTGATGGG | CAACTACCAC | 120 |

| CCGCACGGCG | ACACCGCGAT | CTACGACGCC | CTCGTGCGCC | TCATCCAGGA | CTGGGTCCAG | 180 |
| CGCTATCCCG | TGGCGCTCGG | CCAGGGCAAC | TTCGGCTCCC | CGGGCAACGA | CGGTGCGGCC | 240 |
| GCCCAGCGCT | ACACCGAGAC | CAAGATGGCC | CCGCTGGCCA | TGGAGATGGT | CCGGGACATC | 300 |
| GACGAGGACA | CCGTCGACAT | GCAGGACAAC | TACGACGGCA | AGCAGCAGGA | GCCCGTCGTC | 360 |
| CTGCCCGCCC | GGTACCCGAA | CCTGCTGGTC | AACGGCTCCT | CGGGAATCGC | TGTTGGTATG | 420 |
| GCA | | | | | | 423 |

( 2 ) INFORMATION FOR SEQ ID NO:148:

( i ) SEQUENCE CHARACTERISTICS:
( A ) LENGTH: 420 base pairs
( B ) TYPE: nucleic acid
( C ) STRANDEDNESS: double
( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Micrococcus leteus ( x i ) SEQUENCE DESCRIPTION: SEQ ID NO:148:

| GATGGGTTCA | AGCCGGTTCA | GCGGCGCATC | CTCTTCATGA | TGTCCCGCAT | GGGCCTGCGC | 60 |
| CCGGACCGGG | GCCACGTGAA | GTCCGCCCGC | GTGGTGGGCG | AGGTGATGGG | CAAGCTGCAC | 120 |
| CCCCACGGCG | ACGCCGCGAT | CTACGACGCG | ATGGTCCGCC | TCGCCCAGCC | GTTCTCCCTG | 180 |
| CGCCTGCCCG | TGGTGGACGG | GCACGGCAAC | TTCGGCTCGC | TCGACGACGG | CCCCGCGGCC | 240 |
| CCGCGCTACA | CGGAGGCCCG | CATGGCGCCG | GCGGCCCTGG | CGCTCACCGC | GGACCTCGAC | 300 |
| GAGGGCACCG | TGGACTTCGT | CCCCAACTAC | GACAACCAGT | TCCAGCAGCC | GGCCGTGCTG | 360 |
| CCCGCCGCCT | ACCCCAACCT | GCTCGTCAAC | GGCACCACCG | GCATCGCAGT | AGGTATGGCA | 420 |

( 2 ) INFORMATION FOR SEQ ID NO:149:

( i ) SEQUENCE CHARACTERISTICS:
( A ) LENGTH: 423 base pairs
( B ) TYPE: nucleic acid
( C ) STRANDEDNESS: double
( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Mycoplasma pneumoniae ( x i ) SEQUENCE DESCRIPTION: SEQ ID NO:149:

| GATGGACTTA | AACCTGTGCA | CCGCCGTGTG | CTCTATGGTG | CTTACACTGG | GGGCATGCAC | 60 |
| CACGATCGCC | CCTTTAAAAA | GTCAGCACGG | ATTGTCGGTG | ATGTAATGAG | TAAGTTCCAC | 120 |
| CCCCACGGGG | ACATGGCCAT | TTACGACACA | ATGTCGCGGA | TGGCGCAGGA | CTTTTCTTTG | 180 |
| CGTTACCTCT | TAATTGACGG | ACATGGTAAC | TTTGGCTCGA | TTGATGGCGA | TCGTCCCGCA | 240 |
| GCACAACGTT | ATACGGAAGC | ACGGTTGTCG | AAATTAGCGG | GGGAACTGTT | ACGTGACATT | 300 |
| GACAAGGACA | CGGTCGACTT | TGTCGCTAAC | TATGATGGGG | AAGAACAAGA | ACCAACGGTT | 360 |
| TTACCAGCTG | CCTTTCCTAA | TTTATTAGCT | AATGGTTCGA | GTGGGATTGC | GGTAGGGATG | 420 |

TCC                                                                                                              423

(2) INFORMATION FOR SEQ ID NO:150:

(i) SEQUENCE CHARACTERISTICS:
        (A) LENGTH: 423 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
        (A) ORGANISM: Mycoplasma pneumoniae (xi) SEQUENCE DESCRIPTION: SEQ ID NO:150:

```
GATGGGTTTA  AGCCAGTCCA  ACGCCGCATC  CTCTATGGCA  TGTACCAAAT  GGGCTTAAAA    60
CCCACTTCAC  CCTACAAAAA  GTCAGCTCGG  GCAGTCGGAG  AAATTATGGG  TAAGTACCAC   120
CCCCATGGCG  ATGCATCGAT  CTATGATGCG  ATTGTAAGGA  TGTCACAAGC  CTGAAAGAAC   180
AACCTCACTA  CTATCTCCAT  TCACGGGAAT  AATGGTTCCA  TAGATGGTGA  TAACGCTGCC   240
GCGATGCGCT  ATACCGAAGC  GCGTTAAGT   CCGTACGGGT  TTGAACTACT  CAAAGACATT   300
GAAAAGCAGT  TAGTACAGTT  TGTGAATAAC  TTTGATGACA  GTGAGGTCGA  ACCGAGCGTG   360
TTACCAACCC  TGTTACCTAA  CCTCTTTATT  AACGGTACCA  GTGGGATTGC  CGTGGGTATG   420
GCG                                                                      423
```

(2) INFORMATION FOR SEQ ID NO:151:

(i) SEQUENCE CHARACTERISTICS:
        (A) LENGTH: 423 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
        (A) ORGANISM: Mycobacterium smegmatis (xi) SEQUENCE DESCRIPTION: SEQ ID NO:151:

```
GACGGGCTGA  AGCCAGTTCA  CCGTCGCGTG  CTGTACGCGA  TGTACGACTC  GGGCTTCCGT    60
CCGGATCGCA  GCCACGCCAA  ATCCGCGCGC  TCCGTTGCCG  AGACGATGGG  TAACTACCAT   120
CCGCACGGCG  ACGCCTCGAT  CTACGACACC  CTGGTCCGCA  TGGCCCAGCC  GTGGTCGTTG   180
CGCTACCCGC  TGGTGGACGG  CCAGGGCAAC  TTCGGCTCGC  CGGGTAACGA  TCCGCCAGCG   240
GCCATGCGTT  ACACCGAAGC  GCGACTCACT  CCGTTGGCGA  TGGAGATGTT  GCGTGAAATC   300
GACGAGGAGA  CAGTCGATTT  CATCCCGAAC  TACGACGGAC  GGGTGCAGGA  GCCCACGGTT   360
CTGCCGAGCC  GGTTCCCCAA  CCTGTTGGCC  AACGGTTCGG  GCGGGATAGC  TGTCGGTATG   420
GCA                                                                      423
```

(2) INFORMATION FOR SEQ ID NO:152:

(i) SEQUENCE CHARACTERISTICS:
        (A) LENGTH: 423 base pairs

-continued ( B ) TYPE: nucleic acid
( C ) STRANDEDNESS: double
( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
 ( A ) ORGANISM: Myxococcus xanthus ( x i ) SEQUENCE DESCRIPTION: SEQ ID NO:152:

| | | | | | | |
|---|---|---|---|---|---|---|
| GATGGGTTTA | AGCCCGTGCA | TCGCCGCGTG | CTGTACGCGA | TGAATGACCT | GGGCAACCTC | 60 |
| CACAACCGGG | CCTACAAGAA | GTCCGCCCGC | GTGGTGGGTG | ACGTCATCGG | TAAGTACCAC | 120 |
| CCGCACGGTG | ACTCGTCGGT | GTACGACGCC | ATGGTGCGCC | TGGCGCAGGA | GTGGAGCCTT | 180 |
| CGCTACCTGC | TGGTGGACGG | CCAGGGCAAC | TTCGGCTCGG | TGGACGGCGA | CTCGCCAGCG | 240 |
| GCCATGCGTT | ACACGGAAGT | GCGCATGGAG | CGGCTGGCGG | AGGACCTGCT | GGCGGACATC | 300 |
| GACAAGGAGA | CGGTGGACTT | CGGTCCCAAC | TACGACGACT | CGCTGGAAGA | GCCGCTCGTC | 360 |
| CTCCCGTCGA | AGTTCCCCAA | CCTCCTGGTC | AACGGCAGCA | GCGGAATTGC | CGTCGGTATG | 420 |
| GCA | | | | | | 423 |

( 2 ) INFORMATION FOR SEQ ID NO:153:

( i ) SEQUENCE CHARACTERISTICS:
 ( A ) LENGTH: 426 base pairs
 ( B ) TYPE: nucleic acid
 ( C ) STRANDEDNESS: double
 ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
 ( A ) ORGANISM: Myxococcus xanthus ( x i ) SEQUENCE DESCRIPTION: SEQ ID NO:153:

| | | | | | | |
|---|---|---|---|---|---|---|
| GACGGGCTGA | AGCCGGTTCA | GCGCCGCATC | CTGTTCGGCA | TGTTCCACGA | CCACCGGCTG | 60 |
| ACGCACGAAG | CCAAGTACCA | GAAGTCCGCC | AAGGTGGTTG | GCAGTGTCAT | GGGTCAGTAC | 120 |
| CACCCGCACG | GTGACGCCTC | CATCTACGAG | GCGCTGGTGC | GCATGGCGCA | GGACTTCTCG | 180 |
| TTGCGCTACC | CGCTGGTGGA | CGGCCACGGC | AACTTCGGCT | CGCTCGACGG | CGACGGCGCG | 240 |
| GCGGCCATGC | GCTACACCGA | GTGCCGTCTG | GCGATGCTGT | CCAGCGAGCT | CCTGACGGAG | 300 |
| CTGGGCAAGA | AGACGGTGGC | CTTCCGGCCG | ACCTACGACG | GCACGCTGCA | GGAGCCGGTG | 360 |
| GTCATCCCCG | CGCGGGTGCC | GCAGTTGCTG | ATGAACGGCA | CCACGGGCAT | AGCCGTCGGT | 420 |
| ATGGCA | | | | | | 426 |

( 2 ) INFORMATION FOR SEQ ID NO:154:

( i ) SEQUENCE CHARACTERISTICS:
 ( A ) LENGTH: 423 base pairs
 ( B ) TYPE: nucleic acid
 ( C ) STRANDEDNESS: double
 ( D ) TOPOLOGY: Not Relevant ( i i ) MOLECULE TYPE: DNA (genomic)

( i i i ) HYPOTHETICAL: NO 5,645,994

153                                                                                                        154

-continued ( i v ) ANTI-SENSE: NO ( v i ) ORIGINAL SOURCE:
    ( A ) ORGANISM: Saccharothrix aerocolonigenes ( x i ) SEQUENCE DESCRIPTION: SEQ ID NO:154:

| | | | | | |
|---|---|---|---|---|---|
| GACGGGTTGA | AGCCAGTTCA | CGTGCGAGTG | CTGTACTCGA | TGTTCGACTC | CGGTTTCCGT | 60 |
| CCCGACCGCG | GCTACAACAA | GTGCGCGCGT | GTCGTCGGCG | ACGTGATGGG | CAACTACCAC | 120 |
| CCGCACGGTG | ACTCGGCGAT | CTACGACGCG | TTGGTGCGTC | TCGCCCAGCC | GTGGGCCCTG | 180 |
| CGGTACCCGT | TGATCGACGG | CCAGGGCAAC | TTCGGTTCCG | TGGGCAACGA | CCCCGCCGCG | 240 |
| GCCATGCGGT | ACACGGAATG | CCGGCTCTCC | CCGTTGGCCA | TGCACATGCT | GCAGGACATC | 300 |
| GAGGAAGACA | CCGTCGAGTT | CCGCGACAAC | TACGACGGCC | GCATCCAGGA | GCCGACGGTC | 360 |
| CTCCCGTCGC | GCATCCCGAA | CCTGCTGATC | AACGGCAGCT | CCGGCATTGC | CGTCGGTATG | 420 |
| GCA | | | | | | 423 |

( 2 ) INFORMATION FOR SEQ ID NO:155:

( i ) SEQUENCE CHARACTERISTICS:
        ( A ) LENGTH: 420 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Saccharothrix aerocolonigenes ( x i ) SEQUENCE DESCRIPTION: SEQ ID NO:155:

| | | | | | |
|---|---|---|---|---|---|
| GATGGGTTTA | AGCCAGTGCA | CCGTCGCATC | CTCTACTCGA | TGCACGACAA | CGGTCAGCGC | 60 |
| CCCAACACCC | CATACGTGAA | GTCGTCCCGC | GTGGTCAGTG | ACACCATGGG | TCGCTACCAC | 120 |
| CCGCATGGCG | ACACCGCGAT | CTACGACGCG | TTGGTTCGAC | TTGCACAGGA | CTTCAGTCTC | 180 |
| AACGAGCCGT | TGATCGACGG | ACATGGAAAT | TTTGGTAGCC | CAGACGATGG | ACCGGCTGCA | 240 |
| TCGCGTTACA | CCGAAGCGCG | GATGTCCCAG | GCTGCGATGC | ATCTCGTCGG | TGAACTGAAC | 300 |
| GAGGACACGG | TCGACTTCCG | GCCGAACTAC | GACGGCTCGC | TCGAAGAGCC | GTCGGTGCTG | 360 |
| CCGGCCGCGT | TCCCGAACCT | GCTGGTCAAC | GGCACGTCCG | GGATAGCAGT | CGGTATGGCA | 420 |

( 2 ) INFORMATION FOR SEQ ID NO:156:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Nocardia asteroides ( x i ) SEQUENCE DESCRIPTION: SEQ ID NO:156:

| | | | | | |
|---|---|---|---|---|---|
| GACGGGCTTA | AGCCGGTGCA | CCGGCGCGTG | CTCTACGCGA | TGTACGACAA | CGGCTACCGC | 60 |
| CCGGACCGCG | GTTACGTGAA | ATCCGCCCGC | CCGGTCGCCG | AGACCATGGG | TAACTATCAC | 120 |

```
CCGCACGGTG   ACGCGTCGAT   CTACGACACG   CTGGTCCGCA   TGGCCCAACC   GTGGTCGCTG        180

CGTTATCCGC   TCGTAGACGG   GCAGGGCAAC   TTCGGTTCCC   GCGGCAACGA   CGGTGCCGCC        240

GCGATGCGGT   ACACCGAGTG   CCGACTGACC   CCCCTCGCGA   TGGAACTGCT   GCGGGAAATC        300

GACCATGAGA   CGGTCGATTT   CACGCCCAAC   TACGACGGCC   GTTCCCAGGA   ACCCGTGGTG        360

CTTCCGAGCC   GGGTGCCGAA   CCTGCTCATG   AACGGCAGCA   ACGTATCGC    GGTTGGTATG        420

GCA                                                                               423
```

( 2 ) INFORMATION FOR SEQ ID NO:157:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Nocardia brasiliensis ( x i ) SEQUENCE DESCRIPTION: SEQ ID NO:157:

```
GATGGGTTTA   AGCCGGTTCA   CCGGCGGGTG   CTGTACGCGA   TGTACGACAA   CGGATATCGG         60

CCCGACCGCG   GTTACGTGAA   GTCCGCGCGC   CCGGTCGCCG   AGACCATGGG   TAACTACCAC        120

CCGCACGGTG   ACGCGTCGAT   CTACGACACC   CTCGTGCGCA   TGGCGCAGCC   GTGGTCGCTG        180

CGCTACCCGC   TGGTCGACGG   CCAGGGCAAC   TTCGGTTCGC   GCGGTAACGA   CGGCGCGGCC        240

GCCATGCGCT   ACACCGAGTG   CCGGCTGACC   CCGCTCGCGA   TGGAGATGCT   GCGCGAAATC        300

GACCACGAGA   CGGTCGATTT   CATCCCGAAC   TACGACGGTC   GCTCGCAGGA   GCCGACCGTG        360

CTGCCGAGCC   GGGTGCCCGC   GCTGCTGATG   AACGGCAGCA   ACGGCATCGC   AGTCGGTATG        420

GCA                                                                               423
```

( 2 ) INFORMATION FOR SEQ ID NO:158:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Nocardia otitdiscaviarum ( x i ) SEQUENCE DESCRIPTION: SEQ ID NO:158:

```
GATGGGCTGA   AGCCGGTGCA   CCGCCGGATC   ATGTACGCGA   TGTACGACAA   CGGGTATCGG         60

CCCGATCGCA   GCTATGTGAA   GTCGGCTCGC   CCGGTCGCCG   ACACCATGGG   CAACTACCAC        120

CCGCACGGTG   ACACGGCCAT   CTACGACACC   CTGGTGCGCA   TGGCGCAGCC   CTGGTCGCTG        180

CGCTACCCGC   TGGTGGACGG   TCAGGGCAAC   TTCGGTTCGC   GCGGCAACGA   CGGCGCGGCC        240

GCCATGCGCT   ACACCGAATG   CCGCCTGACC   CCGTTGGCCA   TGGAGCTGCT   GCGCGAAATC        300

GACCACGAGA   CGGTCGATTT   CCTGCCGAAC   TACGACGGCA   AGACGCAGGA   GCCGGTGGTG        360
```

| | | | | | | |
|---|---|---|---|---|---|---|
| CTCCCGGCCC | GCGTGCCGGT | GCTGCTCATG | AACGGCAGCA | ACGGCATCGC | TGTCGGTATG | 420 |
| GCA | | | | | | 423 |

( 2 ) INFORMATION FOR SEQ ID NO:159:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Nocardia farcinica ( x i ) SEQUENCE DESCRIPTION: SEQ ID NO:159:

| | | | | | | |
|---|---|---|---|---|---|---|
| GACGGGTTGA | AGCCAGTGCA | TCGCCGCATC | CTCTACGCGA | TGTACGACAA | CGGGTACCGC | 60 |
| CCCGATCGCG | GCTACGTGAA | GTCCGCCCGC | CCGGTGTCGG | ACACCATGGG | CAATTACCAC | 120 |
| CCGCACGGCG | ACTCGGCCAT | CTACGACACC | CTGGTGCGGA | TGGCGCAGCC | GTGGGCCATG | 180 |
| CGGTACCCGC | TGGTCGACGG | CCAGGGCAAC | TTCGGCAGCC | GCGGCAACGA | CGGCGCGGCC | 240 |
| GCCATGCGGT | ACACCGAGTG | CCGCCTCAGC | CCGCTGGCGA | TGGAGATGCT | GCGCGAAATC | 300 |
| GACCACGAGA | CGGTCGATTT | CATCCCGAAC | TACGACGGCA | AGACCCAGGA | ACCGGTCGTC | 360 |
| CTGCCCAGCC | GTGTGCCGAA | CATGCTGATG | AACGGCAGCA | ACGGCATTGC | AGTAGGTATG | 420 |
| GCA | | | | | | 423 |

( 2 ) INFORMATION FOR SEQ ID NO:160:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Oerskovia turbata ( x i ) SEQUENCE DESCRIPTION: SEQ ID NO:160:

| | | | | | | |
|---|---|---|---|---|---|---|
| GATGGGTTTA | AGCCTGTGCA | CCGCCGCGTG | CTCTACGCGA | TGTACGACGG | CGGGTACCGT | 60 |
| CCCGACCGCG | CGTTCTCCAA | GTGCAGCCGT | GTCGTCGGCG | ACGTCATGGG | CAAGTTCCAC | 120 |
| CCGCACGGCG | ACACAGCCAT | CTACGACGCG | CTCGTGCGTC | TCGTGCAGGA | CTGGTCGCTG | 180 |
| CGCTACCCCC | TGGTCGCGGG | GCAGGGGAAC | TTCGGCTCCC | CCGGCAACGA | CCCCGCGGCG | 240 |
| GCCCCGCGGT | ACACCGAGTG | CCGCATGGCC | CCGCTCGCCA | TGGAGATGGT | GCGGGACATC | 300 |
| GACAAGGAGA | CCGTCGACTT | CCAGGACAAC | TACGACGGCC | GCACCCAGGA | GCCCGTCGTC | 360 |
| CTGCCCGCGC | GCTTCCCGAA | CCTCCTGGTC | AACGGGTCGG | CCGGAATCGC | GGTCGGTATG | 420 |
| GCA | | | | | | 423 |

( 2 ) INFORMATION FOR SEQ ID NO:161:

(i) SEQUENCE CHARACTERISTICS:
  (A) LENGTH: 423 base pairs
  (B) TYPE: nucleic acid
  (C) STRANDEDNESS: double
  (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
  (A) ORGANISM: Propionibacterium acnes (xi) SEQUENCE DESCRIPTION: SEQ ID NO:161:

| | | | | | | |
|---|---|---|---|---|---|---|
| GATGGGTTTA | AACCGGTGCA | CCGTCGGGTC | ATCTACGCGA | TGTACGACGG | CGGTTACCGC | 60 |
| CCCGACCGCG | GCTGGAACAA | GTGCTCCCGC | GTCGTCGGTG | ACGTCATGGG | TAAGTACCAC | 120 |
| CCTCACGGCG | ACTCGGCCAT | TTACGACACC | TTGGTGCGTC | TGGCTCAGCC | ATGGGCCATG | 180 |
| CGATACAAGC | TTGTCCAGGG | TCAGGGTAAC | TTCGGGTCCC | AGGGCAACGA | CGGTGCGGCT | 240 |
| GCCATGCGAT | ACACCGAGTG | CAAGATGGCG | CCGCTGGCCA | TGGAGATGGT | GCGCGACATC | 300 |
| GACCAGGACA | CTGTCGATTT | CCAGCCCAAC | TATGACAACA | AGGAGACCGA | ACCGGTCGTC | 360 |
| TTGCCGTCGA | GGTTCCCCAA | CCTGCTTGTC | AATGGTTCTT | CAGGAATAGC | TGTTGGTATG | 420 |
| GCG | | | | | | 423 |

(2) INFORMATION FOR SEQ ID NO:162:

(i) SEQUENCE CHARACTERISTICS:
    (A) LENGTH: 420 base pairs
    (B) TYPE: nucleic acid
    (C) STRANDEDNESS: double
    (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
    (A) ORGANISM: Propionibacterium acnes (xi) SEQUENCE DESCRIPTION: SEQ ID NO:162:

| | | | | | | |
|---|---|---|---|---|---|---|
| GATGGGTTAA | AGCCCGTCCA | GCGCCGCATC | CTTTACACCA | TGGGAGACAT | GGGAGTTCGC | 60 |
| CCTGACCGTC | CCCATGTGAA | GTCAGCGCGA | GTCGTCGGAC | AGGTCATGGG | TCAGCTGCAC | 120 |
| CCCCACGGCG | ACGCTGCCAT | CTACGACGCC | CTGGTACGCA | CCGCTCAGCC | ATGGGCGATG | 180 |
| AGGCTCCCCC | TCGTCGACGG | TCACGGTAAC | TTCGGATCCC | TTGACGCCGG | CCCCGCTGCC | 240 |
| ATGCGTTACA | CCGAGTGTCG | GATGGCACCG | CCAGCTCTTA | CCATGATCGA | TGGGCTCGAC | 300 |
| GAAGACACCG | TTGACTTCGA | ACCTAACTAC | GACGGCAAAG | AGACCGAGCC | CTCAGTGTTG | 360 |
| CCGGCCGCCT | TCCCAAACCT | GCTCGTCAAC | GGGGCTTCGG | GGATTGCTGT | TGGTATGGCG | 420 |

(2) INFORMATION FOR SEQ ID NO:163:

(i) SEQUENCE CHARACTERISTICS:
    (A) LENGTH: 423 base pairs
    (B) TYPE: nucleic acid
    (C) STRANDEDNESS: double
    (D) TOPOLOGY: Not Relevant (ii) MOLECULE TYPE: DNA (genomic)

(iii) HYPOTHETICAL: NO ( i v ) ANTI-SENSE: NO ( v i ) ORIGINAL SOURCE:
    ( A ) ORGANISM: Porphyromonas assacharolyticus ( x i ) SEQUENCE DESCRIPTION: SEQ ID NO:163:

| | | | | | | |
|---|---|---|---|---|---|---|
| GACGGGTTGA | AGCCGGTACA | TCGACGTGTA | CGCTACTCGA | TGAATGAGAG | TGGCAATACC | 60 |
| TACAATAATC | CTACCCGCAA | GTGTGCACGC | GCCGTCGGTG | ATATCTTAGG | TAAGTATCAC | 120 |
| CCCCATGGCG | ACAGCTCCGT | ATACAATACA | CTGGTACGTC | TCGCGCAGGG | CTGGAATATG | 180 |
| CGCTACCCGC | TCGTACAGGG | ACAGGGTAAC | TTTGGTTCTA | TCGACGGGGA | CTCACCCGCT | 240 |
| GCGATGCGTT | ACACCGAGTC | GAGGCTCAAT | CAGTTTGCCC | AGGAGATGCT | CCGAGATATT | 300 |
| GACATGGAGA | CGGTGGACTT | TCAGGACAAC | TTCGACGGAG | ACTTTAAGGA | GCCTACTGTA | 360 |
| CTACCCTGTC | GCATTCCTAA | CCTTCTGATC | AATGGTGCCG | CTGGTATCGC | TGTAGGTATG | 420 |
| GCA | | | | | | 423 |

( 2 ) INFORMATION FOR SEQ ID NO:164:

( i ) SEQUENCE CHARACTERISTICS:
        ( A ) LENGTH: 396 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Porphyromonas assacharolyticus ( x i ) SEQUENCE DESCRIPTION: SEQ ID NO:164:

| | | | | | | |
|---|---|---|---|---|---|---|
| GATGGGTTAA | AACCTGTGCA | ACGACGGGTG | CGCTACACGA | TGCACCTGAT | GGAAAACGGC | 60 |
| ACCCTCCATA | AGGTTGCGAA | GATCGTGGGT | GCTACGATGG | CATACCACCC | ACACGGTGAT | 120 |
| GCCTCGATCA | ATGATGCTTT | GGTACAGCTC | GGTCAGAAGG | CTATCTCAT | CGACACGCAG | 180 |
| GGTAACTGGG | GTAACATACT | CACGGGCGAC | GAGGCGGCCG | CTGGTCGATA | CATCGAGGCT | 240 |
| AAGCTCTCTA | ACTTTGCCCT | CGAGATACTC | TTTGGTGACA | AGATCACCCC | CTGGATGAAG | 300 |
| AGCTACGACG | GCAAGTCTCG | TGAGCCTGTT | TACCTGCCCG | CCCGCTTTCC | CCTACTACTA | 360 |
| GCGCAAGGTG | CCGAGGGGAT | TGCGGTCGGT | ATGGCA | | | 396 |

( 2 ) INFORMATION FOR SEQ ID NO:165:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Pseudomonas caryophylli ( x i ) SEQUENCE DESCRIPTION: SEQ ID NO:165:

| | | | | | | |
|---|---|---|---|---|---|---|
| GACGGGTTGA | AGCCTGTGCA | CCGGCGTGTT | CTGTACGCCA | TGCACGAGCT | CAACAACGAC | 60 |
| TGGAATCGCG | CCTACAAGAA | GTCCGCGCGT | ATCGTCGGCG | ACGTCATCGG | TAAGTACCAT | 120 |

| CCCCATGGCG | ATTCGGCCGT | ATACGACACG | ATCGTGCGCA | TGGCACAGGA | CTTTTCGCTG | 180 |
| CGCTACATGC | TGGTGGACGG | GCAGGGCAAC | TTCGGTTCCG | TCGATGGCGA | CAACGCCGCG | 240 |
| GCCATGCGTT | ACACCGAAAT | CCGCATGGCG | AAGATCGGCC | ACGAACTGCT | CGCCGACATC | 300 |
| GACAAGGAAA | CCGTCGATTT | CGGCCCGAAC | TACGACGGCA | GCGAGAACGA | GCCGCTGATC | 360 |
| CTGCCCGCGC | GCATCCCCAA | TCTGCTGATC | AATGGTTCGT | CGGGCATCGC | AGTCGGTATG | 420 |
| GCA | | | | | | 423 |

( 2 ) INFORMATION FOR SEQ ID NO:166:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Pseudomonas caryophylli ( x i ) SEQUENCE DESCRIPTION: SEQ ID NO:166:

| GATGGGTTAA | AGCCGGTGCA | GCGGCGCATT | CTCTATGCAA | TGAGCGAGAT | GGGGCTTGCA | 60 |
| TCCGACGCGA | AGCCCGTCAA | GTCGGCGCGC | GTCGTCGGCG | ACGTGCTCGG | CAAGTACCAT | 120 |
| CCGCACGGCG | ACCAGTCGGC | CTATGACGCG | CTCGTGCGCC | TCGCGCAAGA | CTTCTCGATG | 180 |
| CGCTATCCGC | TCATCGACGG | GCAGGGCAAC | TTCGGCTCGC | GCGATGGCGA | TGGCGCGGCG | 240 |
| GCCATGCGTT | ACACCGAGGC | GCGCCTCACG | CCGATCGCGA | AGCTGCTGCT | CGACGAAATC | 300 |
| GACGAGGGCA | CGGTCGATTT | CATGCCGAAC | TACGACGGCT | CGTTCGAAGA | ACCCAAGCTG | 360 |
| CTGCCGGCGC | GGTTGCCGTT | CCTGCTGCTC | AATGGTGCGT | CGGGCATCGC | TGTAGGTATG | 420 |
| GCA | | | | | | 423 |

( 2 ) INFORMATION FOR SEQ ID NO:167:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Pseudomonas cepacia ( x i ) SEQUENCE DESCRIPTION: SEQ ID NO:167:

| GATGGGTTGA | AACCTGTACA | CCGGCGCGTA | CTGTTCGCGA | TGCACGAACT | GAACAACGAC | 60 |
| TGGAACCGCG | CGTACAAGAA | GTCGGCGCGT | ATCGTCGGTG | ACGTGATCGG | TAAGTACCAC | 120 |
| CCGCACGGCG | ATACGGCGGT | GTACGACACG | ATCGTGCGGA | TGGCGCAGGA | CTTCTCGCTG | 180 |
| CGCTACATGC | TGATCGACGG | GCAGGGCAAC | TTCGGCTCGA | TCGACGGCGA | CAACGCCGCG | 240 |
| GCGATGCGTT | ACACCGAAAT | TCGCATGGCG | AAGATCGGGC | ATGAGCTGCT | GGCCGACATC | 300 |
| GACAAGGAAA | CGGTCGACTT | CGAGCCGAAC | TACGACGGCA | ACGAAACGCA | GCCGTCGGTC | 360 |

```
CTGCCGTCGC GCATTCCGAA CCTGCTGATC AACGGCTCGT CGGGGATCGC CGTAGGTATG    420

GCG                                                                  423
```

( 2 ) INFORMATION FOR SEQ ID NO:168:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Pseudomonas gladioli ( x i ) SEQUENCE DESCRIPTION: SEQ ID NO:168:

```
GACGGGTTCA AGCCCGTCCA TCGGCGCGTG CTGTTCGCGA TGCACGAACT GAACAACGAC     60

TGGAACCGGG CCTACAAGAA GTCGGCGCGT ATCGTCGGCG ATGTGATCGG TAAGTACCAC    120

CCGCACGGCG ACAGTGCCGT GTACGACACC ATCGTCCGGA TGGCGCAGGA TTTCTCGCTG    180

CGTTACATGT TGGTCGACGG CCAGGGCAAC TTCGGTTCGG TCGACGGCGA CAATGCCGCC    240

GCGATGCGCT ACACCGAAAT CCGCATGGCG AAGATCGGCC ACGAGCTGCT GGTCGACATC    300

GACAAGGAAA CGGTTGACTT CGGGCCCAAC TACGACGGCA GCGAAAGCGA GCCGCTGATC    360

CTGCCGGCGC GGATCCCGAA CCTGCTGATC AACGGTTCGT CGGGCATTGC GGTCGGTATG    420

GCA                                                                  423
```

( 2 ) INFORMATION FOR SEQ ID NO:169:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Porphyromonas gingivalis ( x i ) SEQUENCE DESCRIPTION: SEQ ID NO:169:

```
GATGGGTTAA AGCCAGTTCA TCGCCGTGTG CTGTATGCCA TGAACGAAAC CGGCAATGTG     60

TACACCAATC CCACTCGCAA ATGCGCCAAT GCTGTCGGCG AAGTGCTGGG ACACTATCAC    120

CCGCATGGCG ACTCTTCCGT TTATATGGCC TTGGTGCGTA TGGCACAGCC GTGGAGCCTG    180

CGCTATCCGT TGGTGGACGG TCAGGGCAAC TTCGGTTCGG TGGATGGCGA TTCGCCTGCT    240

GCCATGCGTT ATACCGAGTC GCGCCTCAGC CGGATTGCCG GTGAGATGCT TCAGGACATA    300

GATAAGGAAA CGGTAGACTT CCAAAACAAT TTCGATGATA CACGTCAGGA GCCCACGGTT    360

CTGCCGACAC GCATTCCGAA CCTCCTCATA AACGGGGCTT CCGGGATAGC TGTAGGTATG    420

GCG                                                                  423
```

( 2 ) INFORMATION FOR SEQ ID NO:170:

( i ) SEQUENCE CHARACTERISTICS:
   ( A ) LENGTH: 399 base pairs
   ( B ) TYPE: nucleic acid
   ( C ) STRANDEDNESS: double
   ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
   ( A ) ORGANISM: Porphyromonas gingivalis ( x i ) SEQUENCE DESCRIPTION: SEQ ID NO:170:

```
GATGGGTTAA AACCAGTCCA ACGCCGCATC CTCTACACCA TGCACCATTG GTTCGACAAT      60
GGTCGTATGA ACAAGGTAGC GAAGGTGACG GGACAGACTA TGGCTCTACA CCCGCACGGC     120
GATGCTTCTA TCAACGATGC TCTCGTACAG TTGGGGCAAA AAGGCTATCT GATCGAAACG     180
CAGGGGAATT GGGGTAATAT CCTCACGGGG GACGAAGCGG CAGCCGGTCG TTACATCGAG     240
GCCAAACTCT CAGCTTTGGC TCAGGAGACT CTTTTCAATG ATAAGATTAC GCACTGGAAA     300
CGTTCTTACG ATGGCAGCGA GGACGAGCCG GTGGCTTTGC CCGTAAAGTT TCCACTTCTC     360
TTGGCACAGG GCACGGAAGG TATAGCGGTA GGTATGGCG                            399
```

( 2 ) INFORMATION FOR SEQ ID NO:171:

( i ) SEQUENCE CHARACTERISTICS:
      ( A ) LENGTH: 423 base pairs
      ( B ) TYPE: nucleic acid
      ( C ) STRANDEDNESS: double
      ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
      ( A ) ORGANISM: Pirellula marina ( x i ) SEQUENCE DESCRIPTION: SEQ ID NO:171:

```
GATGGGTTTA AGCCGGTGCA GCGCCGTATC TTGGTCGCTA TGAATGACTT AAACCTGACG      60
CCGGGCTCCG GCCGGGTGAA ATGCGCCAAG ATCTCTGGCG ATACCAGCGG TAACTATCAC     120
CCGCACGGCG AAAGCGTGAT TTATCCCACG CTCGTCCGGA TGGCCCAAGA GTGGAACACT     180
CGCTACCTGT TGGTGGACAA ACAGGGGAAC TTTGGTTCGA TCGCCGGTTT GCCTCCGGCT     240
GCGATGCGGT ATACCGAAGC CCGCATGTCC CCTTACGCGC AGATGCTGCT TGAGGATCTG     300
CGGCTCGATA CGGTCGACTA TATCCCGACC TACGATGAAC GGAACACCGA GCCGACCGTG     360
TTGCCGAGCA AGTATCCCAA CTTGCTGGTC AACGGATCGC AAGGCATCGC TGTTGGTATG     420
GCA                                                                   423
```

( 2 ) INFORMATION FOR SEQ ID NO:172:

( i ) SEQUENCE CHARACTERISTICS:
      ( A ) LENGTH: 423 base pairs
      ( B ) TYPE: nucleic acid
      ( C ) STRANDEDNESS: double
      ( D ) TOPOLOGY: Not Relevant ( i i ) MOLECULE TYPE: DNA (genomic)

( i i i ) HYPOTHETICAL: NO 5,645,994

169                                                                              170

-continued ( i v ) ANTI-SENSE: NO ( v i ) ORIGINAL SOURCE:
         ( A ) ORGANISM: Prevotella oralis ( x i ) SEQUENCE DESCRIPTION: SEQ ID NO:172:

| GATGGGTTTA | AACCGGTTCA | CCGCCGTATT | TTATACGGCA | TGTTGGGAAT | AGGGAATACG | 60 |
| AACGACAAAC | CTTATAAAAA | ATGTGCGCGT | GTAGTAGGAG | AGGTGTTGGG | AAAATACCAT | 120 |
| CCGCACGGCG | ACTCATCTGT | GTATGGCGCA | TTGGTGCGTC | TTGCACAAGA | TTGGAATATG | 180 |
| AGGTACACCC | TTGTCGATGG | TCAAGGAAAC | TTCGGTAGTG | TAGACGGTGA | TTCGGCAGCG | 240 |
| GCCATGCGTT | ATACGGAATG | TCGCCTCTCA | AAAATGGGCG | AGCATATCAT | GGATGATCTT | 300 |
| GAAAAAGACA | CCGTTGATAT | GGCCAATAAT | TTCGACGATA | CTCTGCAGGA | ACCGACGGTT | 360 |
| ATGCCGACGA | AAATACCTAA | TTTGCTCGTA | AACGGAGGCA | ACGGTATTGC | TGTGGGTATG | 420 |
| GCG        |            |            |            |            |            | 423 |

( 2 ) INFORMATION FOR SEQ ID NO:173:

( i ) SEQUENCE CHARACTERISTICS:
                  ( A ) LENGTH: 396 base pairs
                  ( B ) TYPE: nucleic acid
                  ( C ) STRANDEDNESS: double
                  ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
                  ( A ) ORGANISM: Prevotella oralis ( x i ) SEQUENCE DESCRIPTION: SEQ ID NO:173:

| GATGGGTTAA | AGCCGGTACA | GCGGCGTATA | TTGCACTCCA | TGAAGCGTAT | GGACGACGGA | 60 |
| CGCTACAACA | AGGTGGCCAA | CATCGTGGGA | CATACCATGC | AGTTTCACCC | CCACGGAGAC | 120 |
| GCTTCTATCG | GCGACGCATT | GGTGCAGATG | GGCCAGAAGG | ACTTGCTTGT | AGACACACAG | 180 |
| GGCAACTGGG | GAAACATCTT | AACAGGCGAC | CGTGCGGCCG | CTCCCCGATA | TATAGAAGCC | 240 |
| CGCTTGTCTA | AGTTTGCATT | AGACGTGGTT | TTCAATCCGA | AGACTACAGA | ATGGCAACTT | 300 |
| AGTTACGACG | GGCGTAACAA | AGAACCCATC | ACGTTGCCCG | TTAAATTTCC | CTTACTCCTT | 360 |
| GCACAGGGGG | CAGAAGGGAT | AGCAGTAGGT | ATGGCG     |            |            | 396 |

( 2 ) INFORMATION FOR SEQ ID NO:174:

( i ) SEQUENCE CHARACTERISTICS:
                  ( A ) LENGTH: 423 base pairs
                  ( B ) TYPE: nucleic acid
                  ( C ) STRANDEDNESS: double
                  ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
                  ( A ) ORGANISM: Rhodococcus equi ( x i ) SEQUENCE DESCRIPTION: SEQ ID NO:174:

| GATGGGTTTA | AGCCGGTGCA | CCGCCGCGTG | CTGTACGCGA | TGTACGACAA | CGGTTACCGT | 60 |
| CCGGACCGCG | GCTACGTGAA | GTCCGCGCGC | CCGGTCGCCG | ACACCATGGG | TAACTACCAC | 120 |

| CCGCACGGCG | ACAGCTCCAT | CTACGACACC | CTCGTGCGCA | TGGCGCAGCC | GTGGTCGCTG | 180 |
| CGCTACCCGC | TCGTCGACGG | CCAGGGCAAC | TTCGGTTCCC | GCGGCAACGA | CGGCGCGGCC | 240 |
| GCGATGCGTT | ACACCGAGTG | CCGGATGACG | CCGCTGGCCA | TGGAGATGGT | CCGCGAGATC | 300 |
| GACCACGACA | CAGTCGATTT | CGTCCCGAAC | TACGACGGCA | AGACGCAGGA | GCCGACGGTC | 360 |
| CTGCCGAGCC | GGATCCCGAA | CCTGCTCGTC | AACGGTTCCG | GCGGCATAGC | TGTCGGTATG | 420 |
| GCA | | | | | | 423 |

(2) INFORMATION FOR SEQ ID NO:175:

(i) SEQUENCE CHARACTERISTICS:
        (A) LENGTH: 423 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
        (A) ORGANISM: Rhodococcus fascians (xi) SEQUENCE DESCRIPTION: SEQ ID NO:175:

| GATGGGCTCA | AGCCGGTGCA | CCGACGTGTG | CTGTACGCGA | TGTACGACTC | GGGCTTCCGT | 60 |
| CCCGACCGTA | GCTACGTGAA | ATCCGCACGA | CCCGTTGCCG | AAACGATGGG | TAACTACCAT | 120 |
| CCCCACGGCG | ACACCTCGAT | CTACGACGCG | CTCGTGCGTC | TGGCTCAGCC | GTGGTCGATG | 180 |
| CGGTACCCAC | TGGTCGACGG | CCAGGGCAAC | TTCGGCTCCC | GCGGCAACGA | CGGCGCCGCC | 240 |
| GCCATGCGAT | ACACCGAAGC | ACGCCTGACT | CCGCTCGCCA | TGGAGATGCT | GCGCGACATC | 300 |
| GACGAGGAAA | CCGTCGACTT | CATCCCCAAC | TACGACGGCA | AAACCCAAGA | GCCGACGGTA | 360 |
| CTTCCGTCGC | GTGTGCCGAA | CCTGTTGATG | AACGGCTCCA | ACGGCATCGC | GGTCGGTATG | 420 |
| GCA | | | | | | 423 |

(2) INFORMATION FOR SEQ ID NO:176:

(i) SEQUENCE CHARACTERISTICS:
        (A) LENGTH: 423 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
        (A) ORGANISM: Rickettsia prowazekii (xi) SEQUENCE DESCRIPTION: SEQ ID NO:176:

| GATGGTTTAA | AGCCTGTGCA | TCGCCGAATT | ATCTATTCCA | TGTATGAAGC | CGGTAATCAT | 60 |
| GCTAGCAAAC | CTTATAGAAA | ATCTGCACGA | ATAGTTGGTG | ACGTGATGGG | TAAATATCAT | 120 |
| CCTCACGGTG | ATAGTGCTAT | TTATGACTCG | TTAGTACGTA | TGGCTCAAGA | TTTTTCTTTG | 180 |
| CGTCTACCAC | TTGTAGATGG | ACAAGGTAAT | TTCGGCTCAA | TGGATGGTGA | TGCAGCGGCT | 240 |
| GCGATGAGAT | ATACTGAATC | TCGCATGGCC | AAAGTTGCGC | ATAAGCTTGT | AGAAGATATT | 300 |
| GATAAAGGAA | CTGTCAGTTT | TAACATTAAT | TATGACGGTT | CTGAAGAAGA | GCCATCCGTA | 360 |

```
CTGCCTGCAA  TGTTTCCAAA  TTTATTGGTT  AATGGTAGTG  GCGGAATAGC  AGTAGGTATG    420

GCG                                                                       423
```

( 2 ) INFORMATION FOR SEQ ID NO:177:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Rickettsia prowazekii ( x i ) SEQUENCE DESCRIPTION: SEQ ID NO:177:

```
GATGGGCTTA  AACCGGTCCA  TCGTAGGTTA  TTATATGCAA  TGCTACAACT  AAGGCTTGAG     60

CCTAATTCTG  GATATAAGAA  ATGTGCAAGA  GTGGTTGGTG  ATGTAATAGG  TAAATACCAC    120

CCGCACGGTG  ATGTGGCAGT  GTATGATACA  TTGGTACGAC  TTGCACAGCA  TTTTTCATTG    180

CGTTATCCTT  TGATTGATGG  TCAGGGTAAT  TTCGGCTCTA  TAGATGGTGA  TAATGCAGCA    240

GCTATGCGTT  ATACTGAATC  ACGTATGACG  GAAATATGCA  TGTTATTAAT  GGAGGATATT    300

GATAAAGATA  CGGTAGACTT  TCGTTCTACT  TATGATGATT  CTGATTTAGA  GCCAGTAATA    360

ATGCCGGCAA  GCTTCCCTAA  TTTGCTTGCT  AACGGTTCTG  AAGGCATTGC  AGTAGGTATG    420

GCG                                                                       423
```

( 2 ) INFORMATION FOR SEQ ID NO:178:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Streptomyces griseus ( x i ) SEQUENCE DESCRIPTION: SEQ ID NO:178:

```
GATGGGTTGA  AGCCTGTTCA  CCGCCGGGTG  CTGTACGCGA  TGTACGACGG  CGGGTACCGC     60

CCCGAGAAGG  GCTTCTACAA  GTGCGCCCGC  GTCGTCGGCG  ACGTCATGGG  TACGTACCAC    120

CCGCACGGCG  ACTCCTCCAT  CTACGACGCC  CTGGTGCGCC  TCGCGCAGCC  GTGGTCGCTG    180

CGGATGCCGC  TGGTCGACTC  CAACGGCAAC  TTCGGTTCCC  CGGGCAACGA  CCCGGCCGCC    240

GCCATGCGGT  ACACCGAGTG  CAAGATGATG  CCGCTGTCCA  TGGAGATGGT  CCGGGACATC    300

GACGAGGAGA  CCGTCGACTT  CCAGGACAAC  TACGACGGCC  GCAACCAGGA  GCCGACGGTC    360

CTGCCGGCGC  GCTTCCCGAA  CCTGCTGGTC  AACGGCTCCG  CCGGGATAGC  CGTTGGTATG    420

GCA                                                                       423
```

( 2 ) INFORMATION FOR SEQ ID NO:179:

( i ) SEQUENCE CHARACTERISTICS:
: (A) LENGTH: 426 base pairs
: (B) TYPE: nucleic acid
: (C) STRANDEDNESS: double
: (D) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
: (A) ORGANISM: Streptomyces griseus ( x i ) SEQUENCE DESCRIPTION: SEQ ID NO:179:

| | | | | | | |
|---|---|---|---|---|---|---|
| GATGGGCTGA | AGCCGGTGCA | CCGGCGCATC | GTGTCCCAGA | TGAACGAGAT | GGGGCTGCGC | 60 |
| CCGACCGCGG | CTAATGTGAA | GTGCGCGCGC | GTCGTCGGCG | AGGTGATGGG | CAAGCTGCAC | 120 |
| CCGCACGGCG | ACGCCTCGAT | CTACGACGCC | CTGGTGCGCA | TGGCGCAGCC | GTTCTCGATG | 180 |
| CGCCTCCCCC | TGGTCGACGG | CCACGGCAAC | TTCGGCTCCC | TGGGCAACGA | CGACCCGCCG | 240 |
| GCCGCCATGC | GGTACACCGA | GTGCCGGATG | GCCGACGCCA | CCTCGCTGAT | GACCGAGGCG | 300 |
| ATCGACGAGG | ACACCGTCGA | CTTCCAGTCC | AACTACGACG | GCCAGGAGCG | CGAGCCGGTC | 360 |
| GTCCTCCCCG | CCGCCTATCC | CAACCTCCTG | GTCAACGGGG | TCTCCGGCAT | CGCCGTCGGT | 420 |
| ATGGCA | | | | | | 426 |

( 2 ) INFORMATION FOR SEQ ID NO:180:

( i ) SEQUENCE CHARACTERISTICS:
: (A) LENGTH: 423 base pairs
: (B) TYPE: nucleic acid
: (C) STRANDEDNESS: double
: (D) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
: (A) ORGANISM: Spirocheata aurantia ( x i ) SEQUENCE DESCRIPTION: SEQ ID NO:180:

| | | | | | | |
|---|---|---|---|---|---|---|
| GATGGGTTTA | AGCCCGTGCA | CCGGCGCATC | CTGTACGCCA | TGCACGAAAT | GGGCCTGCGC | 60 |
| GCCGGGTCGA | GCTACAAGAA | GTCGGGCCGT | ATCGTCGGCG | ACGTGCTCGG | TAAGTACCAC | 120 |
| CCCCACGGCG | ACCAGTCGAT | TTACGACGCC | CTCGTCCGCC | TGGCCCAAGA | GTTTTCCATG | 180 |
| CGCTACACCG | TGGTCCGGGG | CCAGGGGAAC | TTCGGCTCGG | TGGACGGCGA | CCCGCCGGCC | 240 |
| GCCATGCGGT | ACACCGAAGC | CAAGATGACC | CGGATCACCG | AGGAAATGCT | TCGGGACATC | 300 |
| GACAAGAACA | CCGTCGACTT | CGGCCCCAAC | TACGACGACA | GCCTCACCGA | GCCCTGGTC | 360 |
| CTTCCCACGG | CCTTCCCCTA | CCTGTTGGCC | AACGGTTCTT | CGGGCATCGC | CGTCGGTATG | 420 |
| GCA | | | | | | 423 |

( 2 ) INFORMATION FOR SEQ ID NO:181:

( i ) SEQUENCE CHARACTERISTICS:
: (A) LENGTH: 396 base pairs
: (B) TYPE: nucleic acid
: (C) STRANDEDNESS: double
: (D) TOPOLOGY: Not Relevant ( i i ) MOLECULE TYPE: DNA (genomic)

5,645,994

(iii) HYPOTHETICAL: NO (iv) ANTI-SENSE: NO (vi) ORIGINAL SOURCE:
  (A) ORGANISM: Spirocheata aurantia (xi) SEQUENCE DESCRIPTION: SEQ ID NO:181:

| | | | | | |
|---|---|---|---|---|---|
| GATGGGCTCA | AGCCTGTTCA | GCGGCGCATC | CTCCACTCCC | TCATCGAGAT | GGACGACGGG | 60 |
| AAGTTCCACA | AGGTGGCCAA | CGTCGTCGGC | TACTCCATGA | AGTACCATCC | CCACGGCGAC | 120 |
| GCGTCGATCT | ACGAGGCCCT | GGTCAACCTG | GCCAGAAGG | ACCTGTTCAT | CGACAAGCAG | 180 |
| GGGAATTTCG | GCAACATCTT | CACCGGGAC | GAGGCCGCCG | CCGGCCGTTA | CATCGAATGT | 240 |
| CGGCTCCTCC | CCCTGGCCAA | GGAAGTGCTC | TTCAACCCCG | AGATCACCGA | GTACACCGAG | 300 |
| AGCTACGACG | GGCGCAACAA | GGAGCCCGTG | GTCTTCCCGG | CCAAGCTCCC | CATCGTGCTG | 360 |
| CTCCAGGGCG | TCGAGGGCAT | CGCGGTAGGT | ATGGCA | | | 396 |

(2) INFORMATION FOR SEQ ID NO:182:

(i) SEQUENCE CHARACTERISTICS:
    (A) LENGTH: 423 base pairs
    (B) TYPE: nucleic acid
    (C) STRANDEDNESS: double
    (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
    (A) ORGANISM: Sphingomonas capsulatum (xi) SEQUENCE DESCRIPTION: SEQ ID NO:182:

| | | | | | |
|---|---|---|---|---|---|
| GATGGGTTTA | AGCCAGTCCA | TCGCCGCATC | TTGTGGACCA | GCCACGAGAA | CGGCTTCACC | 60 |
| TCGACCAAGC | CCTATCGCAA | GTCTGCGCGT | ATCGTCGGCG | ATACCATGGG | TAAGTATCAC | 120 |
| CCCCATGGCG | ACGCGGCGAT | TTACGACGCG | CTGGCGCGCA | TGACCCAGGA | CTGGTCGATG | 180 |
| CGCCTGCCGC | TGATCGACGG | CCAGGGCAAC | TTCGGCTCGA | TGGACCCCGA | TCCGCCAGCC | 240 |
| TCATCGCGCT | ATACCGAAGC | GCGCCTGGCC | AAGGCGTCGG | ACTCGCTACT | GGCAGATATC | 300 |
| GACAAGGACA | CGGTCGACTT | CCAGCCCAAC | TATGACGGGG | CGGAGCACGA | GCCGCAGGTT | 360 |
| CTGCCGGCGC | GCTTCCCCAA | TCTGCTGGTC | AATGGCGCCG | GCGGAATAGC | AGTGGGTATG | 420 |
| GCG | | | | | | 423 |

(2) INFORMATION FOR SEQ ID NO:183:

(i) SEQUENCE CHARACTERISTICS:
    (A) LENGTH: 423 base pairs
    (B) TYPE: nucleic acid
    (C) STRANDEDNESS: double
    (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
    (A) ORGANISM: Spirocheata stenostrepta (xi) SEQUENCE DESCRIPTION: SEQ ID NO:183:

| | | | | | |
|---|---|---|---|---|---|
| GACGGGTTGA | AACCGGTCCA | CAGGCGCCTG | CTTTATGCGA | TGGACGAGCT | TGGTCTCAGA | 60 |

```
CCCAACGCCG CTACGAAGAA AAGCGCTCGT ATCGCCGGTG ACGCGATGGG AAAATACCAT    120

CCGCACGGCG ATGCCTCGCT ATATGACGCC CTCGTCCGGA TGGCGCAAGA TTTTTCCCTT    180

TGCTATCCTC TCGTTCATGG CCAGGGCAAT TTCGGCTCCG TTGATGGAGA TCCTGCTGCG    240

GCGTCTCGAT ACACGGAAGC GAAGCTTTCG CGTATCGGCG ACGAGATGCT CCTTGATCTC    300

AAGAAAGAAA CAGTAGATTT TGTCCCGAAC TACGATGAAT CCTTGCGGGA GCCATCGGTC    360

CTGCCAGCAG CCATCCCGAA CCTCTTGGTA AACGGCTCGA GCGGAATCGC GGTGGGTATG    420

GCA                                                                  423
```

( 2 ) INFORMATION FOR SEQ ID NO:184:

( i ) SEQUENCE CHARACTERISTICS:
        ( A ) LENGTH: 396 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Spirocheata stenostrepta ( x i ) SEQUENCE DESCRIPTION: SEQ ID NO:184:

```
GATGGGCTTA AGCCGGTTCA GCGGCGCATC ATGCACACCC TCTTCGAGAT GGACGACGGC    60

AAGTTCCACA AGGTAGCGAA CGTCGTCGGC GCCTGCATGA AGTACCATCC GCACGGCGAC    120

GCGTCCATCG GGTCCGCTCT CGTGGTCCTT GCGAACAAGG ATCTTCAT CGACCGGCAA      180

GGGAATTTCG GCAACATCTT CACCGGGGAC GAAGCGTCCG CGGCCCGATA CATCGAATGC    240

CGCGTCACGA GCCTTGCGAA GGATCTCTTC TACCTCCCGA AGCTAACCCC CTACGTGGAT    300

TCTTACGACG GACGCAACAA GGAGCCGGTG GCCTTCCCCG CGAAGATCCC CGTGGTGCTC    360

GCCATCGGCG CCGAGGGGAT CGCCGTCGGT ATGGCA                              396
```

( 2 ) INFORMATION FOR SEQ ID NO:185:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Sphingomonas paucimobilis ( x i ) SEQUENCE DESCRIPTION: SEQ ID NO:185:

```
GATGGGTTCA AGCCTGTGCA TCGCCGTATC CTCTATTCGG CCGCCGAAAG CGGCTTCGTC    60

GCGGGCAAGC CGTACCGCAA GTCGGCGCGC ATCGTCGGCG AGCTCATGGG TAAATACCAT    120

CCGCACGGCG ACAGTGCGAT CTATGACGCG CTGGCCCGCA TGGCGCAGGA CTGGTCGATG    180

CGCGTGCCGC TGATCGACGG TCAGGGCAAT TTCGGCTCGA TGGACCCCGA TCCGCCCGCC    240

GCGATGCGTT ACACCGAAGC GCGTCTGGCC AAGGTGGCCA ATTCGCTGCT CGACGATCTC    300

GACAAGGACA CGGTCGACTT CCAGCCCAAC TATGACGGCT CGGAGCGCGA ACCCTCCGTC    360
```

| CTGCCCGCGC | AATATCCGAA | CCTGCTGGTC | AATGGCGCGG | GCGGGATCGC | TGTGGGTATG | 420 |
| GCG | | | | | | 423 |

( 2 ) INFORMATION FOR SEQ ID NO:186:

( i ) SEQUENCE CHARACTERISTICS:
           ( A ) LENGTH: 423 base pairs
           ( B ) TYPE: nucleic acid
           ( C ) STRANDEDNESS: double
           ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
           ( A ) ORGANISM: Thermus aquaticus ( x i ) SEQUENCE DESCRIPTION: SEQ ID NO:186:

| GATGGCTTA | AGCCGGTTCA | GAGGCGCATC | CTCTTCGCCG | CCTACCAGGA | GGGGGTCCTC | 60 |
| CCGGGGCGCA | AGCACGTGAA | GAGCGCCAAG | ATCGTGGGCG | AGGTCATGGG | CAAGTACCAC | 120 |
| CCCCACGGGG | ACGCCGCCAT | CTACGACGCC | CTGGCCCGCC | TGGCCCAGCC | CTGGAACCTC | 180 |
| CGCTACCCCC | TCATTGACGG | CCAGGGCAAC | TTCGGCTCCA | TAGACGGGGA | CCCCCCGGCG | 240 |
| GCCCAGCGCT | ACACCGAGGC | CAGGCTGTCG | CCCATCGGGG | CGGAGATGCT | CCAGGACATG | 300 |
| GACAAGGAGA | CGGTGGACTT | CCGCCCCAAC | TACGATGGCT | CCCTTAAGGA | GCCCGAGGTC | 360 |
| CTGCCCGCCG | CCATCCCCAA | CCTTCTGGTG | AACGGCTCAA | GCGGCATCGC | GGTGGGTATG | 420 |
| GCA | | | | | | 423 |

( 2 ) INFORMATION FOR SEQ ID NO:187:

( i ) SEQUENCE CHARACTERISTICS:
           ( A ) LENGTH: 423 base pairs
           ( B ) TYPE: nucleic acid
           ( C ) STRANDEDNESS: double
           ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
           ( A ) ORGANISM: Thermotoga maritima ( x i ) SEQUENCE DESCRIPTION: SEQ ID NO:187:

| GACGGGTTGA | AACCGGTGCA | GAGGAGAATC | CTCTATGGAA | TGTACGAACT | CGGCCTCAAG | 60 |
| CACAACTCAC | CCACAAAGAA | GAGTGCGAGA | ATCGTCGGTG | AAGTGATGGG | TAAGTACCAT | 120 |
| CCTCACGGCG | ACGCACCCGT | GTATGATGCT | CTCGTGAGGA | TGGCTCAACC | GTACACGATG | 180 |
| AGGTATCCAC | TCATAGAGGG | TCAGGAAAC | TTCGGTTCCA | TAGACAGAGA | CCCTCCAGCC | 240 |
| GCGATGAGGT | ACACGGAAGC | GAGACTCACG | AGGCTCGCAG | AAGAAATGCT | CGAAGACATA | 300 |
| GAAAAGAACA | CGGTGAACAT | GATCGACAAT | TTCGATGGCA | CGCTGAAGGA | GCCTGAAGTC | 360 |
| CTCCCATCCA | AAGTGCCAAA | TCTCATAATA | AACGGTGCCT | CCGGAATCGC | GGTTGGTATG | 420 |
| GCA | | | | | | 423 |

( 2 ) INFORMATION FOR SEQ ID NO:188:

5,645,994

183

184

-continued ( i ) SEQUENCE CHARACTERISTICS:
    ( A ) LENGTH: 423 base pairs
    ( B ) TYPE: nucleic acid
    ( C ) STRANDEDNESS: double
    ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Thermomicrobium roseum ( x i ) SEQUENCE DESCRIPTION: SEQ ID NO:188:

| GACGGGCTAA | AGCCTGTGCA | GCGGCGGATC | TTGTACGGCA | TGTACGAAAT | GGGCCTGCGC | 60 |
| CCAAATGCCA | AGTACCGTAA | GAGCGCCGGT | ATCGTCGGTG | AGGTCCTGAA | GTCGTATCAC | 120 |
| CCCCACGGGG | ACAGTGCGGT | CTACGACGCC | CTGGTTCGCA | TGGTCCAGCC | ATTCACCATG | 180 |
| CGGTACCCCT | TGATCGACGG | GCAGGGTAAT | TTCGGCTCCG | TCGACGGCGA | TAGTGCCGCC | 240 |
| GCGATGCGCT | ACACTGAGGC | GCGCCTCGCT | CCGATCGCTG | AAGAACTGCT | CGCGGACATC | 300 |
| GACAAGCAAA | CGGTCGACTT | CGTTCCCAAC | TATGACGATA | GCACGCGCGA | ACCCTCGGTC | 360 |
| CTCCCAGCCC | GTCTACCGAA | CCTTCTCGTC | AACGGGGCAA | GCGGAATCGC | CGTCGGTATG | 420 |
| GCA | | | | | | 423 |

( 2 ) INFORMATION FOR SEQ ID NO:189:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Thermus thermophilus ( x i ) SEQUENCE DESCRIPTION: SEQ ID NO:189:

| GACGGGTTGA | AGCCCGTCCA | GAGGCGGATC | CTCTTCGGCG | CCTACCAGGA | AGGGGTCCTG | 60 |
| CCGGGACGCA | AGCACGTGAA | GAGCGCCAAG | ATCGTGGGCG | AGGTCATGGG | CAAGTACCAC | 120 |
| CCCCACGGGG | ACGCCGCCAT | CTACGACGCC | CTGGTGCGCA | TGGCCCAGCC | CTGGAACCTC | 180 |
| CGCTACCCCC | TCATTGACGG | CCAGGGGAAC | TTCGGCTCCA | TAGACGGCGA | CCCCCCGGCG | 240 |
| GCCCAGCGCT | ACACCGAGGC | CAGGCTTTCC | CCCATCGGGG | CGGAGATGCT | TTTGGACATT | 300 |
| GACAAGGACA | CGGTGGACTT | CCGCCCCAAC | TACGACGGCT | CCCTCAAGGA | GCCCGAGGTC | 360 |
| CTGCCCGCCG | CCATCCCCAA | CCTCCTGGTG | AACGGGCGA | GCGGATCGC | GGTGGGTATG | 420 |
| GCA | | | | | | 423 |

( 2 ) INFORMATION FOR SEQ ID NO:190:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: Not Relevant ( i i ) MOLECULE TYPE: DNA (genomic)

(iii) HYPOTHETICAL: NO (iv) ANTI-SENSE: NO (vi) ORIGINAL SOURCE:
    (A) ORGANISM: Ureaplasma urealyticum (xi) SEQUENCE DESCRIPTION: SEQ ID NO:190:

| | | | | | | |
|---|---|---|---|---|---|---|
| GATGGGCTAA | AGCCCGTACA | TCGAAGAGCA | TTATTTGCTG | CTTTCGAAAA | TGGAATGACA | 60 |
| CACGATAAAC | CCTATAAAAA | ATCTGCGCGT | TGAGTAGGGG | ATGTAATTGG | AAAGTACCAC | 120 |
| CCTCATGGGG | ATCAAGCCGT | TTATCAAACG | ATTGTAAGAA | TGGCGCAAGA | ATTTTCAATG | 180 |
| CGTTATTTAC | TAGTTGATGG | TCATGGTAAC | TTTGGGTCAA | TTGATGGTGA | TAGTGCAGCT | 240 |
| GCG..TGCGTT | ATACAGAAGC | GCGATTGTCA | AAAATTTCTT | ATGAGTTATT | AAAATACATT | 300 |
| GATAAAGAAA | CAGTTGATTT | TGTACCTAAC | TATGATGCGT | CAGAACAAGA | ACCAAGTGTT | 360 |
| TTGCCATCAG | GTTTTCCAAA | TTTATTAACA | AATGGAACAA | CAGGGATTGC | TGTCGGTATG | 420 |
| GCA | | | | | | 423 |

(2) INFORMATION FOR SEQ ID NO:191:

(i) SEQUENCE CHARACTERISTICS:
    (A) LENGTH: 423 base pairs
    (B) TYPE: nucleic acid
    (C) STRANDEDNESS: double
    (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
    (A) ORGANISM: Ureaplasma urealyticum (xi) SEQUENCE DESCRIPTION: SEQ ID NO:191:

| | | | | | | |
|---|---|---|---|---|---|---|
| GACGGGTTTA | AGCCGGTTCA | ACGACGTATT | TTGTATGCCA | TGAGCGAATT | AGGAATTTTT | 60 |
| CATGACAAAC | CTTACAAAAA | ATCAGCACGT | ACAGTTGGGG | AAGTAATTGG | TAAATACCAC | 120 |
| CCTCATGGTG | ATTCATCAAT | TTATGAAGCT | ATGGTAAGAA | TGAGTCAAGA | TTGAAAAAAT | 180 |
| AATTTATGCT | TATTAGATAT | GCATGGTAAT | AAAGGTTCGA | TTGATGGTGA | TAACGCTGCT | 240 |
| GCGATGCGTT | ATACAGAAAC | ACGTTTATCA | AAAATTGCTA | GTGTAATGCT | AACTAATTTA | 300 |
| AAAAAGATG | TAGTTAAATT | TAGTCCAAAC | TTTGATGATA | GTGAAAAAGA | ACCATCAATT | 360 |
| TTACCATCAC | TTTTTCCTAA | CTTATTAATT | AATGGAGTAA | CAGGAATTGC | TGTCGGTATG | 420 |
| GCA | | | | | | 423 |

(2) INFORMATION FOR SEQ ID NO:192:

(i) SEQUENCE CHARACTERISTICS:
    (A) LENGTH: 423 base pairs
    (B) TYPE: nucleic acid
    (C) STRANDEDNESS: double
    (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
    (A) ORGANISM: Vibrio fischeri (xi) SEQUENCE DESCRIPTION: SEQ ID NO:192:

```
GACGGGTTCA  AACCTGTACA  CCGCCGCGTT  TTATTCGCAA  TGGATGTACT  AGGTAATGAT    60

TGGAATAAAC  CATATAAAAA  ATCTGCCCGT  GTTGTTGGCG  ACGTAATCGG  TAAATATCAC   120

CCTCACGGTG  ATAGTGCTGT  TTATGACACC  ATCGTACGTA  TGGCGCACGG  TTTCTCACTA   180

CGCTATATGC  TTGTTGATGG  CCAAGGTAAC  TTCGGTTCTA  TCGATGGTGA  CTCAGCGGCG   240

GCGATGCGTT  ATACCGAAGT  TCGTATGGCG  AAAATCGCTC  ACGAATTATT  GGCTGATCTA   300

GACAAAGAAA  CTGTAGATTA  TGTTCCTAAC  TATGATGGTA  CAGAACATAT  CCCTGCAGTA   360

TTACCAACAA  AGATCCCGAA  CCTACTTGTA  AATGGTTCAT  CAGGGATCGC  AGTGGGTATG   420

GCG                                                                      423
```

(2) INFORMATION FOR SEQ ID NO:193:

(i) SEQUENCE CHARACTERISTICS:
        (A) LENGTH: 426 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
        (A) ORGANISM: Vibrio fischeri (xi) SEQUENCE DESCRIPTION: SEQ ID NO:193:

```
GATGGGCTGA  AACCTGCACA  ACGTCGTATT  ATTTACGCGA  TGTCTGAACT  TGGATTATCA    60

GCAAACGCAA  AGTATAAGAA  ATCAGCACGT  ACCGTTGGTG  ATGTATTAGG  TAAGTACCAC   120

CCACACGGTG  ACTCTGCGTG  TTATGAAGCC  ATGGTATTAA  TGGCTCAGCC  TTTCTCTTAT   180

CGTTATCCAC  TAGTTGATGG  TCAAGGTAAC  TGGGGTGCTC  CAGATGATCC  GAAATCATTT   240

GCTGCGATGC  GTTATACGGA  ATCAAAACTG  TCTAAGTTTG  CTGATGTATT  GCTAGGCGAA   300

ATTGGTCAAG  GTACGGTTGA  TTGGCAACCA  AACTTTGATG  GCACAATGAA  AGAGCCAACG   360

ATATTACCTT  CACGTTTACC  TCATATTTTA  TTGAATGGTA  TTACTGGGAT  TGCGGTGGGT   420

ATGGCG                                                                   426
```

(2) INFORMATION FOR SEQ ID NO:194:

(i) SEQUENCE CHARACTERISTICS:
        (A) LENGTH: 423 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
        (A) ORGANISM: Xanthomonas badrii (xi) SEQUENCE DESCRIPTION: SEQ ID NO:194:

```
GACGGGTTGA  AGCCGGTGCA  CCGGCGCGTG  CTGTACGCGA  TGCACGAGCT  TGGCGCACAC    60

AGCAACAAGG  CCTACTTCAA  GTCGGCGCGT  ATCGTCGGCG  ACGTCATCGG  TAAGTACCAC   120

CCGCACGGCG  ACCAGTCGGT  GTACGACACG  CTGGTGCGCA  TGGCGCAGCC  GTTCTCGCTG   180

CGCTACATGA  TGGTGGACGG  CCAGGGTAAC  TTCGGTTCGG  TCGACGGCGA  CTCCGCCGCG   240
```

| GCAATGCGTT | ACACCGAGTC | GCGCATGTCG | CGGCTGGCGC | ATGAGCTGAT | GGCCGACATC | 300 |
|---|---|---|---|---|---|---|
| GACAAGGAAA | CCGTCGACTT | CCAGCCCAAT | TACGACGAAA | AGGAATTGGA | ACCGACGGTC | 360 |
| ATGCCGACCC | GGTTCCCGAG | CCTGCTGGTC | AATGGCTCGG | CCGGCATCGC | CGTAGGTATG | 420 |
| GCA | | | | | | 423 |

( 2 ) INFORMATION FOR SEQ ID NO:195:

( i ) SEQUENCE CHARACTERISTICS:
        ( A ) LENGTH: 427 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Xanthomonas badrii ( x i ) SEQUENCE DESCRIPTION: SEQ ID NO:195:

| GATGGGCTTG | AGCCGGTTCA | GCGCCGCATC | GTCTATGCGA | TGAGCGAGCT | GGGCCTGAAC | 60 |
|---|---|---|---|---|---|---|
| GCGGCCGCCA | AGCCGAAGAA | GTCCGCGCGC | ACCGTGGGCG | ATGTGATCGG | TAAGTACCAC | 120 |
| CCGCATGGCG | ACAGCGCCTG | CTACGAGGCG | CTGGTGCTAA | TGGCGCAGCC | GTTCTCGTAC | 180 |
| CGCTATCCGC | TGATCGAAGG | CCAGGGCAAC | TTCGGCTCCA | CCGACGATCC | CAAGTCGTTC | 240 |
| GCGGCGATGC | GTTACACCGA | ATCCAAGCTG | ACCCCGATCG | CCGAAGTGCT | GCTGGGCGAA | 300 |
| ATCAGCCAGG | GCACCACCGA | CTGGGCGCCC | AACTTCGACG | GCACCCTGGA | AGAACCCACC | 360 |
| TGGTTGCCGG | CGCGCCTGCC | GCACCTGCTG | CTCAACGGCA | CCACCGGCAT | TGCAGTAGGT | 420 |
| ATGGCAA | | | | | | 427 |

( 2 ) INFORMATION FOR SEQ ID NO:196:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: Not Relevant ( i i ) MOLECULE TYPE: other nucleic acid
        ( A ) DESCRIPTION: /desc ="Primer derived from gyrA"

( i i i ) HYPOTHETICAL: NO ( i v ) ANTI-SENSE: NO ( v i ) ORIGINAL SOURCE:
        ( A ) ORGANISM: Salmonella typhimurium ( x i ) SEQUENCE DESCRIPTION: SEQ ID NO:196:

| GCGTACTTTA | CGCCATGAAC | GTAT | 24 |
|---|---|---|---|

( 2 ) INFORMATION FOR SEQ ID NO:197:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Downstream primer for gyrA"

( i i i ) HYPOTHETICAL: NO ( v i ) ORIGINAL SOURCE:
    ( A ) ORGANISM: Salmonella typhimurium ( x i ) SEQUENCE DESCRIPTION: SEQ ID NO:197:

AGATCGGCCA TCAGTTCGTG GGCG 24

( 2 ) INFORMATION FOR SEQ ID NO:198:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Upstream primer for gyrA"

( i i i ) HYPOTHETICAL: NO ( v i ) ORIGINAL SOURCE:
        ( A ) ORGANISM: Listeria monocytogenese ( x i ) SEQUENCE DESCRIPTION: SEQ ID NO:198:

TTAGGTATGA CTTCTGATAA AGCC 24

( 2 ) INFORMATION FOR SEQ ID NO:199:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Downstream primer for gyrA"

( i i i ) HYPOTHETICAL: NO ( v i ) ORIGINAL SOURCE:
        ( A ) ORGANISM: Listeria monocytogenase ( x i ) SEQUENCE DESCRIPTION: SEQ ID NO:199:

TCAGAACCAT CGTAGTTATC AGCG 24

( 2 ) INFORMATION FOR SEQ ID NO:200:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Upstream primer for parC"

( i i i ) HYPOTHETICAL: NO ( v i ) ORIGINAL SOURCE:
        ( A ) ORGANISM: Chlamydia trachomatis ( x i ) SEQUENCE DESCRIPTION: SEQ ID NO:200:

CAAAGAAGGC TTCTTTGGAC CTTA 24

( 2 ) INFORMATION FOR SEQ ID NO:201:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear (  i  i  ) MOLECULE TYPE: other nucleic acid
    ( A ) DESCRIPTION: /desc ="Downstream primer for parC
        internal segment"

(  i  i  i  ) HYPOTHETICAL: NO ( v  i ) ORIGINAL SOURCE:
    ( A ) ORGANISM: Chlamydia trachomatis ( x  i ) SEQUENCE DESCRIPTION: SEQ ID NO:201:

TCCATCGTAA GAATCATGGA AGGT 24

( 2 ) INFORMATION FOR SEQ ID NO:202:

(  i  ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear (  i  i  ) MOLECULE TYPE: other nucleic acid
        ( A ) DESCRIPTION: /desc ="Upstream primer for gyrA
            internal segment"

(  i  i  i  ) HYPOTHETICAL: NO ( v  i ) ORIGINAL SOURCE:
        ( A ) ORGANISM: Actinomyces isrealii ( x  i ) SEQUENCE DESCRIPTION: SEQ ID NO:202:

TACGACGGCG GCTACCGCCC CAGC 24

( 2 ) INFORMATION FOR SEQ ID NO:203:

(  i  ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear (  i  i  ) MOLECULE TYPE: other nucleic acid
        ( A ) DESCRIPTION: /desc ="Downstream primer for gyrA
            internal segment"

(  i  i  i  ) HYPOTHETICAL: NO ( v  i ) ORIGINAL SOURCE:
        ( A ) ORGANISM: Actinomyces isrealii ( x  i ) SEQUENCE DESCRIPTION: SEQ ID NO:203:

GTTGTCCTGG AAGTCGACGC TCTC 24

( 2 ) INFORMATION FOR SEQ ID NO:204:

(  i  ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear (  i  i  ) MOLECULE TYPE: other nucleic acid
        ( A ) DESCRIPTION: /desc ="Upstream primer for gyrA
            internal segment"

(  i  i  i  ) HYPOTHETICAL: NO ( v  i ) ORIGINAL SOURCE:
        ( A ) ORGANISM: Borrelia burgdorferi ( x  i ) SEQUENCE DESCRIPTION: SEQ ID NO:204:

ATGTATGAGA TGGGACTTCG TTCT 24

( 2 ) INFORMATION FOR SEQ ID NO:205:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Downstream primer for gyrA internal segment"

( i i i ) HYPOTHETICAL: NO ( v i ) ORIGINAL SOURCE:
        ( A ) ORGANISM: Borrelia burgdorferi ( x i ) SEQUENCE DESCRIPTION: SEQ ID NO:205:

TGGAAATGAT GACGGCATAA TCTC        24

( 2 ) INFORMATION FOR SEQ ID NO:206:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Upstream primer for gyrA internal segment"

( i i i ) HYPOTHETICAL: NO ( v i ) ORIGINAL SOURCE:
        ( A ) ORGANISM: Thermotoga maritima ( x i ) SEQUENCE DESCRIPTION: SEQ ID NO:206:

GGAATGTACG AACTCGGCCT CAAG        24

( 2 ) INFORMATION FOR SEQ ID NO:207:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Downstream primer for gyrA internal segment"

( i i i ) HYPOTHETICAL: NO ( v i ) ORIGINAL SOURCE:
        ( A ) ORGANISM: Thermotoga maritima ( x i ) SEQUENCE DESCRIPTION: SEQ ID NO:207:

AAATTGTCGA TCATGTTCAC CGTG        24